US008362297B2

(12) United States Patent
Scheele

(10) Patent No.: US 8,362,297 B2
(45) Date of Patent: Jan. 29, 2013

(54) HIGH PROTEIN SUPPLEMENT

(76) Inventor: George Scheele, La Jolla, CA (US)

(*) Notice: Subject to any disclaimer, the term of this patent is extended or adjusted under 35 U.S.C. 154(b) by 0 days.

(21) Appl. No.: 13/164,536

(22) Filed: Jun. 20, 2011

(65) Prior Publication Data

US 2011/0245158 A1 Oct. 6, 2011

Related U.S. Application Data

(60) Division of application No. 12/135,933, filed on Jun. 9, 2008, now Pat. No. 7,982,066, which is a continuation-in-part of application No. PCT/US2006/047127, filed on Dec. 8, 2006.

(60) Provisional application No. 60/749,293, filed on Dec. 9, 2005, provisional application No. 61/037,601, filed on Mar. 18, 2008.

(51) Int. Cl.
C07C 205/00 (2006.01)
C07C 207/00 (2006.01)
C07C 229/00 (2006.01)
A61K 38/00 (2006.01)
A61P 3/04 (2006.01)

(52) U.S. Cl. .................. 562/553; 514/4.8; 514/4.9

(58) Field of Classification Search .................. None
See application file for complete search history.

(56) References Cited

U.S. PATENT DOCUMENTS

| 3,845,770 | A | 11/1974 | Theeuwes |
| 3,916,899 | A | 11/1975 | Theeuwes |
| 4,008,719 | A | 2/1977 | Theeuwes |
| 4,036,228 | A | 7/1977 | Theeuwes |
| 4,042,687 | A | 8/1977 | Gans et al. |
| 4,414,238 | A | 11/1983 | Schmidl |
| 4,833,128 | A * | 5/1989 | Solomon et al. ............ 514/23 |
| 4,873,191 | A | 10/1989 | Wagner et al. |
| 5,053,387 | A * | 10/1991 | Alexander ............ 514/9.4 |
| 5,132,113 | A | 7/1992 | Luca |
| 5,242,697 | A | 9/1993 | Luca |
| 5,250,513 | A | 10/1993 | N'Guyen et al. |
| 5,661,130 | A | 8/1997 | Meezan et al. |
| 5,716,926 | A | 2/1998 | Beale et al. |
| 5,889,040 | A | 3/1999 | Beale et al. |
| 5,922,766 | A | 7/1999 | Acosta et al. |
| 5,925,377 | A | 7/1999 | Gerth et al. |
| 6,063,432 | A | 5/2000 | Maxwell et al. |
| 6,221,836 | B1 | 4/2001 | Beale et al. |
| 6,245,803 | B1 | 6/2001 | Acosta et al. |
| 6,261,598 | B1 | 7/2001 | Runge et al. |
| 6,346,264 | B1 | 2/2002 | White |
| 6,403,129 | B1 | 6/2002 | Clark et al. |
| 6,429,190 | B1 | 8/2002 | Portman |
| 6,534,085 | B1 | 3/2003 | Zeligs |
| 7,151,091 | B2 | 12/2006 | Scheele |
| 2003/0185876 | A1 | 10/2003 | Calton et al. |
| 2004/0071825 | A1 | 4/2004 | Lockwood |
| 2004/0213838 | A1 | 10/2004 | Mazer et al. |
| 2005/0015847 | A1 | 1/2005 | Scheele |
| 2006/0088574 | A1 | 4/2006 | Manning et al. |
| 2007/0173481 | A1 | 7/2007 | Scheele |
| 2009/0186056 | A1 | 7/2009 | Scheele |
| 2009/0324643 | A1 | 12/2009 | Scheele |

FOREIGN PATENT DOCUMENTS

| WO | 91/19481 | 12/1991 |
| WO | 2004/037203 | 5/2004 |
| WO | 2007/070454 | 6/2007 |

OTHER PUBLICATIONS

Rose et al. The relation of arginine and histidine to growth. JBC, 1924. pp. 747-773.*
Wu et al. "Rapid intravenous administration of amino acids prevents biliary sludge induced by total parenteral nutrition in humans." J. Hepatobiliary Pancreat. Surg. 7:504-509, 2000.
"Avoid Chronic Degenerative Disease with Factor 4 Weight Control" video available online at: www.youtube.com/watch?v=JDxxv7la1iQ.
Dr. Scheele's Aging Health 4 Life found at www.aginghealth4life.com/ (accessed on Sep. 16, 2010) 7 pages.
"Dr. Scheele's Factor 4 Weight Control, Weight Loss Testimonials," video available online at: www.factor4health.com/pages/weight-loss-testimonials-pv-c2-16.html.
Kelly et al. "Weight-Control Powders" San Diego Reader Jul. 30, 2008.
Scheele G. and Kern H. In "The Exocrine Pancreas: Biology, Pathobiology, and Disease", Eds. Go et al., "Regulation of gene expression in the exocrine pancreas," Raven Press:New York, Chapter 6:55-67, 1985.
Brinster et al. "Factors affecting the efficiency of introducing foreign DNA into mice by microinjecting eggs." Proc. Natl. Acad. Sci. USA 82:4438-4442, 1985.
Giroux et al. "Addition of arginine by not glycine to lysine plus methionine-enriched diets modulates serum cholesterol and liver phospholipids in rabbits." J. Nutr. 1269:1807-1813, 1999.
Lindgren et al. "Passage of cell-penetrating peptides across a human epithelial cell layer in vitro" Biochem. J. 377:69-76, 2004.
McCune et al. "Treatment of recurrent herpes simplex infections with L-lysine monohydrochloride" Cutis 34:366-373, 1984, Abstract only.
Osborne et al. "Skin penetration enhancers cited in the literature" Pharm Tech 21:58-66, 1997.
Padfield et al. In "The Pancreas: Biology, Pathobiology, and Disease," 2nd Edition, Eds., Go et al. "The use of two-dimensional gel electrophoresis and high performance liquid chromatography for the analysis of pancreatic juice," Raven Press: New York, 14:265-273, 1993.
Pitchumoni et al. In "The Pancreas: Biology, Pathobiology, and Disease," 2nd Edition, Eds., Go et al. "Independence of nutrition and exocrine pancreatic function," Raven Press: New York, 22:449-473, 1993.
Scheele et al. "Characterization of human exocrine pancreatic proteins by two-dimensional isoelectric focusing/sodium dodecyl sulfate gel electrophoresis," Gastroenterology 80:461-473, 1981.

(Continued)

Primary Examiner — Marcela M Cordero Garcia
(74) Attorney, Agent, or Firm — K&L Gates LLP; Louis C. Cullman; Michelle Glasky Bergman

(57) ABSTRACT

The present disclosure relates to high protein dietary supplements for treating various symptoms and diseases associated with protein deficiency including weight gain, obesity, catabolic diseases, fibromyalgia, anxiety reactions, posttraumatic stress and chronic fatigue syndrome. Embodiments of dietary supplements comprise combinations of proteins, essential and semi-essential amino acids including L-Lysine, L-Arginine, and/or L-Histidine.

12 Claims, 2 Drawing Sheets

OTHER PUBLICATIONS

Scheele et al. "Idenfication of proteins according to biological activity following separation by two-dimensional isoelectric focusing/sodium dodecyl sulfate gel electrophoresis: analysis of human exocrine pancreatic proteins," Anal. Biochem. 112:304-313, 1981.

Scheele et al. "Mechanism of compartmentalization of secretory proteins:transport of exocrine pancreatic proteins across the microsomal membrane," J. Cell. Biol. 87:611-628, 1980.

Scheele "Human pancreatic cancer: analysis of proteins contained in pancreatic juice by two dimensional isoelectic focusing/sodium dodecyl sulfate gel electrophoresis," Cancer 47(Suppl):1513-1515, 1981.

Scheele et al. In "The Pancreas: Biology, Pathobiology, and Disease," 2nd Edition, Eds., Go et al. "Cellular compartmentalization, protein processing, and secretion in the exocrine pancreas," Raven Press: New York, 8:121-150, 1993.

Scheele "Analysis of the secretory proteins in the exocrine pancrease by two dimensional isoelectic focusing/sodium dodecyl sulfate gel electrophoresis," Methods Cell. Biol. 23:345-358, 1981.

Scheele "Power Amino Acids(R): The Factor4 Advantage in Weight Loss Success." 2009.

Scheele et al. In "The Pancreas: Biology, Pathobiology, and Disease," 2nd Edition, Eds., Go et al. "Regulation of pancreatic gene expression in response to hormones and nutritional substrates," Raven Press: New York, 7:103-120, 1993.

Scheele "Two-dimensional electrophoresis in basic clinical research, as exemplified by studies on the exocrine pancreas," Clin. Chem. 28:1057-1061, 1982.

Schick et al. "Two distinct adaptive responses in the synthesis of exocrine pancreatic enzymes to inverse changes in protein and carbohydrate in the diet," Am. J. Physiol 247:G611-G616, 1984.

Tartakoff "Geroge Emile Palade: charismatic virtuoso of cell biology," Mol. Cell. Biol. 3"871-876, 2002.

Moodie et al. "Determination of amino acids in urine by gas chromatography," J. High Res. Chromatograph. 12:437-441, 1989.

* cited by examiner

HIGH PROTEIN SUPPLEMENT

CROSS REFERENCE TO RELATED APPLICATIONS

This application is a division of U.S. patent application Ser. No. 12/135,933, filed on Jun. 9, 2008, which claims the benefit of priority to and is a continuation-in-part of International Application No. PCT/US2006/047127, filed on Dec. 8, 2006, which designated the United States and was published in English and which claims the benefit of priority to U.S. Provisional Application Ser. No. 60/749,293, filed Dec. 9, 2005. U.S. patent application Ser. No. 12/135,933 also claims the benefit of priority to U.S. Provisional Application Ser. No. 61/037,601, filed Mar. 18, 2008. The disclosures of all of the aforementioned applications are hereby expressly incorporated by reference in their entireties.

FIELD OF THE INVENTION

This application concerns protein-based dietary supplements that provide nutritional benefit and improve the health and well-being of consumers. Some embodiments include particular formulations of a protein powder that has been supplemented with essential and semi-essential amino acids, in particular positively charged free-form amino acids (e.g., Lysine, Arginine, and/or Histidine), in an amount that improves the health and well being of a consumer (e.g., improves weight loss or otherwise improves a nutritional imbalance).

BACKGROUND

Many people suffer from protein deficiencies, which lead to poor health and disease. In advanced cultures, wherein sedentary behavior is commonplace, weight-related health problems are significant. Existing food products, which are derived from animal, fish, vegetable and plant sources, are insufficient to provide the body with a balanced biological and physiological diet. Approaches to ameliorate this problem often involve the use of crude forms of proteins including whey or casein. Since it takes hours for proteins to be digested in the digestive tract, their absorption may not occur fully before passing and therefore the full nutritional benefits of the proteins are not realized. For example, whey and casein proteins are digested in about 2 and 8 hours, respectively. In contrast, the free-forms of the essential (and semi-essential) amino acids are absorbed in the stomach and intestinal tract within minutes (3-10 minutes) of ingestion. Thus, the immediate effects of the Power Amino Acid Complex is due to their rapid absorption into the blood circulation resulting in suppression of appetite, food cravings, hunger attacks, and famished states. As a result of ingesting the Power Amino Acid Complex alone (e.g., in water), one experiences the feelings of comfort, satisfaction, and well-being within minutes similarly as one experiences after consumption of the Power Amino Acid Complex-containing Factor-4 shake product. Accordingly, the need for dietary supplements that address weight-related health problems and improve nutritional imbalance is manifest.

SUMMARY

In an embodiment, a dietary supplement comprises at least 1 g of whey protein, egg protein, or soy protein per 16.5 g serving and at least 10 mg of monopeptidic (free-form) Lysine per 16.5 g serving. In some embodiments the dietary supplement comprises at least 5 g of whey protein, egg protein, or soy protein per 16.5 g serving. In some embodiments the dietary supplement comprises at least 125 mg of monopeptidic (free-form) Lysine per 16.5 g serving. In some embodiments the dietary supplement comprises at least 250 mg of monopeptidic (free-form) Lysine per 16.5 g serving. In some embodiments the dietary supplement comprises at least 500 mg of monopeptidic (free-form) Lysine per 16.5 g serving. In some embodiments the dietary supplement comprises at least 750 mg of monopeptidic (free-form) Lysine per 16.5 g serving. In some embodiments the dietary supplement further comprises at least 10 mg of monopeptidic (free-form) Arginine per 16.5 g serving. In some embodiments the dietary supplement further comprises at least 125 mg of monopeptidic (free-form) Arginine per 16.5 g serving. In some embodiments the dietary supplement further comprises at least 250 mg of monopeptidic (free-form) Arginine per 16.5 g serving. In some embodiments the dietary supplement further comprises at least 500 mg of monopeptidic (free-form) Arginine per 16.5 g serving. In some embodiments the dietary supplement further comprises at least 750 mg of monopeptidic (free-form) Arginine per 16.5 g serving. In some embodiments the dietary supplement further comprises at least 10 mg of monopeptidic (free-form) Histidine per 16.5 g serving. In some embodiments the dietary supplement further comprises at least 125 mg of monopeptidic (free-form) Histidine per 16.5 g serving. In some embodiments the dietary supplement further comprises at least 250 mg of monopeptidic (free-form) Histidine per 16.5 g serving. In some embodiments the dietary supplement further comprises at least 500 mg of monopeptidic (free-form) Histidine per 16.5 g serving. In some embodiments the dietary supplement further comprises at least 750 mg of monopeptidic (free-form) Histidine per 16.5 g serving. In some embodiments, the dietary supplement is formulated in a powder or liquid form. In some embodiments, the monopeptidic (free-form) Lysine is formulated for sustained release, time-release, or extended release. In some embodiments, the monopeptidic (free-form) Lysine, Arginine, or Histidine is formulated for sustained release, time-release, or extended release.

Embodiments also include methods of using the dietary supplements described herein to improve a condition associated with excess caloric intake in a subject. By some approaches, these methods comprise identifying a subject in need of a composition that increases the amount of Lysine, Arginine, or Histidine in their diet and providing the subject an effective amount of a dietary supplement, as described herein, for a time sufficient to improve said condition associated with excess caloric intake.

Embodiments also include methods, wherein the condition associated with excess caloric intake is selected from the group consisting of excess bodyweight, obesity, and morbid obesity. Embodiments also include methods, wherein the subject has a body mass index (BMI) that is greater than that of a healthy subject of the same gender and age. Embodiments also include methods, wherein the amount of Lysine, Arginine, or Histidine in the subject's diet is measured. Embodiments also include methods, wherein the identification step is performed by obtaining a biological sample from the subject, measuring the amount of Lysine, Arginine, or Histidine in the biological sample and comparing the amount of Lysine, Arginine, or Histidine measured in the biological sample from the subject to the amount of Lysine, Arginine, or Histidine present in a biological sample obtained from a second subject.

Embodiments also include methods of using a dietary supplement described herein to improve a nutritional imbalance in a subject and some of these methods comprise identifying a subject in need of a composition that increases the amount of Lysine, Arginine, or Histidine in their diet and providing the subject an effective amount of a dietary supplement, as described herein, for a time sufficient to improve a nutritional imbalance in the subject.

Embodiments also include methods, wherein the nutritional imbalance is a condition associated with a nutritional wasting disease. Embodiments also include methods, wherein the subject has a body mass index (BMI) that is less than that of a healthy subject of the same gender and age. Embodiments also include methods, wherein the amount of Lysine, Arginine, or Histidine is the subject's diet is measured. Embodiments also include methods, wherein the identification step is performed by obtaining a biological sample from the subject, measuring the amount of Lysine, Arginine, or Histidine in the biological sample and comparing the amount of Lysine, Arginine, or Histidine measured in the biological sample from the subject to the amount of Lysine, Arginine, or Histidine present in a biological sample obtained from a second subject.

Embodiments also include methods of using a dietary supplement as described herein to reduce body weight, improve skin or nail health, improve neuromuscular activity, improve sexual desire or reproductive capacity, improve immune system function, improve digestive health, reduce the effects of aging, or improve the ability to break addiction. By some approaches, these methods comprise identifying a subject in need of a composition that increases the amount of Lysine, Arginine, or Histidine in their diet and providing the subject an effective amount of a dietary supplement, as described herein, for a time sufficient to reduce body weight, improve skin or nail health, improve neuromuscular activity, improve sexual desire or reproductive capacity, improve immune system function, improve digestive health, reduce the effects of aging, or improve the ability to break addiction.

Embodiments also include methods, wherein the amount of Lysine, Arginine, or Histidine in the subject's diet is measured. Embodiments also include methods, wherein the identification step is performed by obtaining a biological sample from the subject, measuring the amount of Lysine, Arginine, or Histidine in the biological sample and comparing the amount of Lysine, Arginine, or Histidine measured in the biological sample from the subject to the amount of Lysine, Arginine, or Histidine present in a biological sample obtained from a second subject.

Embodiments also include the use of a mixture comprising at least 5 g of whey protein, egg protein, or soy protein and at least 125 mg of monopeptidic (free-form) Lysine per 16.5 g serving for the preparation of a dietary supplement for the improvement of a condition selected from the group consisting of excess caloric intake, nutritional imbalance, excess bodyweight, reduced skin or nail health, reduced neuromuscular activity, reduced sexual desire, reduced reproductive capacity, reduced immune system function, reduced digestive health, reduced premature aging, and addiction.

Embodiments also include the use above, wherein the mixture comprises at least 250 mg of monopeptidic (free-form) Lysine per 16.5 g serving. Embodiments also include the use above, wherein the mixture comprises at least 500 mg of monopeptidic (free-form) Lysine per 16.5 g serving. Embodiments also include the use above, wherein the mixture comprises at least 750 mg of monopeptidic (free-form) Lysine per 16.5 g serving. Embodiments also include the use above, wherein the mixture further comprises at least 125 mg of monopeptidic (free-form) Arginine per 16.5 g serving. Embodiments also include the use above, wherein the mixture further comprises at least 250 mg of monopeptidic (free-form) Arginine per 16.5 g serving. Embodiments also include the use above, wherein the mixture further comprises at least 500 mg of monopeptidic Arginine per 16.5 g serving. Embodiments also include the use above, wherein the mixture further comprises at least 750 mg of monopeptidic Arginine per 16.5 g serving. Embodiments also include the use above, wherein the mixture further comprises at least 125 mg of monopeptidic (free-form) Histidine per 16.5 g serving. Embodiments also include the use above, wherein the mixture further comprises at least 250 mg of monopeptidic (free-form) Histidine per 16.5 g serving. Embodiments also include the use above, wherein the mixture further comprises at least 500 mg of monopeptidic Histidine per 16.5 g serving. Embodiments also include the use above, wherein the mixture further comprises at least 750 mg of monopeptidic Histidine per 16.5 g serving. Embodiments also include the use above, wherein the dietary supplement is formulated in a powder or liquid form Embodiments also include the use above, wherein the monopeptidic Lysine is formulated for sustained or extended release. Embodiments also include the use above, wherein the monopeptidic Lysine, Arginine, or Histidine is formulated for sustained release, timed-release, or extended release.

Embodiments also include the use of a mixture comprising at least 5 g of whey protein, egg protein, or soy protein and at least 125 mg of monopeptidic (free-form) Lysine per 16.5 g serving for the preparation of a dietary supplement for weight loss.

Embodiments also include the use above, wherein the mixture comprises at least 250 mg of monopeptidic (free-form) Lysine per 16.5 g serving. Embodiments also include the use above, wherein the mixture comprises at least 500 mg of monopeptidic (free-form) Lysine per 16.5 g serving. Embodiments also include the use above, wherein the mixture comprises at least 750 mg of monopeptidic (free-form) Lysine per 16.5 g serving. Embodiments also include the use above, wherein the mixture further comprises at least 125 mg of monopeptidic (free-form) Arginine per 16.5 g serving. Embodiments also include the use above, wherein the mixture further comprises at least 250 mg of monopeptidic (free-form) Arginine per 16.5 g serving. Embodiments also include the use above, wherein the mixture further comprises at least 500 mg of monopeptidic (free-form) Arginine per 16.5 g serving. Embodiments also include the use above, wherein the mixture further comprises at least 750 mg of monopeptidic (free-form) Arginine per 16.5 g serving. Embodiments also include the use above, wherein the mixture further comprises at least 125 mg of monopeptidic (free-form) Histidine per 16.5 g serving. Embodiments also include the use above, wherein the mixture further comprises at least 250 mg of monopeptidic (free-form) Histidine per 16.5 g serving. Embodiments also include the use above, wherein the mixture further comprises at least 500 mg of monopeptidic (free-form) Histidine per 16.5 g serving. Embodiments also include the use above, wherein the mixture further comprises at least 750 mg of monopeptidic (free-form) Histidine per 16.5 g serving. Embodiments also include the use above, wherein the dietary supplement is formulated in a powder or liquid form. Embodiments also include the use above, wherein the monopeptidic Lysine is formulated for sustained release, timed-release, or extended release.

Embodiments also include the use above, wherein the monopeptidic Lysine, Arginine, or Histidine is formulated for sustained release, timed-release, or extended release.

Methods of losing weight are also provided. By some approaches, these methods comprise the steps of providing an embodiment of a dietary supplement, as described herein, to a subject in need thereof for a time sufficient for the subject to lose weight. In some embodiments, the method further comprises identifying the subject as one in need of a composition that elevates the amount of Lysine, Arginine, or Histidine in the subject's diet. Embodiments also include methods, wherein the amount of Lysine, Arginine, or Histidine in the subject's diet is measured. Embodiments also include methods, wherein the subject is identified as one in need of a composition that elevates the amount of Lysine, Arginine, or Histidine in the subject's diet by obtaining a biological sample from the subject, measuring the amount of Lysine, Arginine, or Histidine in the biological sample and comparing the amount of Lysine, Arginine, or Histidine measured in the biological sample from the subject to the amount of Lysine, Arginine, or Histidine present in a biological sample obtained from a second subject.

Aspects also concern a high protein dietary supplement (e.g., a powder, liquid, or food, as described herein) comprising about 5-40 grams of total protein per product serving (e.g., equal to, greater than, at least, or any number in between 5, 10, 15, 20, 25, 30, 35, 40, 45, or 50 grams of total protein/serving) wherein a serving of said composition can be less than, greater than, at least, or any number in between 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams and an effective amount of isolated, purified, or synthetic monopeptidic (e.g., free-form) lysine (e.g., equal to, greater than, at least, or any number in between 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 900 mg, 1000 mg, 1000 mg, 1200 mg, 1300 mg, 1400 mg, 1500 mg, 1600 mg, 1700 mg, 1800 mg, 1900 mg, or 2000 mg per serving) and/or isolated, purified, or synthetic monopeptidic (e.g., free-form) arginine (e.g., equal to, greater than, at least, or any number in between 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 900 mg, 1000 mg 1100 mg, 1200 mg, 1300 mg, 1400 mg, 1500 mg, 1600 mg, 1700 mg, 1800 mg, 1900 mg, or 2000 mg per serving) and/or isolated, purified, or synthetic monopeptidic (e.g., free-form) histidine (e.g., equal to, greater than, at least, or any number in between 10 mg, 50 mg, 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 900 mg, 1000 mg 1100 mg, 1200 mg, 1300 mg, 1400 mg, 1500 mg, 1600 mg, 1700 mg, 1800 mg, 1900 mg, or 2000 mg per serving), which can be provided to a subject in need thereof to improve the general health and welfare of said subject, including, but not limited to, treating, preventing, or ameliorating a disease, malady, or condition related to a nutritional imbalance, in particular a nutritional imbalance that results from a lack of or reduced amount of essential or semi-essential amino acids, in particular positively charged amino acids (e.g., Lysine, Arginine, and Histidine). The composition can optionally comprise other ingredients including, but not limited to, a metabolite, an essential, semi-essential, or non-essential amino acid, an herb, a vitamin, a mineral, a flavoring agent, a coloring agent, a sweetener, a stabilizing agent, or an oil or water soluble antioxidant. In some embodiments, dietary supplements (e.g., powders or liquids, as described herein) can comprise slow, sustained release, time-release, or extended release formulations of an amount of isolated, purified, or synthetic monopeptidic (e.g., free-form) lysine (e.g., equal to, greater than, at least, or any number in between 10 mg, 50 mg, 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg per serving) and/or isolated, purified, or synthetic monopeptidic (e.g., free-form) arginine (e.g., equal to, greater than, at least, or any number in between 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg per serving) and/or isolated, purified, or synthetic monopeptidic (e.g., free-form) histidine (e.g., equal to, greater than, at least, or any number in between 10 mg, 50 mg, 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg per serving) so that an effective amount of Lysine, Arginine, and/or Histidine is delivered to the consumer over an extended time period.

In some embodiments, use of a dietary supplement described herein is coupled with an identification of a subject as one in need of said dietary supplement. That is, in some embodiments, said subject is identified as one in need of said high protein dietary supplement by analyzing a biological sample obtained from said subject (e.g., cheek swab, hair, or body fluid, such as gastric juice, blood, urine, or saliva) for the amount of Lysine, Arginine, and/or Histidine present in said biological sample and comparing said amount with the amount of Lysine, Arginine, and/or Histidine present in a biological sample from a control subject (e.g., an individual in nutritional balance, at a healthy weight and/or body composition and/or an individual that consumes a healthy diet, preferably of the same gender and age), whereby a measurement of an amount of Lysine, Arginine, and/or Histidine in said biological sample obtained from said tested individual that is less than the amount of Lysine, Arginine, and/or Histidine in a biological sample from said control subject identifies said tested subject as one in need of a dietary supplement, as disclosed herein.

Accordingly, some embodiments concern methods for identifying, ameliorating, improving, preventing or treating conditions associated with excess caloric intake, including overweight conditions, obesity and morbid obesity conditions. By some approaches, a subject in need of such intervention is identified as one in need of a composition that ameliorates, improves, prevents, or treats a condition associated with excess caloric intake, such as an overweight condition, obesity, or morbid obesity and said subject is provided a therapeutically effective amount of a high protein dietary supplement (e.g., a powder, liquid, or food, as described herein), wherein said composition comprises about 5 to 40 grams of total protein per serving (e.g., equal to, greater than, at least, or any number in between 1, 2, 5, 10, 15, 20, 25, 30, 35, 40, 45, 50, or 55 grams of total protein/serving), wherein a serving of said composition can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams and an amount of essential or semi-essential amino acids, preferably, a positively charged amino acid, such as an amount of isolated, purified, or synthetic monopeptidic (e.g., free-form) lysine (e.g., equal to, greater than, at least, or any number in between 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg) and/or isolated, purified, or synthetic monopeptidic (e.g., free-form) arginine (e.g., equal to, greater than, at least, or any number in between 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg) and/or isolated, purified, or synthetic monopeptidic (e.g., free-form) histidine (e.g., equal to, greater than, at least, or any number in between 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg) sufficient to increase said subject's metabolic rate or otherwise induce said subject to lose weight. In some of these methods, the Lysine, Arginine, and/or Histidine provided in said dietary supplement is formulated for slow release, time release, sustained release, or extended release so that the consumer is provided a steady state amount of Lysine, Arginine, and/or Histidine over an extended period of time. In some embodiments, the method involves the use of a composition that comprises a metabolite, an herb, a vitamin, an essential, semi-essential, or non-essential amino acid, a mineral, a flavoring agent, a coloring agent, a sweetener, a stabilizing agent, or an oil or water soluble antioxidant.

In some embodiments, said subject is identified as one in need of said high protein dietary supplement by analyzing a biological sample obtained from said subject (e.g., cheek swab, hair, or body fluid, such as gastric juice, blood, urine, or saliva) for the amount of Lysine, Arginine, and/or Histidine present in said biological sample and comparing said amount with the amount of Lysine, Arginine, and/or Histidine present in a biological sample from a control subject (e.g., an individual in nutritional balance, at a healthy weight and/or body composition and/or an individual that consumes a healthy diet), whereby a measurement of an amount of Lysine, Arginine, and/or Histidine in said biological sample obtained from said tested individual that is less than the amount of Lysine, Arginine, and/or Histidine in a biological sample from said control subject identifies said tested subject as one in need of a dietary supplement, as disclosed herein.

In more embodiments, a method for identifying, ameliorating, improving, preventing or treating conditions associated with a nutritional wasting disease in a subject in need thereof is provided. As above, a subject in need of such intervention is identified as one in need of a composition that ameliorates, improves, prevents, or treats a condition associated a nutritional wasting disease and said subject is provided a therapeutically effective amount of a high protein dietary supplement (e.g., a powder, liquid, or food, as described herein), wherein said composition comprises about 5 to 40 grams of total protein per serving (e.g., less than, equal to, greater than, or at least 5, 10, 15, 20, 25, 30, 35, 40, 45, 50 or 55 grams of total protein/serving), wherein a serving of said composition can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams and an amount of essential or semi-essential amino acids, preferably a positively charged amino acid, such as an amount of isolated, purified, or synthetic monopeptidic (e.g., free-form) lysine (e.g., equal to, greater than, at least, or any number in between 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg) and/or isolated, purified, or synthetic monopeptidic (e.g., free-form) arginine (e.g., equal to, greater than, at least, or any number in between 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg) and/or isolated, purified, or synthetic monopeptidic (e.g., free-form) histidine (e.g., equal to, greater than, at least, or any number in between 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg) sufficient to improve a nutritional wasting disease. In some embodiments, the method involves the use of a composition that comprises a metabolite, an herb, a vitamin, an essential, semi-essential, or non-essential amino acid, a mineral, a flavoring agent, a coloring agent, a sweetener, a stabilizing agent, or an oil or water soluble antioxidant. In some of these methods, the Lysine, Arginine, and/or Histidine provided in said dietary supplement is formulated for slow or extended release so that the consumer is provided a steady state of Lysine, Arginine, and/or Histidine over an extended period of time.

In some embodiments, said subject is identified as one in need of said high protein dietary supplement by analyzing a biological sample obtained from said subject (e.g., cheek swab, hair, or body fluid, such as gastric juice, blood, urine, or saliva) for the amount of Lysine, Arginine, and/or Histidine present in said biological sample and comparing said amount with the amount of Lysine, Arginine, and/or Histidine present in a biological sample from a control subject (e.g., an individual in nutritional balance, at a healthy weight and/or body composition and/or an individual that consumes a healthy diet), whereby a measurement of an amount of Lysine, Arginine, and/or Histidine in said biological sample obtained from said tested individual that is less than the amount of Lysine, Arginine, and/or Histidine in a biological sample from said control subject identifies said tested subject as one in need of a dietary supplement, as disclosed herein.

In more embodiments, a method for identifying, ameliorating, improving, preventing or treating conditions associated with a nutritional balance or status of a subject according to gender and age parameters of said subject is provided. As above, a subject in need of such intervention is identified as one in need of a composition that ameliorates, improves, prevents, or treats a condition associated a nutritional imbalance or a unhealthy status of said subject, as compared to subjects of the same gender and similar age, height, and body type, and said subject is provided a therapeutically effective amount of a high protein dietary supplement (e.g., a powder, liquid, or food, as described herein), wherein said composition comprises about 5 to 40 grams of total protein per serving (e.g., less than, equal to, greater than, or at least 5, 10, 15, 20, 25, 30, 35, 40, 45, 50, 55 grams of total protein/serving), wherein a serving of said composition can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams and an amount of essential or semi-essential amino acids, preferably a positively charged amino acid, such as an effective amount of isolated, purified, or synthetic monopeptidic (e.g., free-form) lysine (e.g., equal to, greater than, at least, or any number in between 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg) and/or isolated, purified, or synthetic monopeptidic (e.g., free-form) arginine (e.g., equal to, greater than, at least, or any number in between 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg) and/or isolated, purified, or synthetic monopeptidic (e.g., free-form) histidine (e.g., equal to, greater than, at least, or any number in between 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg) sufficient to improve the nutritional balance or status of said subject. In some embodiments, the method involves the use of a composition that comprises a metabolite, an herb, a vitamin, a mineral, a flavoring agent, a coloring agent, a sweetener, a stabilizing agent, or an oil or water soluble antioxidant. In some of these methods, the Lysine, Arginine, and/or Histidine provided in said dietary supplement is formulated for slow release, timed-release or extended release so that the consumer is provided a steady state of Lysine, Arginine, and/or Histidine over an extended period of time.

In some embodiments, said subject is identified as one in need of said high protein dietary supplement by analyzing a biological sample obtained from said subject (e.g., cheek swab, hair, or body fluid, such as gastric juice, blood, urine, or saliva) for the amount of Lysine, Arginine, and/or Histidine present in said biological sample and comparing said amount with the amount of Lysine, Arginine, and/or Histidine present in a biological sample from a control subject (e.g., an individual in nutritional balance, at a healthy weight and/or body composition and/or an individual that consumes a healthy diet), whereby a measurement of an amount of Lysine, Arginine, and/or Histidine in said biological sample obtained from said tested individual that is less than the amount of Lysine, Arginine, and/or Histidine in a biological sample from said control subject identifies said tested subject as one in need of a dietary supplement, as disclosed herein.

DETAILED DESCRIPTION

Figure 1:
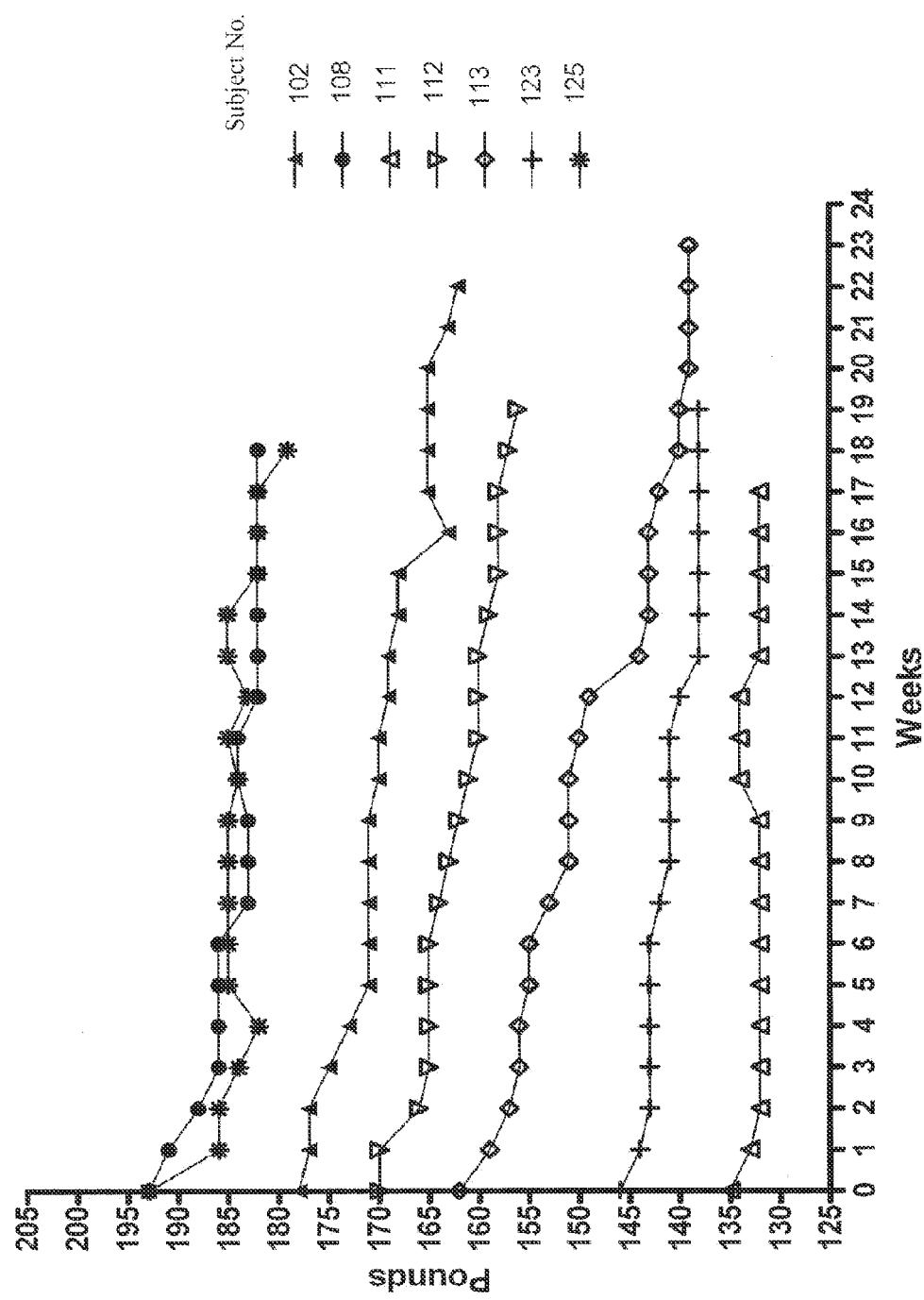
FIG. 1 is a graph of subjects of a weight loss study whose initial weight was between 100 and 200 lbs.

Embodiments described herein provide a high protein therapeutic and/or dietary supplement. A high protein composition described herein can include, but is not limited to, intact or hydrolyzed whey protein, egg protein including egg albumin, lactalbumin, casein, soy protein polypeptides or peptides or amino acids (PPAA) and their derivatives from various biological sources, and may contain additional ingredients, including essential fatty acids, digestive enzymes, ferments (probiotics), lecithin and the like.

These embodiments may contain several essential and semi-essential amino acids with optimal ratios to provide the metabolic "priming", "balancing" and "releasing" factors. As used herein, the terms "priming" or "balancing" means to bring into or maintain in a state of biological and physiological equilibrium. As used herein, the term "releasing" is any number of exogenous or endogenous substances that prevent, correct, neutralize or treat any nutritional disease or imbalance. These include exogenous factors that affect, perturb, and/or correct physiological processes that cause nutritional diseases as well as improve nutritional status in healthy or diseased states. These factors may exert their effects through enabling beneficial nutritional processes, blocking poor nutritional factors and/or releasing endogenous hormones, peptides, proteins, pro-proteins, or digestive enzymes from endocrine or exocrine glands or organs in the body. These releasing factors include, but are not limited to, releasing hormones and/or agents, Starvation Releasing Factors (SRF), Catabolic Releasing Factors (CRF), Obesity Releasing Factors (ORF), Infertility Releasing Factors (IRF), Age Releasing Factors (ARF) and Inflammation Releasing Factors (IRF). The above mentioned factors may be a single or combination of exogenous or endogenous releasing factors and/or hormones and peptides. They are categorized into groups based on treatment protocols or disease symptoms, e.g., starvation, catabolism, obesity, infertility, aging and inflammation.

For example, whey protein comprises a protein fraction obtained from the milk of cows. Milk contains two major protein fractions, including casein, which comprises about 80% of the total protein, and whey protein, which comprises about 20% of the total protein. Whey protein includes several proteins, including, for example, β-lactoglobulin, α-lactoglobulin, immunoglobulins, and lactoferrin (information from Whey Protein Institute web site). Whey protein is more soluble than casein and also has a higher quality rating.

Whey protein is available as "whey protein concentrate", which contains about 29% to 85% whey protein, and "whey protein isolate", which contains 90% or more whey protein and little, if any, fat, cholesterol, or carbohydrates (e.g., Lactose). Regardless of the source of whey protein, the final concentration of whey protein in powder or liquid forms is about 25% to 99%.

Whey protein contains essential and semi-essential amino acids, including cationic amino acids (e.g., Lysine, Arginine, and Histidine) and proteins and, therefore, is a high nutritional quality source of protein. Proteins of high nutritional value may be defined as proteins that contain high concentrations of essential and semi-essential amino acids, including hydrophobic amino acids (Leucine, Isoleucine, Methionine, Phenylalanine, Tryptophan, Valine), hydroxylated amino acids (Threonine) and hydrophilic amino acids that are positively charged (Lysine, Arginine, and Histidine). Whey protein also has a very high biological value, which is a measure of percent assimilation into the body. Since whey protein is available in forms containing little fat and carbohydrates, it can be a particularly valuable source of high-value nutrition for athletes and for individuals with special medical needs (e.g., lactose intolerant individuals), and can be a valuable component of diet programs. Further, whey protein contains biologically active proteins such as immunoglobulins and lactoferrin and, therefore, provides advantages over other protein sources such as soy protein. Whey protein also has a fresh, neutral taste and, therefore, can be included in other foods without adversely affecting the taste.

Egg protein also contains essential and semi-essential amino acids, including cationic (basic) amino acids and proteins and, therefore, is a high nutritional quality source of protein. Egg protein also has a very high biological value, and thus may be found in various embodiments of high protein compositions and dietary supplements.

Some embodiments of the high protein compositions described herein are dietary supplements. A dietary supplement can comprise an amount of protein, which can be at least, greater than, equal to, or any number in between 5%, 10%, 15%, 20%, 25%, 30%, 35%, 40%, 45%, 50%, 55%, 60%, 65%, 70%, 75%, 80%, 85%, 90%, 95%, 96%, 97% 98%, 99% or 100% w/w or w/v protein). A serving of the supplement can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. That is, in some embodiments the amount of protein in a dietary supplement (e.g., an amount of whey protein, soy protein, or egg protein, with or without supplementation with free-form monopeptidic amino acids, such as Lysine, Arginine, and/or Histidine) in the dietary supplement can be, for example, less than, greater than, at least, or any number in between 5%, 10%, 15%, 20%, 25%, 30%, 35%, 40%, 45%, 50%, 55%, 60%, 65%, 70%, 75%, 80%, 85%, 90%, 95%, 96%, 97% 98%, 99% or 100% w/w or w/v of dietary supplement. In some embodiments, the amount of free-form monopeptidic Lysine, Arginine, and/or Histidine, and/or monopeptidic Lysine, Arginine, and/or Histidine formulated for delayed release, slow release, extended release, or time release can be for example, less than, greater than, at least, or any number in between 0.5%, 0.6%, 0.7%, 0.75%, 0.8%, 0.9%, 1.0%, 2%, 3%, 4%, 5%, 6%, 7%, 8%, 9%, 10%, 11%, 12%, 13%, 14%, 15%, 16%, 17%, 18%, 19%, or 20% w/w or w/v of dietary supplement.

In some embodiments, a dietary supplement or high protein therapeutic supplement comprises a powder that comprises a first amino acid complex, a second amino acid complex and a protein complex. The first amino acid complex comprises at least one amino acid selected from the group comprising L-Lysine and L-Arginine. The second amino acid complex comprises at least one amino acid selected from the group comprising L-Isoleucine, L-Leucine, L-Threonine, L-Valine, dl-Phenylalanine (or L-Phenylalanine), L-Methionine, L-Histidine, 5-Hydroxy Tryptophan (or L-Hydroxy Tryptophan or L-Tryptophan). The protein complex comprises at least one protein source selected from the group comprising whey protein isolate, whey protein concentrate and soy protein isolate. In some embodiments, the dietary supplement also comprises other ingredients including guar gum, lecithin, natural and artificial flavors, natural and artificial colors, fructo-oligosaccharide, natural and artificial sweeteners.

In some embodiments, a dietary supplement is manufactured by mixing a combination of whey protein isolate, whey protein concentrate and soy protein isolate. A first amino acid complex and a second amino acid complex are provided. The first amino acid complex comprises at least one amino acid selected from the group comprising L-Lysine and L-Arginine. The second amino acid complex comprises at least one amino acid selected from the group comprising L-Isoleucine, L-Leucine, L-Threonine, L-Valine, dl-Phenylalanine (or L-Phenylalanine), L-Methionine, L-Histidine, 5-Hydroxy Tryptophan (or L-Hydroxy Tryptophan or L-Tryptophan). In some embodiments the first amino acid complex comprises L-Lysine and L-Arginine and the second amino acid complex comprises L-Isoleucine, L-Leucine, L-Threonine, L-Valine, dl-Phenylalanine (or L-Phenylalanine), L-Methionine, L-Histidine, 5-Hydroxy Tryptophan (or L-Hydroxy Tryptophan or L-Tryptophan). In some embodiments other ingredients are provided. In some embodiments, the other ingredients comprise guar gum, lecithin, natural and artificial flavors, natural and artificial colors, fructo-oligosaccharide, natural and artificial sweeteners.

In some embodiments, the dietary supplement or high protein therapeutic supplement is provided at least once, twice or three times a day for a set period, which can be at least, less than, greater than, equal to, or any number in between 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, equal to, or any number in between 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, equal to, or any number in between 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months.

High protein therapeutic supplements and dietary supplements also may include one or more nutrients such as vitamins (e.g., vitamin A, vitamin C, vitamin E, B complex vitamins, Lutein and the like), minerals (calcium, magnesium, phosphorus and the like) and/or trace metals (e.g., zinc, copper, chromium, iron and the like); and/or can contain one or more herbs or extracts thereof ("herbal supplements"). Herbal supplements can include, but are not limited to, the following ingredients or any combination thereof.

Calcitum (Calcite)
Veronica ciliate (Speedwell)
Punica granatum (Pomegranate)
Elletaria cardamomum (Smaller cardamom)
Holarrhena antidysenterica (Coneru)
Saussurea lappa (Costus root)
Terminalia chebula (Chebulic myrobalan)
Piper nigrum (Black pepper)
Herpetospermum caudgerum (Balsam apple)
Inula racemosa (Elecampane)
Saxifraga pasumensis (Saxifrage)
Pterocarpus santalinus (Red sandalwood)
Mineral exudate (Shilajit)
Emblica officinalis (Emblic myrobalan)
Hippophae rhamnoides (Sea Buckthorn)
Coriandrum sativum (Coriander)
Angelica archangelica (Angelica)
Piper longum (Long pepper)
Tribulus terrestris (Small caltrops)
Crocus sativus (Saffron)
Mirabilis himalaica (Himalayan mirabilis)
Myristica Fragrans (Nutmeg)
Shorea robusta (White sal tree resin)
Aquilaria agallocha (Eaglewood)
Ferula jaeschkeana (Asofoetida)
Santalum album (White sandalwood)
Spondias axillaris (Hog plum)
Acacia catechu (Catechu tree)
Allium sativum (Garlic)
Cinnamomum zeylanicum (Cinnamon)
Asparagus racemosa (Asparagus)
Polygonatum cirrhifolium (Solomon's seal)
Carthamus Tinctorius (Safflower)
Terminalia belerica (Beleric myrobalan)
Cassia tora I. (Foetid cassia)
Adhatoda vasica (Malabar nut tree)
Acorus gramineus (Sweetflag)
Commiphora mukul (Guggul)
Gentiana algida (White gentian)
Glycyrrhiza glabra (Licorice)
Bambusa Textilis (Bamboo pith)
Cochlearia scapiflora (White sedum)
Amomum subulatum (Greater cardamom)

Hedychium spicatum (Ginger lily)
Rhododendron sp. (Rhododendron)
Raphanus sativus. (Young radish)
Symplocos crataegoides (Lodh tree)
Juniperus pseudo-sabina (Central asian juniper)
Picrorrhiza kurroa (Picrorrhiza grass)
Areca catechu (Betel nut)
Mucuna prurita (Mucuna pruriens)
Cesalpinia bonducella (Bonducella nut)
Eugenia jambolana (Blackberry)
Thlaspi arvense I. (Pennycress)
Nardostachys jatamansi (Valerian)
Mesua ferrea (Ironwood tree)
Malva silvestris (Marshmallow)
Momordica charantia (Bitter gourd)
Vitis vinifera (Grape vine)
Arenaria glanduligera (White arenaria)
Picrorrhiza kurroa (Picrorrhiza grass)
Orchis latifolia (Salep orchid)
Rhodiola sp. (Rhodiola)
Carum carvi (Black cumin)

Other herbal and biological supplements including, but not limited to antioxidants, including bee pollen, Royal Jelly and bee propolis, numerous antioxidants taken from botanical sources, including ginseng, gingko biloba and saw palmetto are also envisaged. Also, supplements such as metabolic enhancers, sleep enhancers, fertility enhancers and the like are also contemplated. Powder or liquid beverage products can contain a flavoring agent (e.g., an agent providing a fruit flavor, a cola flavor, or a chocolate or vanilla flavor), a sweetener (e.g., a natural or synthetic sugar such as sucrose, sucralose, aspartame, and/or acesulfame potassium), a coloring agent, or an agent such as citric acid and/or malic acid, which provides tartness.

In addition, the high protein composition, may include, but is not limited to, a sweetener, a flavoring agent, a coloring agent, or a combination thereof, or such agents can be added at or about the time the liquid is added to the powder mixture. Similarly, one or more nutrients and/or herbal supplements can be admixed with the liquid (i.e., prior to the pasteurization), or can be added at or about the time the liquid is added.

Additional components can be added to the high protein composition described herein including, for example, one or more therapeutic and/or herbal supplements, analgesics (e.g., aspirin, antidepressants, pain reducers, and the like), mild stimulants (e.g., caffeine, chocolate and the like) or relaxants, flavorings, and the like (see, e.g., U.S. Pat. No. 6,403,129 and U.S. Pat. No. 6,261,589, hereby expressly incorporated by reference in their entireties).

Still, one aspect provides various factors which activities promote positive feedback, priming factors, balancing factors, correction factors and equilibrium factors. For example, Trophic Balancing Factor(s) (TBF), Metabolic Priming Factor(s) (MPF), Catabolic Releasing Factor(s) (CRF), Therapeutic Correcting Factor(s) (NCF), Obesity Releasing Factor(s) (ORF), Fat Releasing Factor(s) (FRF), Weight Loss Factor(s) (WLF), Cellular Health Factor(s) (CHF), Molecular Health Factor(s) (NMF), Organ Health Factor(s) (OHF), Sensory Health Factor(s) (SHF) and the like. Again, these factors may be single or a combination of existing hormones, peptides, amino acids and/or proteins, so long as they have a cumulative and/or synergistic effect and provide the desired nutritional effects.

In general, the high protein supplement described herein seeks to maximize protein and/or amino acid content, while at the same time, minimize fat and carbohydrate content (e.g., particularly for individuals suffering from temporal, temporary or transient protein deficiency that leads to excess caloric intake from too many carbohydrates and/or fats and are overweight, obese or morbidly obese, as well as weight-loss conditions and diseases marked by insufficient caloric intake). Further discussions of protein deficiency are in Schick, J., Verspohl, R., Kern, H. and Scheele, G. (1984) Two distinct genetic patterns of response in the exocrine pancreas to inverse changes in protein and carbohydrate in the diet, Am. J. Physiol. 248: G611-616; Scheele, G. (1985) Regulation of gene expression in the exocrine pancreas, In The Exocrine Pancreas: Biology, Pathobiology and Diseases (V. L. Go, J. D. Gardner, F. P., Brooks, E. Lebenthal, E. P. DiMagno, G. A. Scheele, eds.) Raven Press, New York, N.Y., pp 55-67; and Scheele, G. (1993) Regulation of pancreatic gene expression in response to hormones and nutritional substrates, In The Pancreas, Biology, Pathobiology and Diseases (V. L. Go, J. D. Gardiner, H. A. Reber, E. Lebenthal, E. P. DiMagno, G. A. Scheele, eds.) Raven Press, New York, N.Y. pp 103-120, each is incorporated by reference in their entireties.

Temporal protein deficiency occurs in response to long periods of inadequate protein (PPAA) intake, comprising up to three quarters (up to 18 hours) of the diurnal rhythm (24 hour day), which remains uncorrected over long periods of time (months to years to decades). Temporal protein deficiency occurs in both nutritional wasting diseases and caloric excess diseases. Because (i) protein is the sole food source that contains nitrogen and (ii) cellular protein turnover occurs on the time scale of minutes to hours to days, chronic temporal protein deficiency leads to cellular catabolic states that cause nutritional stress. Catabolic states occurring on a daily prolonged basis lead to chronic fatigue and sluggish behavior. Catabolic states also lead to "famished states" whereby increases in appetite lead to food cravings. In general obese individuals satisfy these famished states by eating low nutritional value foods (high carbohydrate and fat content) that enrich the body's fat depots under sedentary conditions. In contrast, individuals with wasting diseases respond minimally to the famished states and continue to avoid food consumption.

The body's cells respond to catabolic states by activating lysosomes, cellular digestive organelles. In order to maintain minimal blood levels of amino acids, particularly essential and semi-essential amino acids, activated lysosomes utilize a process called "autophagy" or "endophagy" to internalize portions of the cytosol and digest their contents. Pollard, T. D. and W. C. Earnshaw (2004) Degradation of Cellular Components, Chapter 24, in "Cell Biology", Elsevier, Inc. pp 369-380. Cellular digestion of cytosolic components, enriched in cellular proteins, allows the cell to expand the amino acid pool throughout the body. In addition, activated lysosomes may also engage in secretory events at the cellular plasma membrane and thereby secrete digestive enzymes and acidic contents into extracellular compartments where further digestive events may occur. Pollard et al. further state that autophagy, or the process of formation and degradation of autophagic vacuoles in liver, requires less than about 15 minutes.

Digestion of extracellular proteins in skin, internal organs, joints, muscles, cardiovascular system and central nervous system, including the brain ("Exophagy"), can lead to pain, impairment of organ function and accelerated aging.

The body's response to catabolic states also includes significant perturbations in gene and protein expression, which leads cells to adapt to transient or temporal starvation patterns. For example, in the presence of an adequate intake of dietary protein, adequate quantities of amino acids result in gene and protein expression patterns that support healthy metabolic processes and allow cells to adapt to physiological changes in the environment (changes in temperature, air mixture and food substrates in the environment). Under conditions of temporal protein deficiency when protein intake and amino acid levels in the blood stream are diminished and limiting, and therefore inadequate, gene and protein expression patterns change to support starvation processes at the expense of health processes. For example it has been shown that protein deficiency in the exocrine pancreas leads to dramatic changes in gene and protein expression. Under these conditions, syntheses of neutral and cationic (positively charged) digestive enzymes are dramatically decreased by 95% or more. A small group of anionic (negatively charged) digestive enzymes were expressed at the expense of a much larger group of neutral and cationic enzymes. The persistence in synthesis of anionic proteases allows for the digestion of newly found sources of protein, a process that is necessary, at this point, for survival of the organism. However, the loss of synthesis of neutral and cationic enzymes significantly impaired the ability of the body to support healthy functions, including efficient digestion of carbohydrate and fat. Accordingly, it is contemplated that the amino acids Lysine, Arginine, and Histidine are rapidly depleted by the body under certain conditions and since the body is unable to synthesize these amino acids, the body is faced with a roadblock to good health. That is, once the Lysine, Arginine, and Histidine stores are depleted, (e.g., in periods of starvation or poor diet) the body is unable to manufacture enzymes required for proper body function and the system shuts down resulting in storage of fat and, in some cases, catabolic destruction of muscle and the disease states or conditions described herein. Thus, it is contemplated that restoration of health and proper body function can be mediated by maintaining a diet and/or supplementing ones diet with Lysine, Arginine, and Histidine. It is important to note that very little monopeptidic or free-form Lysine, Arginine, and/or Histidine exists naturally in the diet and that the body has to break-down proteins in order to obtain these vital amino acids. By providing a dietary supplement prepared as described herein the body is provided an amount of free-form or monopeptidic Lysine, Arginine, and/or Histidine to rapidly restore proper balance and enzyme function and the body is provided an amount of extended release Lysine, Arginine, and/or Histidine (e.g., Lysine, Arginine, or Histidine present in protein or polypeptides or monopeptidic or free-form Lysine, Arginine, and/or Histidine formulated with coatings, as described herein, to provide extended release or time released Lysine, Arginine, and/or Histidine. That is, some aspects of the embodiments described herein provide a subject with an immediate bolus of monopeptidic Lysine, Arginine, and/or Histidine, which can be rapidly assimilated and an extended release formulation of lysine (vis a vis polypeptides that contain Lysine, Arginine, and/or Histidine and/or coated or protected formulations of extended release monopeptidic lysine) so that a constant level of Lysine, Arginine, and/or Histidine can be maintained in the body.

The compositions and methods described herein, can be customized and tailored to meet the needs of the subject. For example, those individuals that are overweight or obese and suffer from excess caloric diseases, need to increase the amount of protein and amino acids and dramatically reduce the amount of carbohydrate (starch and sugars) and fat (triglycerides); whereas, normal individuals seeking to maintain minimal weight within the normal range need to increase protein and amino acids while moderating carbohydrate and fat.

Further, the compositions and methods described herein can be customized to modify certain elements of the compositions, e.g., acidic peptides or proteins, into basic peptides or proteins. By modifying acidic proteins to basic proteins, it is contemplated that they will have increased biological value. Modifications such as conservative amino acid substitutions include the replacement of one amino acid residue with another amino acid residue having relatively the same chemical characteristics, for example, the substitution of one hydrophobic residue such as isoleucine, valine, leucine or methionine for another, or the substitution of one polar residue for another, for example, substitution of arginine for lysine; or of glutamic for aspartic acid; or of glutamine for asparagine, or the like.

Further, longer peptides can be produced by the "native chemical" ligation technique which links together peptides (Dawson et al., Science 266:776, 1994, which is incorporated herein by reference). Variants can be created by recombinant techniques employing genomic or cDNA cloning methods. Site specific and region directed mutagenesis techniques can be employed (Ausubel et al., supra, 1989 and 1990 to 1993 supplements), see volume 1, chapter 8; Protein Engineering (Oxender and Fox eds., A. Liss, Inc., 1987)). In addition, linker scanning and PCR mediated techniques can be employed for mutagenesis (Erlich, PCR Technology (Stockton Press 1989); Ausubel et al., supra, 1989 to 1993). Protein sequencing, structure and modeling approaches for use with any of the above techniques are disclosed in the above cited references.

Transgenic animals are encompassed by the present disclosure. For example, transgenic cows or breeds of cattle can be made wherein the animals have higher value milk, e.g., increased essential and semi-essential amino acids. Various methods are known for producing a transgenic animal. In one method, an embryo at the pronuclear stage (a "one cell embryo") is harvested from a female and the transgene is microinjected into the embryo, in which case the transgene will be chromosomally integrated into the germ cells and somatic cells of the resulting mature animal. In another method, embryonic stem cells are isolated and the transgene is incorporated into the stem cells by electroporation, plasmid transfection or microinjection; the stem cells are then reintroduced into the embryo, where they colonize and contribute to the germ line. Methods for microinjection of polynucleotides into mammalian species are described, for example, in U.S. Pat. No. 4,873,191, which is incorporated herein by reference. In yet another method, embryonic cells are infected with a retrovirus containing the transgene, whereby the germ cells of the embryo have the transgene chromosomally integrated therein.

Non human transgenic animals can be bovine, porcine, ovine, avian, sheep, goats, and other animals, as well as other vertebrates, and includes transgenic invertebrates. The transgene can be introduced into embryonic target cells at various developmental stages, and different methods are selected depending on the stage of development of the embryonic target cell. The zygote is the best target for microinjection. The use of zygotes as a target for gene transfer has a major advantage in that the injected DNA can incorporate into the host gene before the first cleavage (Brinster et al., Proc. Natl. Acad. Sci., USA 82:4438 4442, 1985). As a consequence, all cells of the transgenic non human animal carry the incorporated transgene, thus contributing to efficient transmission of the transgene to offspring of the founder, since 50% of the germ cells will harbor the transgene. Such methods of modifying the expression of proteins in an organism include plants, e.g., tobacco plants, seaweed and the like.

Generally, a peptide as described herein contains at least about six amino acids, usually contains about ten amino acids, and can contain fifteen or more amino acids, particularly twenty or more amino acids. It should be recognized that the term "peptide" is not used herein to suggest a particular size or number of amino acids comprising the molecule, and that a peptide of the present disclosure can contain up to several hundred amino acid residues or more.

Some embodiments also provide methods for improving, ameliorating, treating, or preventing a nutritional wasting disease as well as a disease caused by excessive caloric intake (e.g., overweight conditions, obesity, morbid obesity, Syndrome X [Metabolic Syndrome], Type II Diabetes with insulin resistance) by administering or providing a therapeutically effective amount of high protein therapeutic or dietary supplement, as described herein. Nutritional wasting diseases include, but are not limited to, Chronic Fatigue Syndrome, Fibromyalgia, Anorexia Nervosa, and other related disorders.

Chronic fatigue syndrome (CFS) is a disorder which, until recently, has received no formalized name, received little attention and was believed by the majority of the medical community to be a psychological rather than medical disorder. Chronic fatigue syndrome is a puzzling, exasperating illness whereby previously healthy, vigorous and productive young or middle-aged adults are suddenly afflicted with a persistent, overwhelming fatigue and/or malaise. Often those suffering from CFS also have muscle weakness and pain and swelling of the lymph nodes. When such a severe debilitating fatigue extends beyond six months and psychiatric disease is excluded, the condition has been termed "chronic fatigue syndrome." Despite the number of people afflicted with chronic fatigue syndrome and the recent research attention, to date, the cause of the disorder remains unknown. Recently, in the Journal of the Royal Society of Medicine, Vol. 84, February, 1991, chronic fatigue syndrome is defined as: "A fatigue which is the principal symptom, which has a definite onset, and is severe, disabling and affects both physical and mental functioning, and furthermore that fatigue should have been present for a minimum of six months at which it was present for more than 50% of the time."

One or more of the following symptoms are generally associated with the syndrome, including, but not limited to, sleep disturbances (changes in the duration of sleep and/or quality of sleep, e.g., hypersomnia or increased sleep, insomnia or reduced sleep, decrease of REM sleep and the like), impairments in concentration and short-term memory, chronic and recurrent low-grade fever, and musculoskeletal pain. There is also a lack of ability to perform an activity in the manner or within the range considered normal for a healthy human being. These symptoms also result in loss of psychological or physiological functions. Mood disturbances such as depressed mood, and anhedonia, anxious mood, emotional instability, irritability, and severity of the mood disturbances should be assessed on standards scales. In addition to the physical pain associated with this disorder, there is also a severe mental and emotional toll placed on the CFS sufferer. As a result of the prolonged and debilitating fatigue, and flu-like symptoms, CFS sufferers are forced to reduce their level of activity, and are often unable to lead what would be considered a normal life. A variety of treatments have been suggested and utilized for the treatment of chronic fatigue syndrome, however, all treatments to date do not restore balance in the subjects suffering from CFS. In a small group of patients studied by the inventor, it has been shown that CFS is one of the wasting nutritional diseases associated with recurrent and prolonged catabolic states. The compositions described herein can be used to improve, ameliorate, prevent, or treat CFS or a condition associated with CFS.

Fibromyalgia (FM) is a widespread rheumatic condition which is characterized by chronic pain in fibrous tissues such as muscles, joints and connective tissues, easy fatigability, multiple tender points, abnormal sleep patterns, stiffness, headaches, irritable bowels numbness and other symptoms. It is also associated with chronic fatigue syndrome. The cause of fibromyalgia is unknown and there are no known cures. Various medications are used to treat fibromyalgia, as well as hypnosis, but there are no known medications which permanently relieve its symptoms. It was determined that FM is one of the wasting nutritional diseases associated with recurrent and prolonged catabolic states. The compositions described herein can be used to improve, ameliorate, prevent, or treat FM or a condition associated with FM.

Syndrome X is a syndrome characterized by insulin resistance, leading to hyperinsulinaemia, dyslipidemia and impaired glucose tolerance, which can progress to non-insulin dependent diabetes mellitus (Type II diabetes), characterized by hyperglycemia, and which then further progresses to diabetic complications. As further described herein, Syndrome X and related diabetic diseases are tied into diseases stemming from excess caloric intake e.g., obesity, Type II diabetes and the like. The compositions described herein can be used to improve, ameliorate, prevent, or treat various symptoms associated with Syndrome X and/or diabetes.

A clinical trial conducted by the University of Minnesota, recently approved by the Food and Drug Administration and published in abstract form has demonstrated that one of the commercial derivatives of Whey protein, instantized and hydrolyzed (BIOZATE® manufactured by Davisco Foods International, Inc., in Le Sueur, Minn.), beneficially reduced diastolic and systolic blood pressure, reduced total and LDL cholesterol and reduced C-Reactive Protein, a non-specific marker of inflammation.

The compositions and methods described herein do not provide regimens only intended for those individuals desiring to build up muscle mass and provide increased body tone (or "toning"); nor is the disclosure intended only for improved or enhanced athletic or physical performance. Thus, the compositions and the methods of the disclosure herein described are for the purposes of alleviating, ameliorating, or improving various diseases or disease states or conditions associated with temporal protein deficiency and catabolic states, for example, nutritional wasting diseases and diseases due to excess caloric intake, as will be discussed in more detail below.

A "therapeutic composition" as used herein can consist of an admixture with an organic or inorganic carrier or excipient, and can be compounded, for example, with the usual non-toxic, pharmaceutically acceptable carriers for powders tablets, pellets, capsules, suppositories, solutions, emulsions, suspensions, or other forms suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, short-chain fatty acids, medium chain length triglycerides, dextrans, oligofructans and other carriers suitable for use in manufacturing preparations, in solid, semisolid, or liquid form. In addition, auxiliary stabilizing, thickening or coloring agents can be used, for example as stabilizing and drying agents, such as triulose.

As used herein, "effective amount" refers to the minimal amount of a substance or agent, which is sufficient to achieve a desired therapeutic effect. Therefore, when used in connection with a powder or cold-stable liquid formulation or composition, effective amount is an amount of such agent, which is sufficient to achieve a desired protein, peptide or amino acid (PPAA) plasma level. Such plasma levels may be achieved within and sustained for various time intervals as determined by the parameters of each particular formulation. The type and amount of protein, peptide and amino acid mix, the type and amount of inert carrier, the size of the transdermal or transmucosal formulation, as well as the presence and amount of specific penetration enhancers may all be adjusted to arrive at a formulation which achieves the desired blood levels within a specific time interval. One of ordinary skill in the transdermal or transmucosal arts would be able to readily determine the amount and type of each component in the combination, which are required to achieve the target blood levels within a specified time frame.

Yet, in more embodiments, methods are provided for improving, ameliorating, preventing, or treating diseases or symptoms or conditions associated therewith brought on or resulting from or compounded by excess caloric intake. The food industry has created a taste trap. Taste buds evolved to promote food intake, not to inhibit food intake. Processed foods, manufactured by the Food Industry, are rich in carbohydrates and fats, and restaurants serve huge proportions of food and wine to increase revenues. High intake of carbohydrate and fat lead to significant increases in fat stores in a sedentary culture. The nutritional balancing problem is compounded by sleeping because the body goes into a fasting period during sleeping hours, and fasting leads to temporal protein deficiency with low levels of amino acids in the blood circulation. Yet, food intake prior to sleep is prevented by the ingestion of bulk foods that lead to indigestion, postural gastroesophageal insufficiency, hiatus hernia, gastroesophageal reflux syndrome (GERD) and Barrett's Syndrome, leading to esophageal cancer.

Hence, members of advanced sedentary cultures fall into a nutritional balance trap, whereby it is difficult to balance the intake of protein, carbohydrate and fat with the body's ability to metabolize (burn) the ingested calories. The trap is widened by sedentary lifestyles and further widened by the onset of prolonged temporal protein deficiency, which leads to catabolic states, food cravings and eating binges. For example, while protein intake needs to be increased, carbohydrate intake needs to be moderated and nonessential fat (triglycerides) needs to be minimized without restraint. Thus, protein intake at 4 calories per gram, providing the only source of nitrogen, needs to be supplemented by Nutritional supplements described herein. Carbohydrate at 4 calories per gram needs to be greatly moderated and nonessential fat at 9 calories per gram needs to be avoided. All foods, whether from animal, fish or plant sources contain protein, carbohydrates and fats (plant foods and fish are somewhat more nutritious than animal foods in that they contain less cholesterol and nonessential fat). Thus, increasing protein intake with natural foods means that all three food substrates must, by necessity, increase. Processed foods raise the ratio of carbohydrates & nonessential fats to protein. "Fast" foods raise the ratio even further and maximize the nutritional balance trap.

Further, nutritional studies have been performed varying protein, carbohydrate and fat in the diet. Under conditions of low protein (temporal protein deficiency) and correspondingly high carbohydrate levels, paradoxical changes were observed. Although protein substrates in the diet were low, and total protein synthesis rates were significantly decreased, a corresponding decrease in proteases was not observed. Although carbohydrates levels in the diet were high, a corresponding increase in glycosidases was not observed. These results demonstrate that protein deficiency leads to catabolic (starvation) patterns of protein expression at the expense of healthy protein expression patterns.

Positioning organisms for nutritional balance and health, catabolic states, including "autophagy", "exophagy" and "starvation expression patterns" must first be shut down. These perturbations cannot be shut down without adequate protein in the diet. Few studies have been conducted on protein deficiency in humans. The following table provides estimates in changes in human food consumption over the past 500 years (Table 1).

TABLE 1

CHANGES IN FOOD INTAKE OVER THE PAST 500 YEARS

|  | 1500 | 1900 | 2000 |
|---|---|---|---|
| Food Intake (calories) | 2400 | 2400 | 2400 |
| Protein | 30% | 30% | 10-15% |
| Carbohydrates | 40% | 40% | 55-60% |
| Fats | 30% | 30% | 30-35% |
| Eating Frequency (per day) | 3-4x | 3-4x | 1.5x |
| Active physical work | 100% | 90% | 10% |
| Life Span (years) | 44 | 48 | 72 |

Thus, drastic changes have occurred in food intake and nutritional status over the past 100 years. Current data collected in the United States shows that 90% of people live sedentary lives, deficient in exercise; greater than 60% are overweight, 22.7% are obese, both groups unable to balance caloric intake with caloric metabolism, approximately 33% maintain fitness through significant caloric deprivation and/or exercise and approximately 5% demonstrate nutritional wasting diseases. Given that processed foods in the grocery store contain unnecessarily high carbohydrate and fat content, it is necessary for many people to significantly restrict food intake to maintain normal weight. This usually occurs by restricting protein intake to a much greater extent than carbohydrate or fat intake. These individuals may be protein deficient up to 18 hours a day. Approximately 33% are able to approach metabolic balance, which usually requires serious commitments to exercise. Thus, over the years, sedentary Americans have acquired various eating disorders including consuming too many fast foods, which demonstrate high carbohydrate and fat levels, including toxic trans fats; too many snacks, which have poor nutritional value; too much coffee, which can irritate the digestive tract; irregularly scheduled meals; and drinking too much sugar water, e.g., soft drinks or fruit juices.

In particular, the compositions herein can be used as a treatment, or part of a treatment, to ameliorate various eating disorders in men and women. For example, in women, diseases including but not limited to, Chronic Fatigue Syndrome, Fibromyalgia and Anorexia Nervosa, the composition described herein will decrease catabolic states associated with these diseases and preserve body health without adding excessive weight to the body. Because the compositions herein preserve body health, other eating disorders in women can be treated with the compositions described herein e.g., women going through maturational and nutritional changes during puberty and teenage development, cyclical menstrual weight changes during reproductive years (20 s, 30 s, 40 s, 50 s) and weight changes associated with menopausal and post-menopausal changes.

Men also have various eating disorders, including, but not limited to, weight gain associated with sedentary activities, including build-up of visceral fat in the abdomen (stomach "paunch"), and generally to maintain body health during extreme sports. Thus, with age, individuals, including men and women tend to restrict the food that they eat, wishing to limit the number of calories that they consume and the weight that they gain. However, severe restriction of food leads to temporal protein deficiency and catabolic activities during the night and often extending through breakfast and lunch. An example of this relates to models in the fashion industry, who endure extreme fasting behavior in order to maintain figures that are slim and trim.

In another aspect, compositions described herein can be used to treat obesity and or obesity related diseases, including diabetes, e.g., diabetes mellitus type II or adult onset diabetes. A regular regimen of therapeutically effective amounts of the composition herein, can reduce stomach size, foster portion control, provide satiety (feeling of fullness) without excess calories (1 tbsp=50-100 calories), minimize intake of carbohydrate and fat, avoid stringent restrictions in diet as long as food intake is moderate, provide snacks without high calorie intake and optimize balance in therapeutic substrates (protein, carbohydrate and fat) without food withdrawal defects. With regards to diabetes in particular, therapeutically effective amounts of the composition can minimize intake of carbohydrate and fat, provide weight control, minimize insulin insensitivity and hyperglycemia, and reduce protein-glycation, free radical formation and inflammation.

Further, in another embodiment, the high protein supplements and admixtures may be packaged in carbonated or non-carbonated beverages. The beverage can further include aseptically dispensing some or all of the beverage into a container (e.g., a storage vessel, a glass bottle, a plastic bottle, and/or a can). For example, the supplement of the present disclosure can be admixed to a smoothie drink. As used herein, the term "smoothie" or "shake" or any equivalent thereof, means a thick beverage of protein pureed in a blender with some combination of fruit, milk, soymilk, yoghurt, juice, and/or ice. Examples, of shakes include, but are not limited to, Smoothie Health Shakes, Longevity Shakes, Fertility Shakes, Fitness Shakes, Body Building Shake, Performance Shakes, Skin Care Shakes, Beauty Shakes, Joint Care Shakes, Memory Shakes, Nutrition Shakes, Eyesight Shakes, Sleep Shakes, Weight Loss Shakes, Herbal Shakes, Marine supplement shakes (Blue-green algae: *Chlorella*; Spirulina), Antioxidant Shakes, Vitamin & Mineral Shakes, Probiotic shakes and the like.

The compositions described herein can also be packaged and sold in, for example, vending machines which would provide for a presence and access in public and private schools, military complexes, nursing homes, hospitals and other venues for patients that suffer from hyper and hypocaloric diseases and disorders. The compositions described herein can also be packaged as "pour and blend", "pour and stir" or premixed liquids with soda pop, colas, soft drinks and non alcoholic, low alcohol, high alcohol and coffee mixtures that may be served in private and public institutions, including restaurants, bars, "pubs", "Gast-Hauses", coffee-houses and the like around the world.

The composition of the present disclosure can also be packaged in candies, therapeutic candy bars and candy supplements that may be carried in pockets, purses or bags, including Breakfast, Lunch and Dinner bags as well as snack bags, high-protein, low calorie "ice creams" and "alternative ice creams", liquid drinks and liquid meals in medical institutions, nursing homes, military establishments, public and private schools, kiosks, catered events, "hot-dog" stands and other food- and drink-vending purveyors at sporting events, entertainment events, political events, public interest events, religious events, half-way houses, food lines, short- and long-term care facilities, hospitals and the like. The powder or liquid products may also be sold as part of network marketing and franchise businesses around the world.

In one aspect of the present disclosure, different routes of administration are contemplated, which will be customized to meet the needs of the subjects in need, including, but not limited to, oral, transmucosal, transdermal, subcutaneous and intravenous. For purposes of this description, transmucosal routes of administration are understood to include intranasal, ocular, optic, oral cavity (buccal cell, sublingual, and laryngeal administration) and transdermal administration. As used herein, "transdermal delivery formulation," or "transdermal formulation" or "transdermal composition" or "transdermal solution" refers to any protein, peptide and/or amino acid compositions containing device, system, product, chemical combination, or mechanism capable of being applied to, or against the skin, to affect transdermal delivery of the protein or peptide formulation. Also, as used herein, the term "skin" refers to any membrane of the human body to which a chemical formulation, for example, a cold-stable formulation, or composition may be applied including the external skin of the body, the mucosa membranes of the nasal, oral, optic, vaginal, and rectal cavities.

Also, as used herein, the term "transdermal" or "percutaneous" delivery means delivery of a substance or agent, for example, a protein, peptide or amino acid mixture, by passage into and through the skin. Hence the terms "transdermal" and "transmucosal" are used interchangeably unless specifically stated otherwise. Likewise, the terms "skin", "derma", "epidermis", "mucosa", and the like shall also be used interchangeably unless specifically stated otherwise.

In one aspect of the present disclosure, there are provided various mucosal delivery-enhancing agents to increase the palatability or solubility of the protein supplement, e.g., if the supplement is a tablet. The term, "mucosal delivery-enhancing agent" includes agents which enhance the release or solubility (e.g., from a formulation delivery vehicle), diffusion rate, penetration capacity and timing, uptake, residence time, stability, effective half-life, peak or sustained concentration levels, clearance and other desired mucosal delivery characteristics (e.g., as measured at the site of delivery, or at a selected target site of activity such as the bloodstream or central nervous system) of a compound(s) (e.g., biologically active compound). Enhancement of mucosal delivery can occur by any of a variety of mechanisms, including, for example, by increasing the diffusion, transport, persistence or stability of the compound, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junction physiology, reducing the viscosity of mucus overlying the mucosal epithelium, reducing mucociliary clearance rates, and other mechanisms.

Still, another aspect of the present disclosure, is a method and apparatus for vending high protein supplement products and the like, for example, the high protein supplement described herein can be in the form of beverage containers, or powder packets, both of varied sizes, shapes and configurations. The products to be vended are aligned in selectable ordered queues within a vending machine that can include a transparent front panel. A container release assembly is positioned at the end of the vend queue to vend a product (e.g., a beverage or a packet) upon activation. The vending machine apparatus is also suitable for vending items such as candy bars, chips, gum, and other "snacks" with or without the high protein supplement contained therein. For example, the vending machine apparatus can vend a first high protein supplement product (e.g., a beverage) having a first dimension and a second product (e.g., high protein packet) having a second dimension, the first dimension and the second dimension being different, from the same vend queue.

Protein, peptides and/or amino acids (PPAA) can also include medically or diagnostically useful PPAAs, of small to medium size to large size, e.g., up to 5 kDa, up to about 15 kDa, up to about 50 kDa, up to about 150 kDa, up to about 250 kDa and the like, or a protein having between about 1-100, about 1-300, about 1-1000, about 1-2500 amino acids or more. The compositions and methods described herein also anticipate the use of small molecules, for example, an organic compound that has a molecular weight of less than 3 kDa, or less than 1.5 kDa. The mechanisms of improved polypeptide absorption are described in U.S. Pat. No. 5,661,130, which is hereby incorporated by reference in its entirety.

The compositions described herein can be mixed with all such peptides, although the degree to which the peptide benefits are improved may vary according to the molecular weight and the physical and chemical properties of the peptide, and the particular surfactant used. Examples of polypeptides include biologically active peptides important in nutritional regulation.

Still in another embodiment, proteins described herein include modified proteins, such as truncated or elongated forms, and functional fragments thereof, with additional amino acid substitutions, including those substitutions which enable the site-specific coupling of at least one non-protein polymer, such as polypropylene glycol, polyoxyalkylene, or polyethylene glycol (PEG) molecule to the polypeptide. Site-specific coupling of PEG, for example, allows the generation of a modified polypeptide which possesses the benefits of a polyethylene-glycosylated (PEGylated) molecule, namely increased plasma half life. Non-specific PEGylation strategies are also encompassed in the present disclosure described herein, for example, N-terminal and lysine side-chain PEGylation. The methods described herein and other methods providing for PEGylation are well known and available in the art.

In one aspect, compositions herein can also include various "enhancement" factors and or agents. As used herein, the terms "enhancement", "penetration enhancement", or "permeation enhancement" refer to an increase in the permeability of the cellular barriers found in the mucosal membranes or the skin, to a delivery substance or agent, for example, a protein or peptide, so as to increase the rate at which the delivery substance permeates through the mucosal membranes or the skin. "Permeation enhancer", "enhancer", "penetration enhancer", or similar terms refer to a material, or materials that achieve or facilitate such permeation enhancement, and an "effective amount" of an enhancer means an amount effective to enhance penetration through the skin, of a protein, peptide and/or amino acid mix, to a selected degree. An index of permeation enhancers is disclosed by Osborne and Henke (1997), which is incorporated by reference herein. Osborne D. W. and Henke, J. J., "Skin penetration enhancers cited in the technical literature," Pharm Tech. 1997;21(11): 58-66. Enhanced permeation as affected through the use of such enhancers can be observed, for example, by measuring the rate of diffusion of the delivery substance through animal or human skin or cell-cultured mammalian cell layers simulating cell barriers found in mucosal membranes such as Caco-2 cells (see Lindgren et al., (2004) Biochem J 377:69-76), regenerated epidermis, dermis or skin, using a diffusion cell apparatus, or a similar apparatus or device familiar to those skilled in the art.

The compositions described herein may also include an inert carrier. As used herein, "inert carrier" refers to a polymeric carrier, or other carrier vehicle into which the protein or peptide may be admixed in order to form a transdermal delivery formulation. Inert carriers must generally be pharmaceutically acceptable, in that they are suitable for administration to the skin without causing significant instances of adverse results. Further, inert carriers must not react with the active substance to substantially degrade it, or otherwise form impurities, which may be delivered to the skin.

Concentrations, amounts, solubilities, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

In another embodiment, there is provided methods and formulations or compositions of producing stable formulations of biologically active peptides, proteins and/or amino acids, which formulations are useful for oral (e.g., sublingual) and intravenous delivery and other transmucosal or transdermal delivery modes of biologically active peptide or protein drugs.

Furthermore, the compositions described herein can be administered in a format selected from the group consisting of a drop, a spray, an aerosol and a sustained release format. The spray and the aerosol can be achieved through use of the appropriate dispenser. The sustained release format can be an ocular insert, erodible microparticulates, swelling mucoadhesive particulates, pH sensitive microparticulates, nanoparticles/latex systems, ion-exchange resins and other polymeric gels and implants (Ocusert, Alza Corp., Calif.; Joshi, A., S. Ping and K. J. Himmelstein, Patent Application WO 91/19481). These systems maintain prolonged drug contact with the absorptive surface preventing washout and nonproductive drug loss.

In some embodiments, there is provided a PPAA composition that is administered orally. The oral formulation or tablet can further include a pharmaceutically acceptable carrier. A "pharmaceutically acceptable carrier" is an aqueous or non aqueous agent, for example alcoholic or oleaginous, or a mixture thereof, and can contain a surfactant, emollient, lubricant, stabilizer, dye, perfume, preservative, acid or base for adjustment of pH, a solvent, emulsifier, gelling agent, moisturizer, stabilizer, wetting agent, time release agent, humectant, or other component commonly included in a particular form of pharmaceutical composition. Pharmaceutically acceptable carriers are well known in the art and include, for example, aqueous solutions such as water or physiologically buffered saline or other solvents or vehicles such as glycols, glycerol, and oils such as olive oil or injectable organic esters. A pharmaceutically acceptable carrier can contain physiologically acceptable compounds that act, for example, to stabilize or to increase the absorption of the specific inhibitor, for example, carbohydrates, such as glucose, sucrose or dextrans, antioxidants, such as ascorbic acid or glutathione, chelating agents, low molecular weight proteins or other stabilizers or excipients. A pharmaceutically acceptable carrier can also be selected from substances such as distilled water, benzyl alcohol, lactose, starches, talc, magnesium stearate, polyvinylpyrrolidone, alginic acid, colloidal silica, titanium dioxide, and flavoring agents.

The present disclosure encompasses an oral formulation wherein the formulation along with a pharmaceutically acceptable carrier includes at least one membrane coating surrounding the core, wherein the coating is an impermeable, permeable, semi-permeable or porous coating and becomes more permeable or porous upon contacting an aqueous environment of a defined pH. The term "membrane" is synonymous with "coating," or equivalents thereof. The terms are used to identify a region of a medicament, for example, a tablet, that is impermeable, permeable, semi-permeable or porous to an aqueous solution(s) or bodily fluid(s), and/or to the therapeutic agent(s) or drug(s) encapsulated therein. If the membrane is permeable, semi-permeable or porous to the amino acid, the amino acid can be released through the openings or pores of the membrane in solution or in vivo. The porous membrane can be manufactured mechanically (e.g., drilling microscopic holes or pores in the membrane layer using a laser), or it can be imparted due to the physiochemical properties of the coating polymer(s). Membrane or coating polymers of the disclosure are well known in the art, and include cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate, and cellulose acetate butyrate. Other suitable polymers are described in U.S. Pat. Nos. 3,845,770, 3,916,899, 4,008,719, and 4,036,228, which are incorporated herein by reference. This technology can be employed to prepare extended release or time-release formulations (e.g., microspheres, flakes, or granules) comprising monopeptidic Lysine, Arginine, and/or Histidine.

Accordingly, in some embodiments, an enteric coating can be designed to release a certain percentage of a drug or drugs (e.g., Lysine, Arginine, and/or Histidine) in certain mediums with a certain pH or pH range. For example, a composition, as described herein, may include at least one enteric coating encasing or protecting a formulation of Lysine, Arginine, and/or Histidine, which is chemically unstable in an acidic environment (e.g., the stomach). The enteric coating protects the Lysine, Arginine, and/or Histidine from the acidic environment (e.g., pH<3), while releasing the amino acids in locations which are less acidic, for example, regions of the small and large intestine where the pH is 3, or 4, or 5, or greater and/or releasing the Lysine, Arginine, and/or Histidine over an extended period of time (e.g., extended release, time-release or sustained release formulations of Lysine, Arginine, and/or Histidine). A dietary supplement of this nature may travel from one region of the gastrointestinal tract to the other, for example, it takes about 2 to about 4 hours for a compound to move from the stomach to the small intestine (duodenum, jejunum and ileum). During this passage or transit, the pH changes from about 3 (e.g., stomach) to 4, or 5, or to about a pH of 6 or 7 or greater. Thus, the enteric coating allows the core containing the Lysine, Arginine, and/or Histidine to remain substantially intact, and prevents premature release or the acid from penetrating and de-stabilizing the amino acid and/or allows for sustained release, time-release, or extended release.

Examples of suitable enteric polymers, which can be used to formulate sustained release, time-release, or extended release Lysine, Arginine, and/or Histidine include but are not limited to cellulose acetate phthalate, hydroxypropylmethylcellulose phthalate, polyvinylacetate phthalate, methacrylic acid copolymer, shellac, cellulose acetate trimellitate, hydroxypropylmethylcellulose acetate succinate, hydroxypropylmethylcellulose phthalate, cellulose acetate phthalate, cellulose acetate succinate, cellulose acetate malate, cellulose benzoate phthalate, cellulose propionate phthalate, methylcellulose phthalate, carboxymethylethylcellulose, ethylhydroxyethylcellulose phthalate, shellac, styrene-acrylic acid copolymer, methyl acrylate-acrylic acid copolymer, methyl acrylate-methacrylic acid copolymer, butyl acrylate-styrene-acrylic acid copolymer, methacrylic acid-methyl methacrylate copolymer, methacrylic acid-ethyl acrylate copolymer, methyl acrylate-methacrylic acid-octyl acrylate copolymer, vinyl acetate-maleic acid anhydride copolymer, styrene-maleic acid anhydride copolymer, styrene-maleic acid monoester copolymer, vinyl methyl ether-maleic acid anhydride copolymer, ethylene-maleic acid anhydride copolymer, vinyl butyl ether-maleic acid anhydride copolymer, acrylonitrile-methyl acrylate-maleic acid anhydride copolymer, butyl acrylate-styrene-maleic acid anhydride copolymer, polyvinyl alcohol phthalate, polyvinyl acetal phthalate, polyvinyl butylate phthalate and polyvinyl acetoacetyl phthalate, or combinations thereof. One skilled in the art will appreciate that other hydrophilic, hydrophobic and enteric coating polymers may be readily employed, singly or in any combination, as all or part of a coating according to the present disclosure.

The therapeutic or dietary compositions that include monopeptidic Lysine, Arginine, and/or Histidine may have the amino acid in the form of a tablet, microsphere, pellet, flake, or granule, which can have a plurality of coatings, for example, a hydrophilic coating (e.g., hydroxypropylmethylcellulose), and/or a hydrophobic coating (e.g., alkylcelluloses), and/or an enteric coating or other coating, as described above. For example, the core can be encased by a plurality of the same type of coating, or a plurality of different types of coating selected from a hydrophilic, hydrophobic or enteric coating. Hence, it is anticipated that a composition can be designed having at least one, but can have more than one layer consisting of the same or different coatings dependent on the type of sustained or extended release of or time of desired release of the Lysine, Arginine, and/or Histidine. For example the layer may have a first composition enclosed by a first coating layer (e.g. hydrophilic, hydrophobic, or enteri-coating), and a second same or different composition having the same or different dosage can be enclosed in second coating layer, etc. This layering of various coatings provides for a first, second, third, or more gradual or dose dependent release of the same or different Lysine, Arginine, and/or Histidine containing composition.

More embodiments concern providing a pharmaceutical or dietary supplement composition for slow release of active ingredient in the gastrointestinal tract, which substantially avoids the disadvantages mentioned and which can be produced at reasonable cost and with high reproducibility. More embodiments concern providing a pharmaceutical or dietary supplement composition, which permits slow release of active ingredient in the intestinal tract even when the active ingredient content is high and the excipient content is only low.

In more embodiments, the oral formulation or composition is used to create a slow release of active the ingredients, e.g., PPAAs, in the gastrointestinal tract, comprising a plurality of coated active ingredient-containing particles which have an active ingredient-containing core and a coating comprising a polymer insoluble in gastric and intestinal juices, where the active ingredient-containing core of the coated particles is a homogeneous mixture comprising an active pharmaceutical ingredient and a polymer insoluble in gastric and intestinal juices, as discussed above.

It should be noted that certain embodiments contemplate dietary supplements (e.g., powders for shakes) that comprise slow release formulations of an amount of isolated, purified, or synthetic monopeptidic lysine (e.g., equal to, greater than, at least, or any number in between 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg per serving) and/or isolated, purified, or synthetic monopeptidic arginine (e.g., equal to, greater than, at least, or any number in between 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg per serving) and/or isolated, purified, or synthetic monopeptidic histidine (e.g., equal to, greater than, at least, or any number in between 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg per serving) so that an effective amount of Lysine, Arginine, and/or Histidine is delivered to the consumer over an extended period.

The treatment involves selecting individuals with a form of wasting disease (e.g. Chronic Fatigue Syndrome, Fibromyalgia or Anorexia Nervosa) and/or a disease as result of excess caloric intake (e.g., overweight conditions, obesity, morbid obesity, Type II Diabetes Mellitus, Syndrome X (Metabolic Syndrome, Insulin resistance, and other related disorders). Once the disease and/or symptoms characteristic of the disease are diagnosed, the defined therapeutic supplements based on the compositions described herein, which have not been used previously for the treatment of these disorders, may be prescribed. The supplement should be ingested, for example, at times during the day when there is low food intake e.g., at night-time, during normal sleeping hours or prolonged sleeping periods associated with Chronic Fatigue Syndrome and Fibromyalgia. Moreover, purposefully waking the subject up from a sleep for administration of the therapeutic supplement is also encompassed by the treatment described herein.

Various dosages are described herein, however, it will be understood that the specific dose level and frequency of dosage for any particular subject in need of treatment may be varied and will depend upon a variety of factors including the activity of the specific compound employed, the metabolic stability and length of action of that compound, the age, body weight, general health, allergies, symptoms, sex, diet, mode and time of administration, rate of excretion, drug combination, the severity of the particular condition, and the host undergoing therapy. Generally, however, dosage will approximate that which is typical for known methods of administration of the specific high protein, peptide and/or amino acid composition formulations. Additionally, an appropriate amount may be determined by one of ordinary skill in the art using only routine testing given the teachings described herein (e.g. analysis of amino acid levels in the blood circulation or urine).

The following examples are intended to illustrate but not limit the invention.

EXAMPLE 1

High Protein Therapeutic Supplements

The following describes various embodiments, including different high protein therapeutic supplement compositions. One skilled in the art will understand that the compositions are not limited to the listed ingredients, but can include other ingredients and elements not specifically listed, and still be within the scope of the present invention.

The supplement has been provided to a small group of patients with beneficial results in all cases and symptomatically complete cures in several cases. Beneficial effects were observed in about 24-72 hours. Typically, partial or complete cures were found in about 3-6 months following daily oral treatment. The exact regimen prescribed will vary depending on the severity of the disorder.

In one embodiment, the high protein therapeutic supplement contains, for example, 2 tablespoon dry mix, which comprises:

| Calories = about 105 | |
|---|---|
| | Approximate % Daily Value |
| Total fat 1.5 g | 2% |
| Saturated fat 0.5 g | 3% |
| Cholesterol 30 mg | 10% |
| Sodium 80 mg | 3% |
| Potassium 100 mg | 3% |
| Total carbohydrate 2 g | 1% |
| Sugars 2 g | |
| Protein 21 g | 42% |
| Vitamin A | 45% |
| Vitamin C | 45% |
| Calcium | 15% |
| Iron | 45% |
| Vitamin E | 45% |
| Thiamine | 45% |
| Riboflavin | 45% |
| Niacin | 45% |
| Vitamin B6 | 45% |
| Folate | 45% |
| Vitamin B12 | 45% |
| Biotin | 45% |
| Pantothenic acid | 45% |
| Phosphorus | 10% |
| Iodine | 45% |
| Magnesium | 60% |
| Zinc | 45% |
| Copper | 45% |

Each serving (2 tbsp=28 g) may contain the following, where "E" stands for essential amino acids:

L amino acids:

| | | |
|---|---|---|
| Isoleucine | 1240 mg | E (branched) |
| Leucine | 2160 | E |
| Lysine | 1680 | E |
| Methonine | 1140 | E |
| Phenylalanine | 1460 | E |
| Threonine | 1410 | E |
| Tryptophan | 320 | E |
| Valine | 1030 | E |
| Alanine | 1030 | |
| Arginine | 530 | E (essential in young/elderly-semi-essential) |
| Aspartic acid | 2500 | |
| Glutamic acid | 3500 | |
| Glycine | 400 | |
| Histidine | 380 | (essential in young/elderly-semi-essential) |
| Proline | 1220 | |
| Serine | 1030 | |
| Tyrosine | | |
| Cysteine | | |

The above supplement can also contain various amino acids, including, but not limited to, asparagines (A, Asn), glutamine (Q, Glu), and the like.

Still, the above supplement can also contain various ingredients, including, but not limited to, Magnesium oxide, Ascorbic acid, Ferrous fumarate, Vitamin E acetate, Niacinamide, Zinc oxide, Copper gluconate, Calcium pantothenate, Vitamin A palmitate, Pyridoxine hydrochloride, Riboflavin, Thiamine hydrochloride, Folic acid, Biotin, Potassium iodide, Cyanocobalamin, Lutein and the like.

In one therapeutic regimen, the subject can mix 1-4 tbsp powder or equivalent in an electric blender with 4-12 oz of fluid (water, juice, soy milk, milk and the like), then take the mixture orally about 1 to 3, about 1 to 4, about 1 to 5 times per day, depending on the severity of protein deficiency (e.g., 1 to 3 tbsp equals 10-30 grams of protein or 20% to 60% of daily value).

The supplement can be used for therapeutic and/or dietary supplementation. The supplement can also be taken during periods of low or inadequate protein intake, night and/or day (temporal protein deficiency) so long as the results are achieved and attained. For example, the treatment and/or supplementation may be provided at specific times during the diurnal period when temporary or temporal protein and amino acid deficiencies are present, such as during sleeping hours when protein intake is diminished or inadequate, and/or during waking hours when protein intake is insufficient leading to excessive catabolic activities.

In another aspect, the composition can be provided every four hours during periods of inadequate protein intake, e.g., during a regular 9-5 working day, in the middle of the night, or during times when food is scarce or a meal is skipped.

In nutritional excess diseases (overweight conditions, obesity and morbid obesity), the composition may be provided in response to food cravings or temporally famished states or in lieu of poor nutritional foods that lead to rapid fat gains. Improvements in nutritional status and increase in sense of well-being due to the nutritional product will also diminish stress reactions and promote increased physical activity, including exercise that may accelerate weight loss efforts.

In nutritional wasting diseases (Chronic Fatigue Syndrome, Fibromyalgia and Anorexia Nervosa) the composition may first be provided to improve nutritional status and further to block the effects of catabolism that leads to famished states and food craving behavior. Later, the administration of the compositions will allow substitution of healthy foods for unhealthy foods that lead to deleterious effects (hyperglycemia and hyperinsulinemia followed by hypoglycemia, leading to increased fatigue). Finally, administration of the compositions will allow the assimilation of healthy foods (protein, complex carbohydrates and essential fatty acids) that will rebuild the body to restore normal weight levels.

EXAMPLE 2

Administration of a High Protein Supplement Causes Weight Loss in Overweight or Obese Subjects Several overweight individuals were treated with the high protein supplement formulated substantially as described in Example 1. The subjects and the weight loss effects are as described herein.

Subject A is a 56 year old female who was 20 pounds overweight. The weight gain was attributed to age and postmenopausal state. She has been taking the high protein supplement in the form of a shake for about two months, two to three times per day. On average, she has lost about 8 pounds in 4 weeks.

Subject B is a 54 year old female who was 30 pounds overweight, with similar causes of weight gain as in subject A. She has been taking the high protein supplement in the form of juice blend for about a month, two to three times per day. On average, she has lost about 5 pounds in 4 weeks.

Subject C is a 46 year old female who is obese and about 270 pounds overweight. Her extreme weight gain is attributed to stress and poor nutrition. She has been taken the high protein supplement with grape juice for about a month, two to three times per day. On average, she has begun to show positive effects including increased energy (e.g., beginning to use treadmill), increased satiety, and improvements in sleep patterns. Subject C has lost about 8 pounds after three weeks.

Subject D is a 65 year old male who is about 20 pounds overweight, the majority of the weight due to an increase in visceral fat. He suffers from borderline normal to high blood pressure over the years (e.g., 140/94), interim insomnia, a recent 50% hearing loss in the left ear (e.g., decrease in hearing in left ear over past 5 years), and weakness in left leg with intermittent pain in left hip and knee joints, detected on walking, over past 10 years. He has been taking 1.5 tablespoons of the high protein supplement for about 5 months. Since being on the high protein supplement, he has shown an increase in peripheral vision within three days, moderate induction in sleep when the high protein supplement is taken during periods of insomnia, mild elevation in mood, and steady increases in hearing in left ear beginning at 3 weeks with total return of auditory function by about 8-10 weeks. H is hearing so improved that telephone could be transferred back to left ear. Since taking the high protein supplement, he has a significant increase in energy and muscular strength (e.g., moderate weight lifting routine facilitated allowing twice the number of repetitions with ease). The increased muscular strength has strengthened his left leg allowing him to walk without joint pain. He has also lost about 15 pounds within about four months, particularly observed in his face and extremities. Also, his visceral fat decreased by about 50% over about six months.

Thus, the high protein supplement of the present disclosure ameliorates symptoms associated with being over weight and obese (e.g., decrease in energy, increase in visceral fat, decrease in muscle tone, and the like). Also, the high protein supplement can be taken in many forms (e.g., shakes, juice blend, in water, or dry) and in various dosages and frequency. Although beneficial effects are shown for those subjects above taking the high protein supplement for about 1 to 6 months, the best results are expected from those subjects who are on the regimen for about four (4) months (e.g., subject D).

EXAMPLE 3

Administration of a High Protein Supplement Effects Weight Gain in Subjects with Catabolic Disease Compositions described herein are also useful for people that suffer from catabolic diseases. The high protein supplements used in these embodiments are substantially as that described in Example 1.

Subject E is a 55 year old female who is suffering from catabolic disease due to poor food intake. Her weight decreased to about 112 pounds in a few years ago due to anxiety, back pain, chest pain and gastric distress on ingesting food. She has had extreme difficulty in gaining weight and multiple medical workups and medications had no effect. She has been taking the high protein supplement for about three (3) months, with the dosage increasing from one teaspoon to two teaspoons twice daily at about 7 AM and at 6 PM. After being on the high protein supplement for about three months, she demonstrated sustained beneficial effects including: weight gain of about 11 pounds over a three month period to about 123 pounds; significant improvement in appetite; increased feelings of well-being enhanced; improved mood; and in her own words, she has returned to feeling like "herself".

EXAMPLE 4

Administration of a High Protein Supplement Ameliorates Symptoms Associated with Fibromyalgia and Chronic Fatigue Syndrome Compositions described herein are also useful for people that suffer from fibromyalgia and chronic fatigue syndrome and symptoms associated with the diseases. The high protein supplements are substantially as that described in Example 1.

Subject F is a 38 year old female, diagnosed with chronic fatigue syndrome with multiple epithelial lesions on tongue, scalp, skin, finger nails, poor menstruation, prolonged infections and sugar intolerance. Her symptoms have increased over the past 8 years and she has seen 29 doctors without benefit. She weighed 125 pounds. She was taking the protein supplement about three weeks and did not take it for about a month. Then she restarted taking the high protein supplement but with an increase dose to three tablespoons once she wakes up and every four hours thereafter. She received positive beneficial effects including: (i) cessation of famished states leading to binge eating resulting in hyperglycemia followed by hypoglycemia as defined by symptoms of blurred vision, extreme fatigue, spacey countenance and dizzy feelings; (ii) satiety with decreased sugar cravings and (iii) positive feelings with steadier mood. The high protein supplement taken when she wakes up in the morning, about 7:30 AM, made her hungry by about 9 AM. She has not eaten breakfast in years. Her weight has remained stable, meaning she has avoided increases in weight, according to design.

Subject G is a 46 year old female suffering from fibromyalgia. She has normal weight and non-specific symptoms including easy fatigability, poor sleep patterns and a "foggy" mind. Her body is excessively sensitive to pressure indicative that she suffers from various muscle pain and stiffness. She has been taking the high protein supplement for about 3 months and has received positive beneficial effects including boosts in energy. However, she continues to have very sensitive spots on body (e.g., when pressed in these places, she feels intense pain).

Subject H is a 52 year old female suffering from Chronic Fatigue Syndrome. Despite history as an active flight attendant, she has a ten year history of progressive chronic fatigue and malaise; and in the past 5 years she has remained in bed for about 15 hours a day. She has been taking the high protein supplement for about one month and has already received positive beneficial effects including: boosts in energy levels; small increase in well-being; sometimes she gets out of bed at noon and functioning well. Her weight is stable at about 128 pounds, avoiding a weight gain by design.

The high protein supplement of the present disclosure can be used in various modalities including, treatment for weight gain and/or obesity, as well as increasing weight gain and improving energy levels. One skilled in the art will understand that the dosages and frequency of the supplement will vary with the symptoms and disease being treated. The positive beneficial effects received will also vary depending on the complexity and numbers of symptoms and diseases being treated. As shown for subject D, taking the high protein supplement for a period of at least about four, five, six or more months is recommended, although beneficial results are observed in less time. Further, as described above, the high protein supplement need not be taken to treat symptoms or diseases related to weight, but can also be taken to treat complex diseases such as chronic fatigue syndrome

EXAMPLE 5

In one embodiment, a dietary supplement is composed of a powder, which comprises a power amino acid complex, a Factor-4 protein complex and other ingredients. The power amino acid complex comprises L-Lysine, L-Arginine, L-Isoleucine, L-Leucine, L-Threonine, L-Valine, dl-Phenylalanine (or L-Phenylalanine), L-Methionine, L-Histidine, 5-Hydroxy Tryptophan (or L-Hydroxy Tryptophan or L-Tryptophan). The Factor-4 protein complex comprises whey protein isolate, whey protein concentrate, and soy protein isolate. In some embodiments the Factor-4 protein complex comprises egg protein. The other ingredients can comprise guar gum, lecithin, natural and artificial flavors, natural and artificial colors, fructo-oligosaccharide, natural and artificial sweeteners. The above ingredients are mixed in specific ratios to yield the protein powder composition with the nutritional information listed in Table 2.

TABLE 2

| | |
|---|---|
| Calories | 71 |
| Calories from Fat | 15 |
| Total Fat** | 1.6 g |
| Cholesterol | 12 mg |
| Total Carbs | <1.2 g |
| Fiber | 1.5 g |
| Sugars | 0.3 g |
| Protein | 11.5 g |
| Vitamin A (Palmitate) | 3000 IU |
| Vitamin C (Ascorbitol Palmitate) | 30 mg |
| Vitamin E (dl-alpha tocopheryl acetate) | 10 IU |
| Vitamin B1 (Thiamine mononitrate) | 1 mg |
| Vitamin B2 (Riboflavin 5 phosphate) | 1.13 mg |
| Vitamin B6 (Pyridoxine HCl) | 1.3 mg |
| Niacin | 20 mg |
| Vitamin B12 (Cyanocobalamine) | 4 mcg |
| Lutein | 1 mg |
| Calcium (Dicalcium malate, protein) | 150 mg |
| Magnesium (Amino acid chelate) | 100 mg |
| Phosphorus | 63 mg |
| Zinc (Amino acid chelate) | 4 mg |
| Potassium | 65 mg |
| Sodium | 8.8 mg |
| Gamma-linolenic acid | 15 mg |
| Bromelain | 25 mg |
| Papain | 25 mg |
| Manganese (Chelate) | 1 mg |
| Selenium (Selenomethionine) | 35 mcg |
| Chromium (Chelate) | 60 mcg |
| Boron (Citrate) | 100 mcg |
| Molybdenum (Chelate) | 37.5 mcg |
| Iodine (Kelp) | 37.5 mcg |
| Biotin | 150 mcg |
| Folic Acid | 400 mcg |

In some embodiments a serving of the dietary supplement can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In an embodiment a 16.5 g serving of the Factor-4 protein powder composition contains the following amounts listed in Table 3.

TABLE 3

| | |
|---|---|
| L-Arginine HCl | 445 mg |
| L-Lysine HCl | 1105 mg |

TABLE 3-continued

| | |
|---|---|
| L-Isoleucine | 825 mg |
| dl-Phenylalanine (or L-Phenylalanine) | 280 mg |
| L-Methionine | 240 mg |
| L-Leucine | 1060 mg |
| L-Valine | 610 mg |
| L-Threonine | 710 mg |
| L-Histidine HCl | 180 mg |
| 5-Hydroxy Tryptophan (or L-Hydroxy Tryptophan or L-Tryptophan) | 160 mg |
| L-Alanine | 660 mg |
| L-Aspartic Acid | 1103 mg |
| L-Glutamic Acid | 1775 mg |
| L-Cystine | 205 mg |
| L-Glycine | 180 mg |
| L-Serine | 450 mg |
| L-Proline | 620 mg |
| L-Tyrosine | 270 mg |
| Taurine | 200 mg |

EXAMPLE 6

A study was performed to monitor body fat, lean body (muscle) mass and total body weight during a three month period. Subjects were provided with the dietary supplement described in Example 5 and provided with both recommendations on good eating habits and encouragement to increase exercise routine. The study was an open label study with no placebo group.

Adult men and women were recruited as motivated volunteers through a newspaper advertising program. Women who are or may be pregnant were excluded. Subjects were accepted if they are overweight, obese or morbidly obese (more than 100 pounds overweight). A measure of body mass index (BMI) was used during the study to determine if a subject was overweight, obese or morbidly obese. The equation used to calculate body mass index is body weight in kilograms divided by height in meters squared. This equation works for most people but is not a good indicator of obesity for weight lifters. Generally, a BMI of less than 25 is in the normal range, whereas a BMI between 25 and 29.9 indicates the subject is overweight. A BMI of 30 or higher indicates the subject is obese. Lower rates of weight loss correlated with BMI readings which were in the normal range. Overweight individuals were accepted if they fell outside the normal weight range for their age and gender.

The subjects chosen for the study then participated in the following:

First, subjects were asked to fill out a questionnaire used for inclusion/exclusion purposes and to sign a consent form to participate as a research subject in an evaluation of weight loss, weight management and changes in body fat utilizing dietary supplements. The consent form included questions related to symptoms and side-effects, risks and benefits, follow up, confidentiality of records and compensation.

Second, subjects were invited to an orientation meeting where the purpose of the study and the design of the study are discussed. Subjects were advised on good eating habits by the personal trainer and according to weight loss tips sent to each subject by e-mail. Subjects were also encouraged by the personal trainer to increase his or her exercise routine.

Third, subjects were provided with a mixture including the dietary supplement described in Example 5 dissolved in 8 oz of water. The mixture was provided to the subjects three times a day (1) upon arising and before breakfast; (2) at mid-day as a snack or as a lunch beverage; and (3) in the evening before dinner, during dinner or after dinner (according to the preference of the individual subjects).

Fourth, each subject kept a daily nutrition journal in which he or she recorded all meals and snacks (including any ingestion of the mixture described above), and any dietary indiscretions.

Weekly, each subject visited the personal trainer to measure body weight with a gravimetric scale. Measurements were also taken with a Sony near infra-red laser to measure fat content in 12 body locations. Infra-red measurements were accurate to +/−1%. Utilizing the body weight and ratios of fat to lean body mass, the following measurements are calculated: (1) body fat in pounds and as a percentage of body weight; (2) lean body weight in pounds and as a percentage of body weight; (3) BMI; and (4) total body water in liters and as a percentage of body weight.

Twenty five subjects completed the three month weight loss study. Twenty four subjects lost a cumulative total of 286 pounds with an average weight loss of 12 lbs per subject. Of the twenty four subjects who lost weight, the weight loss varied between 3 and 27 pounds. All subjects decreased their BMI.

FIG. 1 illustrates a graph of the weekly weigh-in measurements for a group of subjects whose initial body weight was between 100 and 200 lbs. The trend lines for each of subject nos. 102, 108, 111, 112, 113, 123 and 125 are illustrated. The graph illustrates several of the subjects with relatively consistent weight loss trends over approximately 20 weeks.

Figure 2:
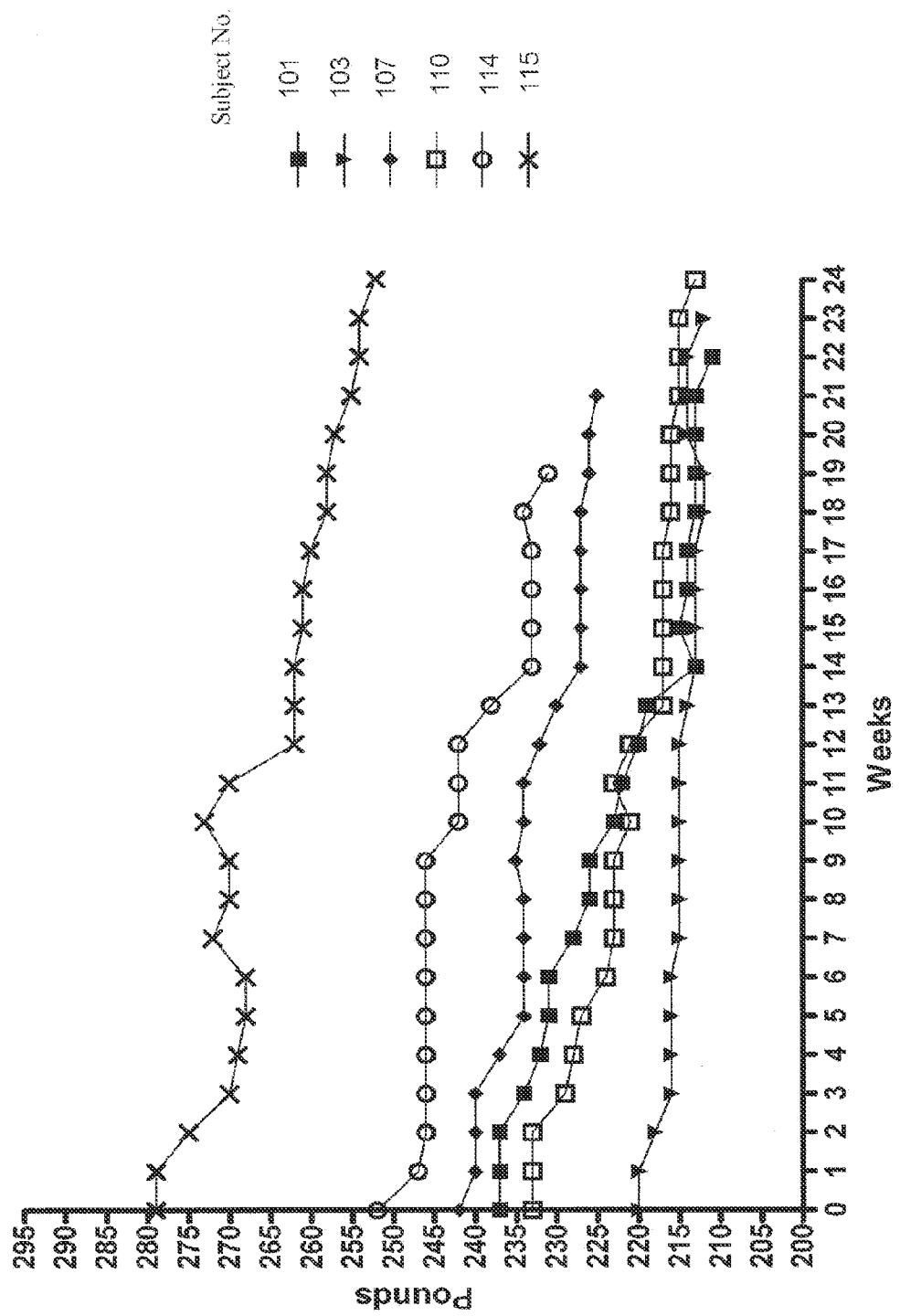
FIG. 2 is a graph of subjects of a weight loss study whose initial weight was between 200 and 300 lbs.

FIG. 2 illustrates a graph of the weekly weigh-in measurements for a group of subjects whose initial body weight was between 200 and 300 lbs. The trend lines for each for subject nos. 101, 103, 107, 110, 114 and 115 are illustrated. The graph illustrates several of the subjects with relatively consistent weight loss trends over approximately 22 weeks.

Individual subject histories are included below.

Subject 101: Weight Loss, 26 Pounds

Subject 101 is a 63 year old male, 5' 10" tall. He entered the study on May 15, 2006, completed the three month study and extended through 22 weeks. He weighed into the study at 237 pounds with a BMI of 33.9 (obese) and a waist size of 48 inches. At three months he had lost 17 pounds of total weight and 4.6 pounds of fat, decreasing his percent body fat from 31.4% to 29%. His waist size decreased by 4.5 inches. At the end of 22 weeks, he had lost 26 pounds of total weight, including 8.3 pounds of fat, further decreased his percent body fat to 28.5% and further decreased his waist size by 5.5 inches. His BMI decreased to 30.2. Losing more than 20 pounds of weight, subject achieved large-scale weight loss with sustained weight control.

Subject 102: Weight Loss, 16 Pounds

Subject 102 is a 61 year old female, 5' 6" in height. She entered the study on May 15, 2006, completed the three month study and extended through 22 weeks. Subject weighed into the study at 178 pounds with a BMI of 28.6 (overweight) and a waist size of 43 inches. At three months she had lost 9 pounds of total weight and 4.6 pounds of fat, marginally decreased her percent body fat and shed 4.5 inches from her waist. At the end of 22 weeks, she had lost 16 pounds of total weight, 6.3 pounds of fat, decreased her percent body fat by 0.8% and shed 6 inches from her waist. Subject decreased her BMI to 26.0. Losing 16 pounds of weight, subject achieved moderate weight loss with sustained weight control.

Subject 103: Weight Loss, 8 Pounds

Subject 103 is a 69 year old male, 6 feet in height. He entered the study on May 15, 2006, completed the three month study and extended through 23 weeks. Subject weighed into the study at 220 pounds with a BMI of 29.8 (obese) and a waist size of 44 inches. At three months he had lost 5 pounds of total weight and 2.2 pounds of fat, decreased his percent body fat by 0.4% and shed 3 inches from his waist. At the end of 22 weeks, he had lost 8 pounds of total weight, 4 pounds of fat, decreased his percent body fat by 0.8% and continued to show 3 inches lost from his waist. Subject decreased his BMI to 28.7. Losing 8 pounds of weight, subject achieved modest weight loss with sustained weight control.

Subject 104: Weight Loss, 10 Pounds

Subject 104 is a 60 year old female, 5' 8" in height. She entered the study on May 15, 2006, and completed the three month study. Subject weighed into the study at 222 pounds with a BMI of 33.7 (obese) and a waist size of 39 inches. At three months she had lost 10 pounds of total weight and 8.1 pounds of fat, decreased her percent body fat by 2.1% and showed little or no reduction in her waist size. Losing 10 pounds of weight, subject achieved moderate weight loss with sustained weight control.

Subject 105: Weight Loss, 7 Pounds

Subject 105 is a 59 year old male, 6' 1" in height. He entered the study on May 15, 2006 and completed the three month study. Subject weighed into the study at 242 pounds with a BMI of 32.1 (obese) and a waist size of 45 inches. At three months he had lost 7 pounds of total weight and 5.5 pounds of fat, decreased his percent body fat by 1.4% and shed 1 inch from his waist. Subject decreased his BMI to 29.8. Losing 7 pounds of weight, subject achieved modest weight loss with sustained weight control.

Subject 106: Weight Loss, 7 Pounds

Subject 106 is a 65 year old female, 5' in height. She entered the study on May 15, 2006 and completed the three month study. Subject weighed into the study at 153 pounds with a BMI of 30 (obesity) and a waist size of 34 inches. At three months she had lost 7 pounds of total weight and 3.3 pounds of fat, decreased her percent body fat by 0.4% and showed little or no reduction in her waist size. Losing 7 pounds of weight, subject achieved modest weight loss with sustained weight control.

Subject 107: Weight Loss, 17 Pounds

Subject 107 is a 57 year old male, 6' 1" in height. He entered the study on May 15, 2006, completed the three month study and extended to 21 weeks. Subject weighed into the study at 242 pounds with a BMI of 32.1 (obese) and a waist size of 48 inches. At three months he had lost 10 pounds of total weight and 5.7 pounds of fat, decreased his percent body fat by 1% and shed 4 inches from his waist. At the end of 21 weeks, he had lost 17 pounds of total weight, 9 pounds of fat, decreased his percent body fat by 1.4% and shed 6 inches from his waist. Losing 17 pounds of weight, subject achieved moderate weight loss with sustained weight control.

Subject 108: Weight Loss, 11 Pounds

Subject 108 is a 52 year old female, 5' 5" in height. She entered the study on May 15, 2006, completed the three month study and extended the study to 18 weeks. Subject weighed into the study at 193 pounds with a BMI of 32.2 (obese) and a waist size of 37 inches. At three months she had lost 11 pounds of total weight and 6.4 pounds of fat and shed 1 inch from her waist. At the end of 18 weeks, she had lost 11 pounds of total weight, 7.5 pounds of fat and shed 1 inch from her waist. Subject decreased her BMI to 30.3. Losing 11 pounds of weight, subject achieved moderate weight loss with sustained weight control.

Subject 109: Weight Loss, 8 Pounds

Subject 109 is a 60 year old male, 5' 9" in height. He entered the study on May 15, 2006 and completed the three month study. Subject weighed into the study at 233 pounds with a BMI of 34.5 (obese) and a waist size of 47 inches. At three months he had lost 8 pounds of total weight and 9.4 pounds of fat, decreased his percent body fat by 3.1% and shed 1 inch from his waist. Losing 8 pounds of weight, subject achieved modest weight loss with sustained weight control.

Subject 110: Weight Loss, 20 Pounds

Subject 110 is a 38 year old female, 5' 7" in height. She entered the study on May 15, 2006, completed the three month study and extended the study to 24 weeks. Subject weighed into the study at 233 pounds with a BMI of 36.6 (obese) and a waist size of 43 inches. At three months she had lost 12 pounds of total weight and 9.9 pounds of fat, decreased her percent body fat by 2.6% and shed 0 inches from her waist. At the end of 24 weeks, she had lost 20 pounds of total weight, 13.9 pounds of fat, decreased her percent body fat by 2.5% and showed 1.25 inches decrease in waist size. Subject decreased her BMI to 33.40. Losing 20 pounds of weight, subject achieved large-scale weight loss with sustained weight control.

Subject 111: Weight Loss, 3 Pounds (Lost 8.4 Pounds of Fat)

Subject 111 is a 46 year old female, 5' 3" in height. She entered the study on May 15, 2006, completed the three month study and extended the study to 17 weeks. Subject weighed into the study at 135 pounds with a BMI of 23.9 (normal) and a waist size of 31 inches. At three months she had gained 1 pound of total weight and had lost 4.4 pounds of fat, decreased her percent body fat by 2.9% and shed 1 inch from her waist. At the end of 17 weeks, she had lost 3 pounds of total weight, 8.4 pounds of fat, decreased her percent body fat by 5.5% and lost 1" in waist size. Subject decreased her BMI to 23.4. Losing 3 pounds of total weight and 8.4 pounds of fat weight, subject achieved modest to moderate weight loss with sustained weight control.

Subject 112: Weight Loss, 14 Pounds

Subject 112 is a 63 year old female, 5' 3" in height. She entered the study on May 15, 2006, completed the three month study and extended the study to 20 weeks. Subject weighed into the study at 170 pounds with a BMI of 30.1 (obese) and a waist size of 37 inches. At three months she had lost 10 pounds of total weight and had lost 5.7 pounds of fat, decreased her percent body fat by 1.4% and shed 1 inch from her waist. At the end of 20 weeks, she had lost 14 pounds of total weight, 4.2 pounds of fat, showed no decrease in percent body fat and lost 1" in waist size. Subject decreased her BMI to 28.2. Losing 14 pounds of total weight, subject achieved moderate weight loss with sustained weight control.

Subject 113: Weight Loss 23 Pounds

Subject 113 is a 56 year old female, 5' 2" in height. She entered the study on May 15, 2006, completed the three month study and extended the study to 23 weeks. Subject weighed into the study at 162 pounds with a BMI of 29.8 (obese) and a waist size of 34 inches. At three months she had lost 13 pounds of total weight including 5.7 pounds of fat, decreased her percent body fat by 0.8% and shed 3.5 inches from her waist. At the end of 23 weeks, she had lost 23 pounds of total weight, 12.1 pounds of fat, 2.9% in percent body fat and lost 6 inches in waist size. Subject decreased her BMI to 25.6. Losing 23 pounds of total weight, subject achieved large-scale weight loss with sustained weight control.

Subject 114: Weight Loss, 21 Pounds

Subject 114 is a 63 year old male, 5' 10" in height. He entered the study on May 15, 2006, completed the three month study and extended to 19 weeks. Subject weighed into the study at 252 pounds with a BMI of 36.1 (obese) and a waist size of 47 inches. At three months he had lost 10 pounds of total weight including 4.1 pounds of fat, decreased his percent body fat by 0.4% and shed 0 inches from his waist. At the end of 19 weeks, he had lost 21 pounds of total weight, 14.5 pounds of fat, decreased his percent body fat by 3.4% and shed 5 inches from his waist. Subject decreased his BMI to 33.1. Losing 21 pounds of weight, subject achieved large-scale weight loss with sustained weight control.

Subject 115: Weight Loss, 27 Pounds

Subject 115 is a 40 year old female, 5' 8" in height. She entered the study on May 15, 2006, completed the three month study and extended the study to 24 weeks. Subject weighed into the study at 279 pounds with a BMI of 41.4 (obese) and a waist size of 44 inches. At three months she had lost 11 pounds of total weight including 4 pounds of fat, increased her percent body fat by 0.4% and shed no inches from her waist. At the end of 24 weeks, she had lost 21 pounds of total weight, 17.2 pounds of fat, 3% in percent body fat and 2 inches in waist size. Subject decreased her BMI to 38.2. Losing 27 pounds of total weight, subject achieved large-scale weight loss with sustained weight control.

Subject 116: Weight Gain, 3 Pounds

Subject 116 is a 42 year old male, 6' 2" in height. He entered the study on May 15, 2006 and completed the three month study. Subject weighed into the study at 220 pounds with a BMI of 28.2 (overweight) and a waist size of 42 inches. At three months he had gained 3 pounds of total weight including 2.4 pounds of fat, increased his percent body fat by 0.8% and shed 0 inches from his waist. Gaining 3 pounds of weight, subject failed to lose weight and failed to achieve sustained weight control.

Subject 117: Weight Loss 9 Pounds

Subject 117 is a 39 year old female, 5' 6" in height. She entered the study on May 15, 2006 and completed the three month study. Subject weighed into the study at 176 pounds with a BMI of 28.3 (overweight) and a waist size of 39 inches. At three months she had lost 9 pounds of total weight, lost 3.3 pounds of fat, decreased percent body fat by 0.1% and shed no inches from her waist. Losing 9 pounds of total weight, subject achieved modest weight loss with sustained weight control.

Subject 118: Weight Loss, 3 Pounds

Subject 118 is a 40 year old female, 5' 6" in height. She entered the study on May 15, 2006, completed the three month study. Subject weighed into the study at 231 pounds with a BMI of 37.2 (obese) and a waist size of 40 inches. At three months she had lost 3 pounds of total weight, lost 5.3 pounds of fat, decreased percent body fat by 1.8% and shed no inches from her waist. Losing 3 pounds of total weight and 5.3 pounds of fat, subject achieved modest weight loss with sustained weight control.

Subject 119: Weight Loss, 7 Pounds

Subject 119 is a 41 year old male, 5' 9" in height. He entered the study on May 15, 2006 and completed the three month study. Subject weighed into the study at 234 pounds with a BMI of 34.7 (obese) and a waist size of 43 inches. At three months he had lost 7 pounds of total weight, lost 7 pounds of fat, decreased his percent body fat by 2% and shed 0 inches from his waist. Losing 7 pounds of weight, subject achieved modest weight loss with sustained weight control.

Subject 120: Weight Loss, 8 Pounds

Subject 120 is a 60 year old female, 5' 4" in height. She entered the study on May 15, 2006, completed the three month study. Subject weighed into the study at 230 pounds with a BMI of 39.3 (obese) and a waist size of 50 inches. At three months she had lost 8 pounds of total weight, lost 8.8 pounds of fat, decreased percent body fat by 2.5% and shed 2 inches from her waist. Losing 8 pounds of total weight and 8.8 pounds of fat, subject achieved modest to moderate weight loss with sustained weight control.

Subject 121: Weight Loss, 5 Pounds

Subject 121 is a 53 year old male, 5' 7" in height. He entered the study on May 15, 2006 and completed the three month study. Subject weighed into the study at 204 pounds with a BMI of 32 (obese) and a waist size of 40 inches. At three months he had lost 5 pounds of total weight, lost 5.5 pounds of fat, decreased his percent body fat by 2% and shed 1 inch from his waist. Losing 5 pounds of weight and 5.5 pounds of fat, subject achieved modest weight loss with sustained weight control.

Subject 122: Weight loss, 7 pounds

Subject 122 is a 57 year old female, 5' in height. She entered the study on May 15, 2006 and completed the three month study. Subject weighed into the study at 183 pounds with a BMI of 36 (obese) and a waist size of 43 inches. At three months she had lost 7 pounds of total weight, lost 4.2 pounds of fat, decreased percent body fat by 0.8% and shed 0 inches from her waist. Losing 7 pounds of total weight and 4.2 pounds of fat, subject achieved modest weight loss with sustained weight control.

Subject 123: Weight Loss, 8 Pounds

Subject 123 is a 43 year old female, 5' in height. She entered the study on May 15, 2006 and completed the three month and extended to 19 weeks. Subject weighed into the study at 146 pounds with a BMI of 28.7 (overweight) and a waist size of 35 inches. At three months she had lost 6 pounds of total weight, lost 2.2 pounds of fat, decreased percent body fat by 0.1% and shed 0 inches from her waist. At the end of 19 weeks, she lost 8 pounds of total weight, 3.7 pounds of fat, 0.6% in percent body fat and lost 0 inches in waist size. Subject decreased her BMI to 26.9. Losing 8 pounds of total weight and 3.7 pounds of fat, subject achieved modest weight loss with sustained weight control.

Subject 124: Weight Loss, 7 Pounds

Subject 124 is a 33 year old female, 5' 7" in height. She entered the study on May 15, 2006 and completed the three month study. Subject weighed into the study at 216 pounds with a BMI of 33.9 (obese) and a waist size of 40 inches. At three months she had lost 7 pounds of total weight, lost 1.8 pounds of fat, showed no decrease in percent body fat and shed 2 inches from her waist. Losing 7 pounds of total weight and 1.8 pounds of fat, subject achieved modest weight loss with sustained weight control.

Subject 125: Weight Loss, 14 Pounds

Subject 125 is a 65 year old female, 5' 4" in height. She entered the study on May 15, 2006, completed the three month study and extended to week 18. Subject weighed into the study at 193 pounds with a BMI of 33 (obese) and a waist size of 37 inches. At three months she had lost 10 pounds of total weight, lost 4.8 pounds of fat, decreased her percent body fat by 0.7% and shed 0 inches from her waist. At the end of 18 weeks, she had lost 14 pounds of total weight, 7 pounds of fat, 1.1% in percent body fat and lost 0 inches in waist size. Subject decreased her BMI to 30.6. Losing 14 pounds of weight and 7 pounds of fat, the subject achieved moderate weight loss with sustained weight control.

EXAMPLE 7

Improvement of Nutritional Imbalance

A subject can be identified as one having a nutritional imbalance by clinical or diagnostic techniques that are known in the art. In some embodiments, the existence of a nutritional imbalance in a subject is identified by employing a proteomic analysis of a sample obtained from said subject (e.g., cheek cells, cells of the oral cavity, hair, saliva, lacrimal secretion, blood, urine, digestive juice obtained from the stomach, fecal material, or spinal fluid). The proteomic analysis can include a separation of proteins obtained from said sample (e.g., Isoelectric Focusing and/or 2D gel electrophoresis (IEF followed by SDS-PAGE)) and characterization of the proteins and/or amino acids can be accomplished by conventional techniques (e.g., mass spectroscopy and/or immunolabeling). In some embodiments, an analysis and measurement of the amount and/or presence of one or more essential and semi-essential amino acids, in particular a positively charged amino acid (e.g., Lysine, Arginine, and/or Histidine), is made. This information can be recorded into a database and/or compared with other entries on a database (e.g., the amounts of essential and semi-essential amino acids, such as Lysine, Arginine, and/or Histidine, present in samples obtained from nutritionally balanced and/or nutritionally unbalanced subjects) so as to identify whether said subject under analysis has a nutritional imbalance. It is expected that subjects that have a nutritional imbalance will show reduced levels of essential and semi-essential amino acids, in particular Lysine, Arginine, and/or Histidine, compared to subjects that are nutritionally balanced. In some cases, it is expected that a reduction in the levels of Lysine, Arginine, and/or Histidine will be seen prior to a reduction of other essential and semi-essential amino acids. Accordingly, in some embodiments, a subject is identified as having a nutritional imbalance by measuring the amount of Lysine, Arginine, and/or Histidine obtained from a sample from said subject and comparing this amount to the amount of Lysine, Arginine, and/or Histidine present in an individual of the same sex and similar weight, body type, and/or body composition, wherein a reduced amount of Lysine, Arginine, and/or Histidine in the tested subject indicates that said subject has a nutritional imbalance. Once a subject is identified as having a nutritional imbalance, said subject can be provided a dietary supplement, as described herein (e.g., see Example 5). In some embodiments a serving of the dietary supplement can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In some embodiments the dietary supplement is 16.5 grams. In some embodiments, the dietary supplement is provided at least once, twice or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, a proteomic analysis of a sample obtained from said subject under analysis (e.g., cheek cells, cells of the oral cavity, hair, saliva, lacrimal secretion, blood, urine, digestive juice obtained from the stomach, fecal material, or spinal fluid) can be made. As described above, the analysis can include a separation of proteins obtained from said sample (e.g., Isoelectric Focusing and/or 2D gel electrophoresis (IEF followed by SDS-PAGE)) and characterization of the proteins and/or amino acids can be accomplished by conventional techniques (e.g., mass spectroscopy and/or immunolabeling). The results from the post-supplementation measurements can be compared with the pre-supplementation measurements and it will be found that by providing a dietary supplement as described herein (e.g., see Example 5) a subject's nutritional imbalance can be improved. That is, in some embodiments, it is contemplated that nutritional balance as measured by the presence and/or amounts of essential and semi-essential amino acids, in particular Lysine, Arginine, and/or Histidine, can be improved or restored completely by consumption of a dietary supplement, as described herein.

EXAMPLE 8

Body Weight

A subject can be identified as one who is overweight, obese or morbidly obese by survey, questionnaire or clinical or diagnostic techniques that are known in the art. In some embodiments, a subject who is overweight, obese or morbidly obese is identified by BMI, body weight and fat content. Body weight may be identified through use of a gravimetric scale. Fat content may be identified though use of a near infra-red laser. Once a subject is identified as being overweight, obese or morbidly obese, said subject can be provided a dietary supplement, as described herein (e.g., see Example 5). In some embodiments, the dietary supplement is provided at least once, twice or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of the subject can be performed. As explained above, such analysis may include a measurement of BMI, body weight and/or fat content through the procedures described above and/or through clinical or diagnostic procedures known in the art. The results from the post-supplementation measurements can be compared with the pre-supplementation measurements and it will be found that by providing a dietary supplement as described herein (e.g., see Example 5) a subject's BMI, body weight and/or fat content can be improved. That is, in some embodiments, it is contemplated that body weight as measured by BMI, body weight and fat content can be maintained or reduced by consumption of the dietary supplement, as described herein.

As described above in Example 6, subjects were identified by BMI, body weight and/or fat content. They were provided samples of a dietary supplement and then changes in BMI, body weight and/or fat content were measured. Subjects reported that the dietary supplement helped cause significant weight loss and sustained weight control, significant and sustained loss of fat tissue, stimulation of fat burning pathways, a dramatic increase in pep, energy, activity and exercise, an increase in muscle strength and stamina and a natural increase in desire to exercise.

EXAMPLE 9

Beauty Health

Beauty health, as described herein refers to the health of a subject's external appearance, including, for example, a subject's skin, hair, nails, and eyes. A subject can be identified as one who is lacking in beauty health by survey, questionnaire, observation or by clinical or diagnostic techniques known in the art. Once a subject is identified as lacking in beauty health (e.g. unhealthy skin or discolored nails), said subject can be provided a dietary supplement, as described herein (e.g., see Example 5). In some embodiments, the dietary supplement is provided at least once, twice or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of the subject can be performed. As explained above, such analysis may include a survey, questionnaire, or clinical or diagnostic techniques known in the art. The results from the post-supplementation measurements can be compared with the pre-supplementation measurements and it will be found that by providing a dietary supplement as described herein (e.g., see Example 5) a subject's beauty health can be improved. That is, in some embodiments, it is contemplated that beauty health, defined by survey, questionnaire, observation or clinical or diagnostic techniques known in the art can be improved by consumption of the dietary supplement, as described herein.

As described above in Example 6, subjects were identified by BMI, body weight and/or fat content. A questionnaire was provided to them at the beginning of the study to identify any beauty health issues that may be present. Subjects were provided samples of a dietary supplement and other questionnaires were provided at various points during the study. Changes in beauty health of the subjects were measured thereby. Subjects reported an increase in the color and healthy texture of skin, an increase in the health and strength of fingernails and toenails with a removal of discoloration, and an increase in the growth of healthy, shiny, radiant hair. Subjects also reported that hair became thicker, stronger and smoother with more frequent good-hair days and less frequent bad-hair days.

EXAMPLE 10

Mental and Neuromuscular Balance

A subject can be identified as one who is lacking in mental and neuromuscular balance by survey, questionnaire, interview, psychiatric evaluation, reflex evaluation or by clinical or diagnostic techniques known in the art. Once a subject is identified as lacking in mental and neuromuscular balance, said subject can be provided a dietary supplement, as described herein (e.g., see Example 5). In some embodiments, the dietary supplement is provided at least once, twice or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of the subject can be performed. As explained above, such analysis may include a survey, questionnaire, interview, psychiatric evaluation, reflex evaluation or clinical or diagnostic techniques known in the art. The results from the post-supplementation measurements can be compared with the pre-supplementation measurements and it will be found that by providing a dietary supplement as described herein (e.g., see Example 5) a subject's mental and neuromuscular balance can be improved. That is, in some embodiments, it is contemplated that mental and neuromuscular balance, defined by survey, questionnaire, interview, psychiatric evaluation, reflex evaluation or clinical or diagnostic techniques known in the art can be improved by consumption of the dietary supplement, as described herein.

As described above in Example 6, subjects were identified by BMI, body weight and/or fat content. A questionnaire was provided to them at the beginning of the study to identify any mental and neuromuscular balance issues that may be present. Subjects were provided samples of a dietary supplement and other questionnaires were provided at various points during the study. Changes in mental and neuromuscular balance of the subjects were measured. Subjects reported a stabilization of mood swings, a decrease in depression, a decrease in body stress, a more restful sleep, an increase of muscle relaxation and an improved memory capacity.

EXAMPLE 11

Poor Diet

A subject can be identified as one having poor dietary habits by survey, questionnaire, interview, observation or clinical or diagnostic techniques that are known in the art. In some embodiments, the existence of a poor diet in a subject is identified by employing a proteomic analysis of a sample obtained from said subject as described above in Example 7. Once a subject is identified as having poor dietary habits, said subject can be provided a dietary supplement, as described herein (e.g., see Example 5). In some embodiments, the dietary supplement is provided at least once, twice or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, a dietary analysis can be conducted. The results from the post-supplementation measurements can be compared with the pre-supplementation measurements and it will be found that by providing a dietary supplement as described herein (e.g., see Example 5) a subject's poor dietary habits can be improved. That is, in some embodiments, it is contemplated that poor dietary habits can be improved by consumption of a dietary supplement, as described herein.

As described above in Example 6, subjects were identified by BMI, body weight and/or fat content. A questionnaire was provided to them at the beginning of the study to identify any issues of poor dietary habits that may be present. Subjects were provided samples of a dietary supplement and other questionnaires were provided at various points during the study. Changes in dietary habits of the subjects were measured. Subjects reported a shift in desire from low-value foods to high-value foods, a shift in desire away from fast foods, snacks and desserts, a shift in desire away from processed foods containing excess fat, salt and sugar, a decrease in eating frequency and an improvement in portion control.

EXAMPLE 12

Digestive Health

A subject can be identified as one having a digestive heath problem by surveys, questionnaires, medical evaluations or clinical or diagnostic techniques that are known in the art. Once a subject is identified as having a digestive heath problem, said subject can be provided a dietary supplement, as described herein (e.g., see Example 5). In some embodiments, the dietary supplement is provided at least once, twice or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of digestive health can be made. As described above, the analysis can include surveys, questionnaires, medical evaluations or clinical or diagnostic techniques that are known in the art. The results from the post-supplementation measurements can be compared with the pre-supplementation measurements and it will be found that by providing a dietary supplement as described herein (e.g., see Example 5) a subject's digestive health can be improved. That is, in some embodiments, it is contemplated that digestive health problems as measured by surveys, questionnaires, medical evaluations or clinical or diagnostic techniques that are known in the art can be ameliorated or eliminated completely by consumption of a dietary supplement, as described herein.

As described above in Example 6, subjects were identified by BMI, body weight and/or fat content. A questionnaire was provided to them at the beginning of the study to identify any digestive health issues that may be present. Subjects were provided samples of a dietary supplement and other questionnaires were provided at various points during the study. Changes in digestive health of the subjects were measured. Subjects reported a taste adaptation toward high-value foods, an inhibiting of taste adaptation toward low-value foods, including snacks, processed foods and fast foods, an increase in pleasure and taste to the pallets in the oral and pharyngeal cavities, including tongue and throat, respectively, an increase in appetite satisfaction, a reduction in acid reflux and upset stomach, a reduction in stomach bloating, decrease in symptoms of hiatus hernia including heartburn and indigestion, and an increase in bowel movement regularity.

EXAMPLE 13

Immune Health

A subject can be identified as one having an immunocompetency by survey, questionnaire, interview, or clinical or diagnostic techniques that are known in the art. Once a subject is identified as having an immunodeficiency, said subject can be provided a dietary supplement, as described herein (e.g., see Example 5). In some embodiments, the dietary supplement is provided at least once, twice or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of the immunocompetency can be made. As described above, the analysis can include surveys, questionnaires, medical evaluations or clinical or diagnostic techniques that are known in the art. The results from the post-supplementation measurements can be compared with the pre-supplementation measurements and it will be found that by providing a dietary supplement as described herein (e.g., see Example 5) a subject's immunocompetency can be improved. That is, in some embodiments, it is contemplated that immune system as measured by the presence and/or amounts of essential and semi-essential amino acids, in particular Lysine, Arginine, and/or Histidine, can be improved or restored completely by consumption of a dietary supplement, as described herein.

As described above in Example 6, subjects were identified by BMI, body weight and/or fat content. A questionnaire was provided to them at the beginning of the study to identify any immune health issues that may be present. Subjects were provided samples of a dietary supplement and other questionnaires were provided at various points during the study. Changes in immune system health of the subjects were measured. Subjects reported a strengthening of the immune system, an increase in natural resistance to viruses, and increase in natural resistance to fungi, and an increase in natural resistance to bacteria.

EXAMPLE 14

Medical Health

A subject can be identified as one having one or more medical health concerns due to, for example, Type II Diabetes, high blood pressure, high cholesterol or arthritis pain. Such medical health concerns may be identified by survey, questionnaire, interview or clinical or diagnostic techniques that are known in the art. Once a subject is identified as having a medical health concern, said subject can be provided a dietary supplement, as described herein (e.g., see Example 5). In some embodiments, the dietary supplement is provided at least once, twice or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of the one or more medial health concerns can be made. As described above, the analysis can include survey, questionnaire, interview or clinical or diagnostic techniques that are known in the art. The results from the post-supplementation measurements can be compared with the pre-supplementation measurements and it will be found that by providing a dietary supplement as described herein (e.g., see Example 5) a subject's medical health can be improved. That is, in some embodiments, it is contemplated that medical health as measured by the above mentioned techniques can be improved or restored completely by consumption of a dietary supplement, as described herein.

As described above in Example 6, subjects were identified by BMI, body weight and/or fat content. A questionnaire was provided to them at the beginning of the study to identify any medical health issues that may be present. Subjects were provided samples of a dietary supplement and other questionnaires were provided at various points during the study. Changes in medical health of the subjects were measured. Subjects reported a decrease in Type II Diabetes symptoms, a decrease in systolic and diastolic blood pressure, a decrease in total cholesterol and in LDL cholesterol, a decrease in C-reactive protein, a non-specific indicator of inflammation and a decrease in arthritic pain including pain due to osteoarthritis and tendonitis.

EXAMPLE 15

Sexual and Reproductive Health

A subject can be identified as one having poor sexual or reproductive health by survey, questionnaire, interview or clinical or diagnostic techniques that are known in the art. Once a subject is identified as having poor sexual or reproductive health, said subject can be provided a dietary supplement, as described herein (e.g., see Example 5). In some embodiments, the dietary supplement is provided at least once, twice or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of sexual or reproductive health can be made. As described above, the analysis can include one or more surveys, questionnaires, interviews or clinical or diagnostic techniques known in the art. The results from the post-supplementation measurements can be compared with the pre-supplementation measurements and it will be found that by providing a dietary supplement as described herein (e.g., see Example 5) a subject's sexual or reproductive health can be improved. That is, in some embodiments, it is contemplated that sexual or reproductive health can be improved or restored completely by consumption of a dietary supplement, as described herein.

As described above in Example 6, subjects were identified by BMI, body weight and/or fat content. A questionnaire was provided to them at the beginning of the study to identify any sexual or reproductive health issues that may be present. Subjects were provided samples of a dietary supplement and other questionnaires were provided at various points during the study. Changes in sexual or reproductive health of the subjects were measured. Subjects in Examples 2 and 6 reported an increase in sexual desire, an increase in sexual activity, an increase in erectile function, an increase in ejaculate volume, and increases in ovarian health.

EXAMPLE 16

Aging Health

A subject can be identified as one having poor health due to aging by surveys, questionnaires, interviews or clinical or diagnostic techniques that are known in the art. Once a subject is identified as having age-related health concerns, said subject can be provided a dietary supplement, as described herein (e.g., see Example 5). In some embodiments, the dietary supplement is provided at least once, twice or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of the age-related health concerns can be made. As described above, the analysis can include one or more surveys, questionnaires, interviews or clinical or diagnostic techniques that are known in the art. The results from the post-supplementation measurements can be compared with the pre-supplementation measurements and it will be found that by providing a dietary supplement as described herein (e.g., see Example 5) a subject's poor health due to age can be improved. That is, in some embodiments, it is contemplated that poor health due to age can be improved or restored completely by consumption of a dietary supplement, as described herein.

As described above in Example 6, subjects were identified by BMI, body weight and/or fat content. A questionnaire was provided to them at the beginning of the study to identify any age-related health issues that may be present. Subjects were provided samples of a dietary supplement and other questionnaires were provided at various points during the study. Changes in age-related health of the subjects were measured. Subjects in Examples 2 and 6 reported an absence of tired, weak and sluggish feelings, a decrease in functional age, an increase in aging performance and a prevention of age-related diseases (thus indicating an increase in longevity that turns back the hands of time and promotes youth).

EXAMPLE 17

Addiction Health

A subject can be identified as one having one or more dependencies or addictions by surveys, questionnaires, interviews or clinical or diagnostic techniques that are known in the art. Once a subject is identified as having an addiction, said subject can be provided a dietary supplement, as described herein (e.g., see Example 5). In some embodiments, the dietary supplement is provided at least once, twice or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of the addiction can be made. As described above, the analysis can include one or more surveys, questionnaires, interviews or clinical or diagnostic techniques that are known in the art. The results from the post-supplementation measurements can be compared with the pre-supplementation measurements and it will be found that by providing a dietary supplement as described herein (e.g., see Example 5) a subject's addiction can be lessened and/or eliminated. That is, in some embodiments, it is contemplated that addictions as measured by the methods listed above can be lessened or eliminated completely by consumption of a dietary supplement, as described herein.

As described above in Example 6, subjects were identified by BMI, body weight and/or fat content. A questionnaire was provided to them at the beginning of the study to identify any addiction health issues that may be present. Subjects were provided samples of a dietary supplement and other questionnaires were provided at various points during the study. Changes in addiction health of the subjects were measured. Subjects reported decreases in food addictions, decreases in sugar, fat and salt addictions, decreases in caffeine addictions, decreases in smoking addictions and decreases in drug addictions. Additionally, subjects reported an acceleration of recovery from alcohol toxicity (hangovers).

EXAMPLE 18

Oral Formulations Containing the Power Amino Acid Complex Causes Weight Loss in Overweight or Obese Subjects The Power Amino Acid Complex comprises L-Lysine and/or L-Arginine and, in addition, at least one (1) amino acid selected from L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan). These amino acids are critical building blocks for enzymatic reactions in the body and are typically not provided at adequate levels in the diet. Supplementation of the Power Amino Acid Complex to the exclusion of others (consisting essentially of L-Lysine, L-Arginine, L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan)) can improve the health and well-being of a subject and provide the therapeutic benefits described herein. That is, it has been discovered that the Power Amino Acid Complex can be manufactured in many different formulations, and other amino acids or proteins are not required to receive a benefit.

One formulation of the Power Amino Acid Complex is oral. In particular, liquid formulations such as water (including variations of water such as Penta® Water) or various juices, with or without vitamins or other added supplements, may be used as the solvent with which the Power Amino Acid Complex is formulated. Other ingredients can comprise guar gum, lecithin, natural and artificial flavors, natural and artificial colors, fructo-oligosaccharide, and natural and artificial sweeteners. By providing the rate limiting amino acids, the Power Amino Acid Complex in water, for example, one can obtain the supplement and therapeutic benefits of the power amino acids while maintaining a low calorie intake.

In some embodiments a serving of the Power Amino Acid Complex can be less than, greater than, at least, or any number in between 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In one embodiment, a 2.2 g serving of the Power Amino Acid Complex contains amounts of each free-form power amino acid listed in Table 4.

TABLE 4

| L-Arginine HCl | 500 mg |
|---|---|
| L-Lysine HCl | 500 mg |
| L-Isoleucine | 100 mg |
| dl-Phenylalanine (or L-Phenylalanine) | 100 mg |
| L-Methionine | 100 mg |
| L-Leucine | 100 mg |
| L-Valine | 100 mg |
| L-Threonine | 100 mg |
| L-Histidine HCl | 500 mg |
| 5-Hydroxy Tryptophan (or L-Hydroxy Tryptophan or L-Tryptophan) | 100 mg |

TABLE 5

| L-Alanine | 660 mg |
|---|---|
| L-Aspartic Acid | 1103 mg |
| L-Glutamic Acid | 1775 mg |
| L-Cystine | 205 mg |
| L-Glycine | 180 mg |
| L-Serine | 450 mg |
| L-Proline | 620 mg |
| L-Tyrosine | 270 mg |
| Taurine | 200 mg |

A subject can be identified as one who is overweight, obese, or morbidly obese by surveys, questionnaires, interviews, or clinical or diagnostic techniques that are known in the art. In some embodiments, a subject who is overweight, obese, or morbidly obese is identified by BMI, body weight, and fat content. Body weight may be identified through use of a gravimetric scale. Fat content may be identified through use of a near infra-red laser. Once a subject is identified as being overweight, obese, or morbidly obese, said subject will be given the Power Amino Acid Complex. In some embodiments, the Power Amino Acid Complex is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. Subjects are measured for body weight and fat content with devices such as a gravimetric scale and a near infra-red laser, respectively. Measurements may also include one or more surveys, questionnaires, interviews, or clinical or diagnostic techniques that are known in the art. The results from the post-supplementation measurements can be compared with the pre-supplementation measurements. It will be found that the subjects' BMI, weight, and/or fat content who received the Power Amino Acid Complex are improved compared to the subjects who did not receive the Power Amino Acid Complex. One would expect to find improvements such as a reduction in weight and/or a decrease in fat content. That is, in some embodiments, it is contemplated that a subject's BMI, body weight, and/or fat content can be improved or restored completely by consumption of a dietary supplement, as described herein.

In another embodiment, the Power Amino Acid Complex may be formulated with the Factor-4 Protein Complex plus other non-essential amino acids and nutrients referred to as Factor-4. By formulating the Power Amino Acid Complex with the Factor-4 Protein Complex as well as other nutrients, vitamins, and non-essential amino acids, one can obtain the therapeutic benefits of the Power Amino Acid Complex that the Factor-4 Protein Complex, non-essential amino acids, vitamins, and other nutrients alone do not provide.

In one embodiment, a dietary supplement is composed of a powder which comprises the Factor-4 dietary supplement described in Tables 2 and 3. In another embodiment, a dietary supplement, Factor-4 minus the Power Amino Acid Complex ("Factor-4(−)"), is composed of a powder which is comprised of the elements described in Tables 2 and 5. In some embodiments, a serving of the dietary supplements can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In an embodiment, a 16.5 g serving of Factor-4 or Factor-4(−) will provide amounts of each element as described in Tables 2 and 3 and Tables 2 and 5, respectively.

A subject can be identified as one who is overweight, obese, or morbidly obese by surveys, questionnaires, interviews, or clinical or diagnostic techniques that are known in the art. In some embodiments, a subject who is overweight, obese, or morbidly obese is identified by BMI, body weight, and fat content. Body weight may be identified through use of a gravimetric scale. Fat content may be identified through use of a near infra-red laser. Once a subject is identified as being overweight, obese, or morbidly obese, said subject will be given Factor-4 and Factor-4(−). In some embodiments, Factor-4(−) is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. During the period in which subjects are receiving Factor-4(−), subjects are measured for body weight and fat content with devices such as a gravimetric scale and a near infra-red laser, respectively. Subjects are then switched to Factor-4 (the supplement that contains the Power Amino Acid Complex) for the remainder of the evaluation period. At various points during the period when subjects are receiving Factor-4, subjects are measured again by body weight and fat content. Measurements for both regimens (Factor-4 and Factor-4(−)) may also include one or more surveys, questionnaires, interviews, or clinical or diagnostic techniques that are known in the art. The results from subjects who received supplementation with Factor-4(−) and Factor-4 can be compared. It will be found that the subjects' BMI, weight, and/or fat content who received the Power Amino Acid Complex-containing formulation (i.e., Factor-4) are improved compared to the subjects who did not receive the Power Amino Acid Complex (i.e., Factor-4(−)). One would expect to find improvements such as a reduction in weight and/or a decrease in fat content. That is, in some embodiments, it is contemplated that a subject's BMI, body weight, and/or fat content can be improved or restored completely by consumption of a dietary supplement, as described herein.

EXAMPLE 19

Oral Formulations Containing The Power Amino Acid Complex Improves Nutritional Imbalance The Power Amino Acid Complex comprises L-Lysine and/or L-Arginine and, in addition, at least one (1) amino acid selected from L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan). These amino acids are critical building blocks for enzymatic reactions in the body and are typically not provided at adequate levels in the diet. Supplementation of the Power Amino Acid Complex to the exclusion of others (consisting essentially of L-Lysine, L-Arginine, L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan)) can improve the health and well-being of a subject and provide the therapeutic benefits described herein. That is, it has been discovered that the Power Amino Acid Complex can be manufactured in many different formulations, and other amino acids or proteins are not required to receive a benefit.

One formulation of the Power Amino Acid Complex is oral. In particular, liquid formulations such as water (including variations of water such as Penta® Water) or various juices, with or without vitamins or other added supplements, may be used as the solvent with which the Power Amino Acid Complex is formulated. Other ingredients can comprise guar gum, lecithin, natural and artificial flavors, natural and artificial colors, fructo-oligosaccharide, and natural and artificial sweeteners. By providing the rate limiting amino acids, the Power Amino Acid Complex in water, for example, one can obtain the supplement and therapeutic benefits of the power amino acids while maintaining a low calorie intake.

In some embodiments a serving of the Power Amino Acid Complex can be less than, greater than, at least, or any number in between 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In one embodiment, a 2.2 g serving of the Power Amino Acid Complex contains amounts of each free-form power amino acid listed in Table 4.

A subject can be identified as having a nutritional imbalance by surveys, questionnaires, interviews, or clinical or diagnostic techniques that are known in the art. In some embodiments, a subject who has a nutritional imbalance can be identified by employing a proteomic analysis of a sample obtained from said subject (e.g., cheek cells, cells of the oral cavity, hair, saliva, lacrimal secretion, blood, urine, digestive juice obtained from the stomach, fecal material, or spinal fluid). The proteomic analysis can include a separation of proteins obtained from said sample (e.g., Isoelectric Focusing and/or 2D gel electrophoresis (IEF followed by SDS-PAGE)) and characterization of the proteins and/or amino acids can be accomplished by conventional techniques (e.g., mass spectroscopy, immunolabeling, and/or staining followed by visual and/or computer-assisted analysis). In some embodiments, an analysis and measurement of the amount and/or presence of one or more essential and semi-essential amino acids, in particular a positively charged amino acid (e.g., Lysine, Arginine, and/or Histidine), is made. This information can be recorded into a database and/or compared with other entries on a database (e.g., the amounts of essential and semi-essential amino acids, such as Lysine, Arginine, and/or Histidine, present in samples obtained from nutritionally balanced and/or nutritionally unbalanced subjects) so as to identify whether said subject under analysis has a nutritional imbalance. It is expected that subjects that have a nutritional imbalance will show reduced levels of essential and semi-essential amino acids, in particular Lysine, Arginine, and/or Histidine, compared to subjects that are nutritionally balanced. In some cases, it is expected that a reduction in the levels of Lysine, Arginine, and/or Histidine will be seen prior to a reduction of other essential and semi-essential amino acids. Accordingly, in some embodiments, a subject is identified as having a nutritional imbalance by measuring the amount of Lysine, Arginine, and/or Histidine obtained from a sample from said subject and comparing this amount to the amount of Lysine, Arginine, and/or Histidine present in an individual of the same sex and similar weight, body type, and/or body composition, wherein a reduced amount of Lysine, Arginine, and/or Histidine in the tested subject indicates that said subject has a nutritional imbalance. In another embodiment, other techniques known to a person having ordinary skill in the art can be used to separate proteins by their isoelectric points such as Isoelectric Focusing, affinity columns, or high pressure liquid chromatography. Using such procedures on said sample, a measurement of pre-determined positively- and negatively-charged proteins can be taken before and after supplementation. Measurements may reflect the absolute concentrations of positively- and negatively-charged proteins or be represented as a ratio of positively- to negatively-charged proteins. In some embodiments, an analysis and measurement of the amount of positively- and negatively-charged proteins is made. This information can be recorded into a database and/or compared with other entries on a database (e.g., the amounts and/or ratios of positively- and negatively-charged proteins present in samples obtained from nutritionally balanced and/or nutritionally unbalanced subjects) so as to identify whether said subject under analysis has a nutritional imbalance. It is expected that subjects that have a nutritional imbalance will show reduced levels of positively-charged proteins compared to subjects that are nutritionally balanced. In some cases, it is expected that a reduction in the levels of positively-charged proteins will be seen prior to a reduction of other neutral and negatively-charged proteins. Accordingly, in some embodiments, a subject is identified as having a nutritional imbalance by measuring the concentration of positively-charged proteins or by measuring the ratio of positively- to negatively-charged proteins obtained from a sample from said subject and comparing these concentrations and/or ratios to an individual of the same sex and similar weight, body type, and/or body composition, wherein a reduced amount and/or ratio of positively-charged proteins in the tested subject indicates that said subject has a nutritional imbalance. Once a subject is identified as having a nutritional imbalance, said subjects will be given the Power Amino Acid Complex. In some embodiments, the Power Amino Acid Complex is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. During the period in which subjects are receiving the Power Amino Acid Complex, a proteomic profile can be assessed through measurements of a sample obtained from said subjects (e.g., cheek cells, cells of the oral cavity, hair, saliva, lacrimal secretion, blood, urine, digestive juice obtained from the stomach, fecal material, or spinal fluid). As described above, the measurements and subsequent analysis can include a separation of proteins obtained from said sample (e.g., Isoelectric Focusing and/or 2D gel electrophoresis (IEF followed by SDS-PAGE)) and characterization of the proteins and/or amino acids can be accomplished by conventional techniques (e.g., mass spectroscopy and/or immunolabeling). Measurements may also include one or more surveys, questionnaires, interviews, or clinical or diagnostic techniques that are known in the art. The results from the post-supplementation measurements can be compared with the pre-supplementation measurements. It will be found that the subjects' nutritional imbalance who received the Power Amino Acid Complex is improved compared to the subjects who did not receive the Power Amino Acid Complex. That is, in some embodiments, it is contemplated that nutritional balance as measured by the presence and/or amounts of essential and semi-essential amino acids, in particular Lysine, Arginine, and/or Histidine, can be improved or restored completely by consumption of a dietary supplement, as described herein.

In another embodiment, the Power Amino Acid Complex may be formulated with the Factor-4 Protein Complex plus other non-essential amino acids and nutrients referred to as Factor-4. By formulating the Power Amino Acid Complex with the Factor-4 Protein Complex as well as other nutrients, vitamins, and non-essential amino acids, one can obtain the therapeutic benefits of the Power Amino Acid Complex that the Factor-4 Protein Complex, non-essential amino acids, vitamins, and other nutrients alone do not provide.

In one embodiment, a dietary supplement is composed of a powder which comprises the Factor-4 dietary supplement described in Tables 2 and 3. In another embodiment, a dietary supplement, Factor-4 minus the Power Amino Acid Complex ("Factor-4(−)"), is composed of a powder which is comprised of the elements described in Tables 2 and 5. In some embodiments, a serving of the dietary supplements can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In an embodiment, a 16.5 g serving of Factor-4 or Factor-4(−) will provide amounts of each element as described in Tables 2 and 3 and Tables 2 and 5, respectively.

A subject can be identified as having a nutritional imbalance by surveys, questionnaires, interviews, or clinical or diagnostic techniques that are known in the art. In some embodiments, a subject who has a nutritional imbalance can be identified by employing a proteomic analysis of a sample obtained from said subject (e.g., cheek cells, cells of the oral cavity, hair, saliva, lacrimal secretion, blood, urine, digestive juice obtained from the stomach, fecal material, or spinal fluid). As described above, the measurements and subsequent analysis can include a separation of proteins obtained from said sample (e.g., Isoelectric Focusing and/or 2D gel electrophoresis (IEF followed by SDS-PAGE)) and characterization of the proteins and/or amino acids can be accomplished by conventional techniques (e.g., mass spectroscopy, immunolabeling, and/or staining followed by visual and/or computer-assisted analysis). In some embodiments, an analysis and measurement of the amount and/or presence of one or more essential and semi-essential amino acids, in particular a positively charged amino acid (e.g., Lysine, Arginine, and/or Histidine), is made. This information can be recorded into a database and/or compared with other entries on a database (e.g., the amounts of essential and semi-essential amino acids, such as Lysine, Arginine, and/or Histidine, present in samples obtained from nutritionally balanced and/or nutritionally unbalanced subjects) so as to identify whether said subject under analysis has a nutritional imbalance. It is expected that subjects that have a nutritional imbalance will show reduced levels of essential and semi-essential amino acids, in particular Lysine, Arginine, and/or Histidine, compared to subjects that are nutritionally balanced. In some cases, it is expected that a reduction in the levels of Lysine, Arginine, and/or Histidine will be seen prior to a reduction of other essential and semi-essential amino acids. Accordingly, in some embodiments, a subject is identified as having a nutritional imbalance by measuring the amount of Lysine, Arginine, and/or Histidine obtained from a sample from said subject and comparing this amount to the amount of Lysine, Arginine, and/or Histidine present in an individual of the same sex and similar weight, body type, and/or body composition, wherein a reduced amount of Lysine, Arginine, and/or Histidine in the tested subject indicates that said subject has a nutritional imbalance. In another embodiment, other techniques known to a person having ordinary skill in the art can be used to separate proteins by their isoelectric points such as Isoelectric Focusing, affinity columns, or high pressure liquid chromatography. Using such procedures on said sample, a measurement of pre-determined positively- and negatively-charged proteins can be taken before and after supplementation. Measurements may reflect the absolute concentrations of positively- and negatively-charged proteins or be represented as a ratio of positively- to negatively-charged proteins. In some embodiments, an analysis and measurement of the amount of positively- and negatively-charged proteins is made. This information can be recorded into a database and/or compared with other entries on a database (e.g., the amounts and/or ratios of positively- and negatively-charged proteins present in samples obtained from nutritionally balanced and/or nutritionally unbalanced subjects) so as to identify whether said subject under analysis has a nutritional imbalance. It is expected that subjects that have a nutritional imbalance will show reduced levels of positively-charged proteins compared to subjects that are nutritionally balanced. In some cases, it is expected that a reduction in the levels of positively-charged proteins will be seen prior to a reduction of other neutral and negatively-charged proteins. Accordingly, in some embodiments, a subject is identified as having a nutritional imbalance by measuring the concentration of positively-charged proteins or by measuring the ratio of positively- to negatively-charged proteins obtained from a sample from said subject and comparing these concentrations and/or ratios to an individual of the same sex and similar weight, body type, and/or body composition, wherein a reduced amount and/or ratio of positively-charged proteins in the tested subject indicates that said subject has a nutritional imbalance. Once a subject is identified as having a nutritional imbalance, said subject will be given Factor-4 and Factor-4 (–). In some embodiments, Factor-4(–) is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. During the period in which subjects are receiving Factor-4(–), a proteomic profile can be assessed through measurements of a sample obtained from said subject (e.g., cheek cells, cells of the oral cavity, hair, saliva, lacrimal secretion, blood, urine, digestive juice obtained from the stomach, fecal material, or spinal fluid). Subjects are then switched to Factor-4 (the supplement that contains the Power Amino Acid Complex) for the remainder of the evaluation period. At various points during the period when subjects are receiving Factor-4, subjects are measured again by proteomic analysis as described above including techniques such as Isoelectric Focusing and/or 2D gel electrophoresis (IEF followed by SDS-PAGE), mass spectroscopy, immunolabeling, staining followed by visual and/or computer-assistance, and measuring the amount and/or presence of particular amino acids. Measurements for both regimens (Factor-4 and Factor-4(–)) may also include one or more surveys, questionnaires, interviews, or clinical or diagnostic techniques that are known in the art. The results from subjects who received supplementation with Factor-4(–) and Factor-4 can be compared. It will be found that the subjects' nutritional imbalance who received the Power Amino Acid Complex-containing formulation (i.e., Factor-4) is improved compared to the subjects who did not receive the Power Amino Acid Complex (i.e., Factor-4(–)). That is, in some embodiments, it is contemplated that nutritional balance as measured by the presence and/or amounts of essential and semi-essential amino acids, in particular Lysine, Arginine, and/or Histidine, can be improved or restored completely by consumption of a dietary supplement, as described herein.

EXAMPLE 20

Oral Formulations Containing the Power Amino Acid Complex Improves Beauty Health The Power Amino Acid Complex comprises L-Lysine and/or L-Arginine and, in addition, at least one (1) amino acid selected from L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan). These amino acids are critical building blocks for enzymatic reactions in the body and are typically not provided at adequate levels in the diet. Supplementation of the Power Amino Acid Complex to the exclusion of others (consisting essentially of L-Lysine, L-Arginine, L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan)) can improve the health and well-being of a subject and provide the therapeutic benefits described herein. That is, it has been discovered that the Power Amino Acid Complex can be manufactured in many different formulations, and other amino acids or proteins are not required to receive a benefit.

One formulation of the Power Amino Acid Complex is oral. In particular, liquid formulations such as water (including variations of water such as Penta® Water) or various juices, with or without vitamins or other added supplements, may be used as the solvent with which the Power Amino Acid Complex is formulated. Other ingredients can comprise guar gum, lecithin, natural and artificial flavors, natural and artificial colors, fructo-oligosaccharide, and natural and artificial sweeteners. By providing the rate limiting amino acids, the Power Amino Acid Complex in water, for example, one can obtain the supplement and therapeutic benefits of the power amino acids while maintaining a low calorie intake.

In some embodiments a serving of the Power Amino Acid Complex can be less than, greater than, at least, or any number in between 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In one embodiment, a 2.2 g serving of the Power Amino Acid Complex contains amounts of each free-form power amino acid listed in Table 4.

A subject can be identified as having poor skin health and/or appearance by surveys, questionnaires, interviews, or clinical or diagnostic techniques that are known in the art. In some embodiments, a subject with poor skin health and/or appearance can be identified by evaluation of wrinkles, fine-line wrinkles, skin smoothness, skin moisturization, cellulite, age spots, acne, and elasticity/toneness. Identification of wrinkles (including fine-line wrinkles) can be accomplished by assessing the topography of the skin through visual and/or photographic means. Photographic devices, such as Clarity™ Pro, use white and UV lights to capture images of the skin. A computer furnished with analytical software may be used with said camera to analyze the condition of the skin and provide a quantitative measurement of skin attributes such as depth and width of wrinkles, skin tone, pore quantity and pore size, and UV damage. Another common technique for identifying and measuring wrinkles includes profilometry. Profilometry requires first making replicas of the skin (performed commonly with silica) followed by an evaluation of the skin mold. There are several different profilometry techniques known in the art including mechanical, optical, and transparency. Ultrasonography is another technique that may be used in wrinkle evaluation. Use of a high-resolution three-dimensional laser surface scanner to quantify skin surface morphology is yet another identification and measurement tool available. To identify the smoothness of subjects' skin, most of these techniques may also be utilized. Likewise, cellulite can be identified with most of the techniques aforementioned including photography, profilometry, and ultrasonography. Subjects with poor skin elasticity can be identified with a Cutometer® and/or Reviscometer®. Suboptimal skin moisturization may be identified by evaporimetry and comeometry. Age spots can be identified by photographic means with the assistance of a colorimeter such as the Konica Minolta Colorimeters. Acne can be identified by the Leeds technique and serum cyproterone acetate concentrations. The number and size of pores is another parameter to identify acne. The topographic evaluation techniques aforementioned are also used commonly to assess the number and size of pores. Biochemical evaluation of the pores' content may also be performed to identify acne. Many of these techniques overlap and may be used for identifying most of the problematic skin features listed herein. Once a subject is identified as having poor skin health and/or appearance, said subject will be given the Power Amino Acid Complex. In some embodiments, the Power Amino Acid Complex is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. During the period in which subjects are receiving the Power Amino Acid Complex, subjects are measured for wrinkles, fine-line wrinkles, skin smoothness, skin moisturization, cellulite, age spots, acne, and elasticity/toneness. Measurements may also include one or more surveys, questionnaires, interviews, or clinical or diagnostic techniques that are known in the art. As described above, measurements aimed to quantify characteristics of the skin can include a variety of topography-based methods. Measurements of wrinkles, fine-lines, skin smoothness, and cellulite can be accomplished with photography using white and UV lights. Computer software attached to said photography device provides means to quantify features of skin aberrations such as the number and severity of wrinkles. Measurements for topographic skin features may include measuring the depth and width of wrinkles. Other measuring techniques include optical, mechanical, and/or transparency profilometry measurements. Ultrasonography and laser surface scanners may also be employed for skin surface morphology measurements. Elasticity of subjects' skin can be measured with a Cutometer® and/or Reviscometer®. For skin moisturization measurements, evaporimetry and/or comeometry can be used. Age spots can be measured by photographic means with the assistance of a colorimeter such as the Konica Minolta Colorimeters. Acne measurements may be taken by the Leeds technique and serum cyproterone acetate concentrations. Measurements of pore number, size, and/or their content may be taken. The results from the post-supplementation measurements can be compared with the pre-supplementation measurements. It will be found that the subjects' skin health and/or appearance who received the Power Amino Acid Complex are improved compared to the subjects who did not receive the Power Amino Acid Complex. One would expect to find improvements such as reduced depth and width of wrinkles and pores, skin that is smoother and less dry, reduced cellulite, reduced acne, tighter skin, and less color variation. That is, in some embodiments, it is contemplated that skin health and/or appearance can be improved or restored completely by consumption of a dietary supplement, as described herein.

In another embodiment, the Power Amino Acid Complex may be formulated with the Factor-4 Protein Complex plus other non-essential amino acids and nutrients referred to as Factor-4. By formulating the Power Amino Acid Complex with the Factor-4 Protein Complex as well as other nutrients, vitamins, and non-essential amino acids, one can obtain the therapeutic benefits of the Power Amino Acid Complex that the Factor-4 Protein Complex, non-essential amino acids, vitamins, and other nutrients alone do not provide.

In one embodiment, a dietary supplement is composed of a powder which comprises the Factor-4 dietary supplement described in Tables 2 and 3. In another embodiment, a dietary supplement, Factor-4 minus the Power Amino Acid Complex ("Factor-4(−)"), is composed of a powder which is comprised of the elements described in Tables 2 and 5. In some embodiments, a serving of the dietary supplements can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In an embodiment, a 16.5 g serving of Factor-4 or Factor-4(−) will provide amounts of each element as described in Tables 2 and 3 and Tables 2 and 5, respectively.

A subject can be identified as having poor skin health and/or appearance by surveys, questionnaires, interviews, or clinical or diagnostic techniques that are known in the art. In some embodiments, a subject with poor skin health and/or appearance can be identified by evaluation of wrinkles, fine-line wrinkles, skin smoothness, skin moisturization, cellulite, age spots, acne, and elasticity/toneness. Identification of wrinkles (including fine-line wrinkles) can be accomplished by assessing the topography of the skin through visual and/or photographic means. Photographic devices, such as ClarityPro, use white and UV lights to capture images of the skin. A computer furnished with analytical software may be used with said camera to analyze the condition of the skin and provide a quantitative measurement of skin attributes such as depth and width of wrinkles, skin tone, pore quantity and pore size, and UV damage. Another common technique for identifying and measuring wrinkles includes profilometry. Profilometry requires first making replicas of the skin (performed commonly with silica) followed by an evaluation of the skin mold. There are several different profilometry techniques known in the art including mechanical, optical, and transparency. Ultrasonography is another technique that may be used in wrinkle evaluation. Use of a high-resolution three-dimensional laser surface scanner to quantify skin surface morphology is yet another identification and measurement tool available. To identify the smoothness of subjects' skin, most of these techniques may also be utilized. Likewise, cellulite can be identified with most of the techniques aforementioned including photography, profilometry, and ultrasonography. Subjects with poor skin elasticity can be identified with a CUTOMETER® (Trademark of COURAGE+KHAZAKA ELECTRONIC GMBH CORPORATION, Koln, Germany) and/or Reviscometer. Suboptimal skin moisturization may be identified by evaporimetry and comeometry. Age spots can be identified by photographic means with the assistance of a colorimeter such as the Konica Minolta Colorimeters. Acne can be identified by the Leeds technique and serum cyproterone acetate concentrations. The number and size of pores is another parameter to identify acne. The topographic evaluation techniques aforementioned are also used commonly to assess the number and size of pores. Biochemical evaluation of the pores' content may also be performed to identify acne. Many of these techniques overlap and may be used for identifying most of the problematic skin features listed herein. Once a subject is identified as having poor skin health and/or appearance, said subject will be given Factor-4 and Factor-4 (−). In some embodiments, Factor-4(−) is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. During the period in which subjects are receiving Factor-4(−), subjects are measured for wrinkles, fine-line wrinkles, skin smoothness, skin moisturization, cellulite, age spots, acne, and elasticity/toneness. As described above, measurements aimed to quantify characteristics of the skin can include a variety of topography-based methods. Measurements of wrinkles, fine-lines, skin smoothness, and cellulite can be accomplished with photography using white and UV lights. Computer software attached to said photography device provides means to quantify features of skin aberrations such as the number and severity of wrinkles. Measurements for topographic skin features may include measuring the depth and width of wrinkles. Other measuring techniques include optical, mechanical, and/or transparency profilometry measurements. Ultrasonography and laser surface scanners may also be employed for skin surface morphology measurements. Elasticity of subjects' skin can be measured with a CUTOMETER® and/or Reviscometer. For skin moisturization measurements, evaporimetry and/or comeometry can be used. Age spots can be measured by photographic means with the assistance of a colorimeter such as the Konica Minolta Colorimeters. Acne measurements may be taken by the Leeds technique and serum cyproterone acetate concentrations. Measurements of pore number, size, and/or their content may be taken. Subjects are then switched to Factor-4 (the supplement that contains the Power Amino Acid Complex) for the remainder of the evaluation period. At various points during the period when subjects are receiving Factor-4, subjects are measured again for wrinkles, fine-line wrinkles, skin smoothness, skin moisturization, cellulite, age spots, acne, and elasticity/toneness. As described above, measurements can include a variety of topography-based methods including profilometry and ultrasonography. Age spots, elasticity, and moisturization measurements can be taken with a colorimeter, CUTOMETER® and/or Reviscometer, and evaporimeter and/or comeometer, respectively. Measurements for both regimens (Factor-4 and Factor-4(−)) may also include one or more surveys, questionnaires, interviews, or clinical or diagnostic techniques that are known in the art. The results from subjects who received supplementation with Factor-4(−) and Factor-4 can be compared. It will be found that the subjects' skin health and/or appearance who received the Power Amino Acid Complex-containing formulation (i.e., Factor-4) is improved compared to the subjects who did not receive the Power Amino Acid Complex (i.e., Factor-4(−)). One would expect to find improvements such as reduced depth and width of wrinkles and pores, skin that is smoother and less dry, reduced cellulite, reduced acne, tighter skin, and less color variation. That is, in some embodiments, it is contemplated that skin health and/or appearance can be improved or restored completely by consumption of a dietary supplement, as described herein.

In another embodiment, a subject can be identified as having unhealthy, thin, unappealing and/or damaged hair by surveys, questionnaires, interviews, or clinical or diagnostic techniques that are known in the art. In some embodiments, a subject with unhealthy and/or damaged hair can be identified by evaluation of combability, strength, thickness, porosity, split ends, hair shine, amino acid composition, lipid content, alkaline solubility, copper uptake, and discoloration. Identification of poor combability can be assessed by the combing force. Tensile and flexabrasion testing can identify weak hair. Identification of thin hair, hair porosity, and split ends can be accomplished with a scanning electron microscope and/or other microscopy imaging. Identifying hair lacking in shine may be achieved with a photogoniometer and/or other imaging analyses. Identifying hair with substandard amino acid and lipid compositions can be carried out by common techniques known in the art such as using spectrophotometric-, calorimetric-, or chromatographic-based assays. Alkaline soluble hair can be identified by assessing the hairs' rate of solubility in the presence of non-acidic (i.e., basic) solvents. The copper uptake of hair is another identifying hallmark of hair quality. Identifying said subjects can be accomplished by copper absorbent techniques such as colorimetric-based techniques. Colorimetric techniques may also identify discolored hair. Once a subject is identified as having unhealthy, thin, unappealing and/or damaged hair, said subject will be given the Power Amino Acid Complex. In some embodiments, the Power Amino Acid Complex is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. During the period in which subjects are receiving the Power Amino Acid Complex, subjects are measured for combability, strength, thickness, porosity, split ends, hair shine, amino acid composition, lipid content, alkaline solubility, copper uptake, and discoloration. Measurements may also include one or more surveys, questionnaires, interviews, or clinical or diagnostic techniques that are known in the art. As described above, measurements for combability can be taken by changes in combing force. Hair thickness, porosity, and split ends may be measured with a scanning electron microscope and/or other microscopic imaging. Hair strength can be measured by tensile and flexabrasion testing. Photogoniometric measurements can be taken to assess hair shine. The hairs' amino acid and lipid compositions can be measured by a number of common techniques known in the art such as chromatography. Measurements for its alkaline solubility may be determined by its solubility rate in the presence of a base. A subject's hairs' copper uptake may be assessed calorimetrically by measuring the remaining copper in a vial after incubating the subjects' hair in a copper-based solution. Discoloration measurements can be taken with various reflectometer devices using parameters such as the Commission International d'Eclairage (CIE) L*a*b* system. Said reflectometer devices may include the Photovolt ColorWalk (a tristimulus calorimeter) and/or the DermaSpectrometer (a narrow-band reflectometer). Other spectrometric and/or calorimetric devices may be employed. The results from the post-supplementation measurements can be compared with the pre-supplementation measurements. It will be found that the subjects' hair health and/or appearance who received the Power Amino Acid Complex are improved compared to the subjects who did not receive the Power Amino Acid Complex. One would expect to find improvements such as an increase in hair strength, an increase in hair thickness, a decrease in porosity, a reduction of split ends, an increase in shine, an increase of amino acids and lipids, a decrease in thiol content, a decrease in alkaline solubility, a decrease in copper uptake, and a reduction in color loss/fading. That is, in some embodiments, it is contemplated that hair health and/or appearance can be improved or restored completely by consumption of a dietary supplement, as described herein.

In another embodiment, the Power Amino Acid Complex may be formulated with the Factor-4 Protein Complex plus other non-essential amino acids and nutrients referred to as Factor-4. By formulating the Power Amino Acid Complex with the Factor-4 Protein Complex as well as other nutrients, vitamins, and non-essential amino acids, one can obtain the therapeutic benefits of the Power Amino Acid Complex that the Factor-4 Protein Complex, non-essential amino acids, vitamins, and other nutrients alone do not provide.

In one embodiment, a dietary supplement is composed of a powder which comprises the Factor-4 dietary supplement described in Tables 2 and 3. In another embodiment, a dietary supplement, Factor-4 minus the Power Amino Acid Complex ("Factor-4(−)"), is composed of a powder which is comprised of the elements described in Tables 2 and 5. In some embodiments, a serving of the dietary supplements can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In an embodiment, a 16.5 g serving of Factor-4 or Factor-4(−) will provide amounts of each element as described in Tables 2 and 3 and Tables 2 and 5, respectively.

A subject can be identified as having unhealthy, thin, unappealing and/or damaged hair by surveys, questionnaires, interviews, or clinical or diagnostic techniques that are known in the art. In some embodiments, a subject with unhealthy and/or damaged hair can be identified by evaluation of combability, strength, thickness, porosity, split ends, hair shine, amino acid composition, lipid content, alkaline solubility, copper uptake, and discoloration. Identification of poor combability can be assessed by the combing force. Tensile and flexabrasion testing can identify weak hair. Identification of thin hair, hair porosity, and split ends can be accomplished with a scanning electron microscope and/or other microscopy imaging. Identifying hair lacking in shine may be achieved with a photogoniometer and/or other imaging analyses. Identifying hair with substandard amino acid and lipid compositions can be carried out by common techniques known in the art such as using spectrophotometric-, calorimetric-, or chromatographic-based assays. Alkaline soluble hair can be identified by assessing the hairs' rate of solubility in the presence of non-acidic (i.e., basic) solvents. The copper uptake of hair is another identifying hallmark of hair quality. Identifying said subjects can be accomplished by copper absorbent techniques such as colorimetric-based techniques. Colorimetric techniques may also identify discolored hair. Once a subject is identified as having unhealthy, thin, unappealing and/or damaged hair, said subject will be given Factor-4 and Factor-4(−). In some embodiments, Factor-4(−) is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. During the period in which subjects are receiving Factor-4(−), subjects are measured for combability, strength, thickness, porosity, split ends, hair shine, amino acid composition, lipid content, alkaline solubility, copper uptake, and discoloration. As described above, measurements for combability can be taken by changes in combing force. Hair thickness, porosity, and split ends may be measured with a scanning electron microscope and/or other microscopic imaging. Hair strength can be measured by tensile and flexabrasion testing. Photogoniometric measurements can be taken to assess hair shine. The hairs' amino acid and lipid composition can be measured with a number of common techniques known in the art such as chromatography. Measurements for its alkaline solubility may be determined by its solubility rate in the presence of a base. A subject's hairs' copper uptake may be assessed calorimetrically by measuring the remaining copper in a vial after incubating the subjects' hair in a copper-based solution. Discoloration measurements can be taken with various reflectometer devices using parameters such as the Commission International d'Eclairage (CIE) L*a*b* system. Said reflectometer devices may include the Photovolt ColorWalk (a tristimulus colorimeter) and/or the DermaSpectrometer (a narrow-band reflectometer). Other spectrometric and/or calorimetric devices may be employed. Subjects are then switched to Factor-4 (the supplement that contains the Power Amino Acid Complex) for the remainder of the evaluation period. At various points during the period when subjects are receiving Factor-4, subjects are measured again for combability, strength, thickness, porosity, split ends, hair shine, amino acid composition, lipid content, alkaline solubility, copper uptake, and discoloration. As described above, measurements for hair strength may be taken by tensile and flexabrasion testing. Hair thickness, porosity, and split ends may be measured with a scanning electron microscope and/or other microscopic imaging. The remaining parameters are measured using techniques such as reflectometry and chromatography as they have been described herein. Measurements for both regimens (Factor-4 and Factor-4(−)) may also include one or more surveys, questionnaires, interviews, or clinical or diagnostic techniques that are known in the art. The results from subjects who received supplementation with Factor-4(−) and Factor-4 can be compared. It will be found that the subjects' hair health and/or appearance who received the Power Amino Acid Complex-containing formulation (i.e., Factor-4) is improved compared to the subjects who did not receive the Power Amino Acid Complex (i.e., Factor-4(−)). One would expect to find improvements such as an increase in hair strength, an increase in hair thickness, a decrease in porosity, a reduction of split ends, an increase in shine, an increase of amino acids and lipids, a decrease in thiol content, a decrease in alkaline solubility, a decrease in copper uptake, and a reduction in color loss/fading. That is, in some embodiments, it is contemplated that hair health and/or appearance can be improved or restored completely by consumption of a dietary supplement, as described herein.

EXAMPLE 21

Oral Formulations Containing the Power Amino Acid Complex Improves Sperm Motility Sperm Count, Sperm Morphology Biochemical Characteristics of Semen, Sperm Penetration, and Sperm DNA Integrity Factor-4 (which includes the Power Amino Acid Complex) improves sperm motility, sperm count, and fertilization in men who were previously infertile. In one experiment, men who were approximately thirty-five (35) years old and infertile for more than five (5) years were tested for sperm motility, sperm count, and fertilization (in vitro) prior to consuming Factor-4. Subjects were given 20 g of Factor-4 twice to three times daily for two (2) months. At various time points during the supplementation period, measurements pertaining to sperm count, sperm motility, and fertilization capacity (in vitro) were made. Sperm count and motility were measured with a hemocytometer. Fertilization capacity of the subject was measured by successful in vitro fertilization using the subject's sperm and a woman's ova. Post in vitro fertilization, the embryos were transferred to the woman's womb and she became pregnant. The results from the post-supplementation measurements were compared with the pre-supplementation measurements. It was found that by providing a dietary supplement (i.e., Factor-4™) sperm count, sperm motility, and fertilization capacity were improved. That is, in some embodiments, it is contemplated that infertility as measured by the methods listed above can be lessened or eliminated completely by consumption of a dietary supplement, as described herein.

In other embodiments, the Power Amino Acid Complex comprises L-Lysine and/or L-Arginine and, in addition, at least one (1) amino acid selected from L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan). These amino acids are critical building blocks for enzymatic reactions in the body and are typically not provided at adequate levels in the diet. Supplementation of the Power Amino Acid Complex to the exclusion of others (consisting essentially of L-Lysine, L-Arginine, L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan)) can improve the health and well-being of a subject and provide the therapeutic benefits described herein. That is, it has been discovered that the Power Amino Acid Complex can be manufactured in many different formulations, and other amino acids or proteins are not required to receive a benefit.

One formulation of the Power Amino Acid Complex is oral. In particular, liquid formulations such as water (including variations of water such as Penta® Water) or various juices, with or without vitamins or other added supplements, may be used as the solvent with which the Power Amino Acid Complex is formulated. Other ingredients can comprise guar gum, lecithin, natural and artificial flavors, natural and artificial colors, fructo-oligosaccharide, and natural and artificial sweeteners. By providing the rate limiting amino acids, the Power Amino Acid Complex in water, for example, one can obtain the supplement and therapeutic benefits of the power amino acids while maintaining a low calorie intake.

In some embodiments a serving of the Power Amino Acid Complex can be less than, greater than, at least, or any number in between 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In one embodiment, a 2.2 g serving of the Power Amino Acid Complex contains amounts of each free-form power amino acid listed in Table 4.

Men can be identified as infertile by surveys, questionnaires, interviews, or clinical or diagnostic techniques that are known in the art. In some embodiments, a subject who is infertile can be identified according to his sperm motility, sperm count, sperm morphology, biochemical characteristics of semen, fertilization capacity, and sperm DNA integrity. Identification of men with low sperm count can be achieved manually with devices such as a hemocytometer. Computer-aided counting by computer-assisted semen analysis as well as other devices such as densitometers may also be employed. Identifying men with abnormal sperm motility can be performed manually by placing a diluted sample of semen on a wet mount and assessing visually under a microscope the percent of sperm that manifest motility. Likewise, sperm motility can be assessed with the use of a camera known as "track motility" estimation. First, a similarly prepared wet mount is placed under a microscope that is connected to a camera. Samples are then photographed using an exposure time conducive for sperm to produce "tracks" in the image. Motile sperm will produce movement artifacts (the track) while non-motile sperm will appear stationary. Sperm motility may also be assessed by computer-aided motility analysis. Identification of men with abnormal sperm morphology can be made by evaluating sperm size, shape, and appearance under a microscope. The use of dyes can be employed to help distinguish salient features of the sperms' morphology; and, other compounds such as hyaluronan can be used to evaluate sperm maturity. Identifying men with subnormal biochemical characteristics of their semen can be carried out by assessing its pH, color and turbidity, viscosity, agglutination, and liquefaction. Men with sperm that lacks in fertilization capacity may be identified in vitro by techniques such as the sperm penetration assay ("hamster test"). Finally, identifying men with abnormal sperm DNA integrity may be carried out using techniques such as the sperm DNA integrity assay and/or the sperm chromatin structure assay. Once a subject is identified as infertile by his semen and/or sperm characteristics, said subject will be given the Power Amino Acid Complex. In some embodiments, the Power Amino Acid Complex is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. During the period in which subjects are receiving the Power Amino Acid Complex, subjects are measured for sperm motility, sperm count, sperm morphology, biochemical characteristics of semen, fertilization capacity (in vitro), and sperm DNA integrity. Measurements may also include one or more surveys, questionnaires, interviews, or clinical or diagnostic techniques that are known in the art. As described above, measurements for sperm count can be achieved manually with a hemocytometer. Computer-aided counting by computer-assisted semen analysis as well as other devices such as densitometers may also be employed to measure the subjects' sperm count. Measuring sperm motility can be performed manually by placing a diluted sample of semen on a wet mount and assessing visually under a microscope the percent of sperm that manifests motility. Likewise, sperm motility can be measured by its "tracks." Sperm motility may also be measured by computer-aided motility analysis. Sperm morphology measurements can be taken by evaluating sperm size, shape, and appearance under a microscope. The use of dyes can be employed to help distinguish salient features of the sperms' morphology; and, other compounds such as hyaluronan can be used to evaluate sperm maturity. The biochemical properties of the subjects' semen can be measured by pH, color and turbidity, viscosity, agglutination, and liquefaction. Fertilization capacity can be measured in vitro by the hamster test. Measurements of sperm DNA integrity may be taken with the sperm DNA integrity assay and/or the sperm chromatin structure assay. The results from the post-supplementation measurements can be compared with the pre-supplementation measurements. It will be found that the infertile men who received the Power Amino Acid Complex have improvements in their semen and/or sperm compared to the subjects who did not receive the Power Amino Acid Complex. One would expect to find improvements such as increased sperm count and motility, better sperm morphology and biochemical characteristics of semen, and an increase in fertilization capacity and sperm DNA integrity. That is, in some embodiments, it is contemplated that infertility can be improved or restored completely by consumption of a dietary supplement, as described herein.

In another embodiment, the Power Amino Acid Complex may be formulated with the Factor-4 Protein Complex plus other non-essential amino acids and nutrients referred to as Factor-4. By formulating the Power Amino Acid Complex with the Factor-4 Protein Complex as well as other nutrients, vitamins, and non-essential amino acids, one can obtain the therapeutic benefits of the Power Amino Acid Complex that the Factor-4 Protein Complex, non-essential amino acids, vitamins, and other nutrients alone do not provide.

In one embodiment, a dietary supplement is composed of a powder which comprises the Factor-4 dietary supplement described in Tables 2 and 3. In another embodiment, a dietary supplement, Factor-4 minus the Power Amino Acid Complex ("Factor-4(−)"), is composed of a powder which is comprised of the elements described in Tables 2 and 5. In some embodiments, a serving of the dietary supplements can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In an embodiment, a 16.5 g serving of Factor-4 or Factor-4(−) will provide amounts of each element as described in Tables 2 and 3 and Tables 2 and 5, respectively.

Men can be identified as infertile by surveys, questionnaires, interviews, or clinical or diagnostic techniques that are known in the art. In some embodiments, a subject who is infertile can be identified according to his sperm motility, sperm count, sperm morphology, biochemical characteristics of semen, fertilization capacity, and sperm DNA integrity. Identification of men with low sperm count can be achieved manually with devices such as a hemocytometer. Computer-aided counting by computer-assisted semen analysis as well as other devices such as densitometers may also be employed. Identifying men with abnormal sperm motility can be performed manually by placing a diluted sample of semen on a wet mount and assessing visually under a microscope the percent of sperm that manifests motility. Likewise, sperm motility can be assessed with the use of a camera known as "track motility" estimation. First, a similarly prepared wet mount is placed under a microscope that is connected to a camera. Samples are then photographed using an exposure time conducive for sperm to produce "tracks" in the image. Motile sperm will produce movement artifacts (the track) while non-motile sperm will appear stationary. Sperm motility may also be assessed by computer-aided motility analysis. Identification of men with abnormal sperm morphology can be made by evaluating sperm size, shape, and appearance under a microscope. The use of dyes can be employed to help distinguish salient features of the sperms' morphology; and, other compounds such as hyaluronan can be used to evaluate sperm maturity. Identifying men with subnormal biochemical characteristics of their semen can be carried out by assessing its pH, color and turbidity, viscosity, agglutination, and liquefaction. Men with sperm that lacks in fertilization capacity may be identified in vitro by techniques such as the sperm penetration assay ("hamster test"). Finally, identifying men with abnormal sperm DNA integrity may be carried out using techniques such as the sperm DNA integrity assay and/or the sperm chromatin structure assay. Once a subject is identified as infertile by his semen and/or sperm characteristics, said subject will be given Factor-4 and Factor-4(−). In some embodiments, Factor-4(−) is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. During the period in which subjects are receiving Factor-4(−), subjects are measured for sperm motility, sperm count, sperm morphology, biochemical characteristics of semen, fertilization capacity (in vitro), and sperm DNA integrity. As described above, measurements for sperm count can be achieved manually with a hemocytometer. Computer-aided counting by computer-assisted semen analysis as well as other devices such as densitometers may also be employed to measure the subjects' sperm count. Measuring sperm motility can be performed manually by placing a diluted sample of semen on a wet mount and assessing visually under a microscope the percent of sperm that manifests motility. Likewise, sperm motility can be measured by its "tracks." Sperm motility may also be measured by computer-aided motility analysis. Sperm morphology measurements can be taken by evaluating sperm size, shape, and appearance under a microscope. The use of dyes can be employed to help distinguish salient features of the sperms' morphology; and, other compounds such as hyaluronan can be used to evaluate sperm maturity. The biochemical properties of the subjects' semen can be measured by pH, color and turbidity, viscosity, agglutination, and liquefaction. Fertilization capacity can be measured in vitro by using the hamster test. Measurements of sperm DNA integrity may be taken with the sperm DNA integrity assay and/or the sperm chromatin structure assay. Subjects are then switched to Factor-4 (the supplement that contains the Power Amino Acid Complex) for the remainder of the evaluation period. At various points during the period when subjects are receiving Factor-4, subjects are measured again for sperm motility, sperm count, sperm morphology, biochemical characteristics of semen, fertilization capacity (in vitro), and sperm DNA integrity. As described above, measurements for sperm count can be achieved manually with a hemocytometer, by computer-aided counting, and/or other devices such as densitometers. Sperm motility measurements can be taken manually by using a wet mount of the semen. Likewise, sperm motility can be measured by its "tracks" and/or by computer-aided motility analysis. Sperm morphology measurements can be taken regarding sperm size, shape, and appearance under a microscope. Biochemical properties of semen can be measured by pH, color and turbidity, viscosity, agglutination, and liquefaction. Fertilization capacity measurements can be taken using the hamster test. Sperm DNA integrity may be measured with the sperm DNA integrity assay and/or the sperm chromatin structure assay. Measurements for both regimens (Factor-4 and Factor-4(−)) may also include one or more surveys, questionnaires, interviews, or clinical or diagnostic techniques that are known in the art. The results from subjects who received supplementation with Factor-4(−) and Factor-4 can be compared. It will be found that infertile men who received the Power Amino Acid Complex-containing formulation (i.e., Factor-4) have improvements in their semen and/or sperm compared to the subjects who did not receive the Power Amino Acid Complex (i.e., Factor-4(−)). One would expect to find improvements such as increased sperm count and motility, better sperm morphology and biochemical characteristics of semen, and an increase in fertilization capacity and sperm DNA integrity. That is, in some embodiments, it is contemplated that infertility, can be improved or restored completely by consumption of a dietary supplement, as described herein.

EXAMPLE 22

Oral Formulations Containing The Power Amino Acid Complex Improves Mental and Neuromuscular Balance The Power Amino Acid Complex comprises L-Lysine and/or L-Arginine and, in addition, at least one (1) amino acid selected from L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan). These amino acids are critical building blocks for enzymatic reactions in the body and are typically not provided at adequate levels in the diet. Supplementation of the Power Amino Acid Complex to the exclusion of others (consisting essentially of L-Lysine, L-Arginine, L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan)) can improve the health and well-being of a subject and provide the therapeutic benefits described herein. That is, it has been discovered that the Power Amino Acid Complex can be manufactured in many different formulations, and other amino acids or proteins are not required to receive a benefit.

One formulation of the Power Amino Acid Complex is oral. In particular, liquid formulations such as water (including variations of water such as Penta® Water) or various juices, with or without vitamins or other added supplements, may be used as the solvent with which the Power Amino Acid Complex is formulated. Other ingredients can comprise guar gum, lecithin, natural and artificial flavors, natural and artificial colors, fructo-oligosaccharide, and natural and artificial sweeteners. By providing the rate limiting amino acids, the Power Amino Acid Complex in water, for example, one can obtain the supplement and therapeutic benefits of the power amino acids while maintaining a low calorie intake.

In some embodiments a serving of the Power Amino Acid Complex can be less than, greater than, at least, or any number in between 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In one embodiment, a 2.2 g serving of the Power Amino Acid Complex contains amounts of each free-form power amino acid listed in Table 4.

A subject can be identified as one who is lacking in mental and neuromuscular balance by survey, questionnaire, interview, psychiatric evaluation, reflex evaluation, or by clinical or diagnostic techniques known in the art. Once a subject is identified as lacking in mental and neuromuscular balance, said subject can be provided a dietary supplement, as described herein. In some embodiments, the Power Amino Acid Complex is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of the subject can be performed. As explained above, such analysis may include a survey, questionnaire, interview, psychiatric evaluation, reflex evaluation, or clinical or diagnostic techniques known in the art. The results from the post-supplementation measurements can be compared with the pre-supplementation measurements. It will be found that by providing a dietary supplement as described herein, the subject's mental and neuromuscular balance who received the Power Amino Acid Complex is improved compared to the subjects who did not receive the Power Amino Acid Complex. One would expect to find improvements such as a stabilization of mood swings, a decrease in depression, a decrease in body stress, a more restful sleep, an increase of muscle relaxation and an improved memory capacity. That is, in some embodiments, it is contemplated that mental and neuromuscular balance, defined by survey, questionnaire, interview, psychiatric evaluation, reflex evaluation, or clinical or diagnostic techniques known in the art can be improved by consumption of the dietary supplement, as described herein.

In another embodiment, the Power Amino Acid Complex may be formulated with the Factor-4 Protein Complex plus other non-essential amino acids and nutrients referred to as Factor-4. By formulating the Power Amino Acid Complex with the Factor-4 Protein Complex as well as other nutrients, vitamins, and non-essential amino acids, one can obtain the therapeutic benefits of the Power Amino Acid Complex that the Factor-4 Protein Complex, non-essential amino acids, vitamins, and other nutrients alone do not provide.

In one embodiment, a dietary supplement is composed of a powder which comprises the Factor-4 dietary supplement described in Tables 2 and 3. In another embodiment, a dietary supplement, Factor-4 minus the Power Amino Acid Complex ("Factor-4(−)"), is composed of a powder which is comprised of the elements described in Tables 2 and 5. In some embodiments, a serving of the dietary supplements can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In an embodiment, a 16.5 g serving of Factor-4 or Factor-4(−) will provide amounts of each element as described in Tables 2 and 3 and Tables 2 and 5, respectively.

A subject can be identified as one who is lacking in mental and neuromuscular balance by survey, questionnaire, interview, psychiatric evaluation, reflex evaluation, or by clinical or diagnostic techniques known in the art. Once a subject is identified as lacking in mental and neuromuscular balance, said subject will be given Factor-4 and Factor-4(−). In some embodiments, Factor-4(−) is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period in which subjects are receiving Factor-4(−), an analysis of the subject can be performed. As explained above, such analysis may include a survey, questionnaire, interview, psychiatric evaluation, reflex evaluation, or clinical or diagnostic techniques known in the art. Subjects are then switched to Factor-4 (the supplement that contains the Power Amino Acid Complex) for the remainder of the evaluation period. At various points during the period when subjects are receiving Factor-4, subjects are measured again. As described above, this may include a survey, questionnaire, interview, psychiatric evaluation, reflex evaluation, or clinical or diagnostic techniques known in the art. The results from subjects who received supplementation with Factor-4(−) and Factor-4 can be compared. It will be found that the subjects' mental and neuromuscular balance who received the Power Amino Acid Complex-containing formulation (i.e., Factor-4) is improved compared to the subjects who did not receive the Power Amino Acid Complex (i.e., Factor-4(−)). One would expect to find improvements such as a stabilization of mood swings, a decrease in depression, a decrease in body stress, a more restful sleep, an increase of muscle relaxation and an improved memory capacity. That is, in some embodiments, it is contemplated that mental and neuromuscular balance, defined by survey, questionnaire, interview, psychiatric evaluation, reflex evaluation, or clinical or diagnostic techniques known in the art can be improved by consumption of the dietary supplement, as described herein.

EXAMPLE 23

Oral Formulations Containing the Power Amino Acid Complex Improves Poor Diet

The Power Amino Acid Complex comprises L-Lysine and/or L-Arginine and, in addition, at least one (1) amino acid selected from L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan). These amino acids are critical building blocks for enzymatic reactions in the body and are typically not provided at adequate levels in the diet. Supplementation of the Power Amino Acid Complex to the exclusion of others (consisting essentially of L-Lysine, L-Arginine, L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan)) can improve the health and well-being of a subject and provide the therapeutic benefits described herein. That is, it has been discovered that the Power Amino Acid Complex can be manufactured in many different formulations, and other amino acids or proteins are not required to receive a benefit.

One formulation of the Power Amino Acid Complex is oral. In particular, liquid formulations such as water (including variations of water such as Penta® Water) or various juices, with or without vitamins or other added supplements, may be used as the solvent with which the Power Amino Acid Complex is formulated. Other ingredients can comprise guar gum, lecithin, natural and artificial flavors, natural and artificial colors, fructo-oligosaccharide, and natural and artificial sweeteners. By providing the rate limiting amino acids, the Power Amino Acid Complex in water, for example, one can obtain the supplement and therapeutic benefits of the power amino acids while maintaining a low calorie intake.

In some embodiments a serving of the Power Amino Acid Complex can be less than, greater than, at least, or any number in between 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In one embodiment, a 2.2 g serving of the Power Amino Acid Complex contains amounts of each free-form power amino acid listed in Table 4.

A subject can be identified as one having poor dietary habits by survey, questionnaire, interview, observation, or clinical or diagnostic techniques that are known in the art. In some embodiments, the existence of a poor diet in a subject is identified by employing a proteomic analysis of a sample obtained from said subject as described above in Example 7. Once a subject is identified as having poor dietary habits, said subject will be given the Power Amino Acid Complex. In some embodiments, the Power Amino Acid Complex is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, a dietary analysis can be conducted. Measurements may include one or more surveys, questionnaires, interviews, or clinical or diagnostic techniques that are known in the art. The results from the post-supplementation measurements can be compared with the pre-supplementation measurements. It will be found that a subject's poor dietary habits who received the Power Amino Acid Complex are improved compared to the subjects who did not receive the Power Amino Acid Complex. One would expect to find improvements such as a shift in desire from low-value foods to high-value foods, a shift in desire away from fast foods, snacks and desserts, a shift in desire away from processed foods containing excess fat, salt and sugar, a decrease in eating frequency and an improvement in portion control. That is, in some embodiments, it is contemplated that poor dietary habits can be improved by consumption of a dietary supplement, as described herein.

In another embodiment, the Power Amino Acid Complex may be formulated with the Factor-4 Protein Complex plus other non-essential amino acids and nutrients referred to as Factor-4. By formulating the Power Amino Acid Complex with the Factor-4 Protein Complex as well as other nutrients, vitamins, and non-essential amino acids, one can obtain the therapeutic benefits of the Power Amino Acid Complex that the Factor-4 Protein Complex, non-essential amino acids, vitamins, and other nutrients alone do not provide.

In one embodiment, a dietary supplement is composed of a powder which comprises the Factor-4 dietary supplement described in Tables 2 and 3. In another embodiment, a dietary supplement, Factor-4 minus the Power Amino Acid Complex ("Factor-4(−)"), is composed of a powder which is comprised of the elements described in Tables 2 and 5. In some embodiments, a serving of the dietary supplements can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In an embodiment, a 16.5 g serving of Factor-4 or Factor-4(−) will provide amounts of each element as described in Tables 2 and 3 and Tables 2 and 5, respectively.

A subject can be identified as one having poor dietary habits by survey, questionnaire, interview, observation, or clinical or diagnostic techniques that are known in the art. In some embodiments, the existence of a poor diet in a subject is identified by employing a proteomic analysis of a sample obtained from said subject as described above in Example 7. Once a subject is identified as having poor dietary habits, said subject will be given Factor-4 and Factor-4(−). In some embodiments, Factor-4(−) is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, a dietary analysis can be conducted. Measurements may include one or more surveys, questionnaires, interviews, or clinical or diagnostic techniques that are known in the art. Subjects are then switched to Factor-4 (the supplement that contains the Power Amino Acid Complex) for the remainder of the evaluation period. At various points during the period when subjects are receiving Factor-4, their diets are again analyzed. As described above, measurements can be taken by one or more surveys, questionnaires, interviews, or clinical or diagnostic techniques that are known in the art. The results from subjects who received supplementation with Factor-4(−) and Factor-4™ can be compared. It will be found that a subject's poor dietary habits who received the Power Amino Acid Complex-containing formulation (i.e., Factor-4) is improved compared to the subjects who did not receive the Power Amino Acid Complex (i.e., Factor-4(−)). One would expect to find improvements such as a shift in desire from low-value foods to high-value foods, a shift in desire away from fast foods, snacks and desserts, a shift in desire away from processed foods containing excess fat, salt and sugar, a decrease in eating frequency and an improvement in portion control. That is, in some embodiments, it is contemplated that poor dietary habits can be improved by consumption of a dietary supplement, as described herein.

EXAMPLE 24

Oral Formulations Containing the Power Amino Acid Complex Improves Digestive Health The Power Amino Acid Complex comprises L-Lysine and/or L-Arginine and, in addition, at least one (1) amino acid selected from L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan). These amino acids are critical building blocks for enzymatic reactions in the body and are typically not provided at adequate levels in the diet. Supplementation of the Power Amino Acid Complex to the exclusion of others (consisting essentially of L-Lysine, L-Arginine, L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan)) can improve the health and well-being of a subject and provide the therapeutic benefits described herein. That is, it has been discovered that the Power Amino Acid Complex can be manufactured in many different formulations, and other amino acids or proteins are not required to receive a benefit.

One formulation of the Power Amino Acid Complex is oral. In particular, liquid formulations such as water (including variations of water such as Penta® Water) or various juices, with or without vitamins or other added supplements, may be used as the solvent with which the Power Amino Acid Complex is formulated. Other ingredients can comprise guar gum, lecithin, natural and artificial flavors, natural and artificial colors, fructo-oligosaccharide, and natural and artificial sweeteners. By providing the rate limiting amino acids, the Power Amino Acid Complex in water, for example, one can obtain the supplement and therapeutic benefits of the power amino acids while maintaining a low calorie intake.

In some embodiments a serving of the Power Amino Acid Complex can be less than, greater than, at least, or any number in between 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In one embodiment, a 2.2 g serving of the Power Amino Acid Complex contains amounts of each free-form power amino acid listed in Table 4.

A subject can be identified as one having a digestive heath problem by surveys, questionnaires, medical evaluations, or clinical or diagnostic techniques that are known in the art. Once a subject is identified as having a digestive heath problem, said subject will be given the Power Amino Acid Complex. In some embodiments, the Power Amino Acid Complex is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of digestive health can be made. As described above, the analysis can include surveys, questionnaires, medical evaluations, or clinical or diagnostic techniques that are known in the art. The results from the post-supplementation measurements can be compared with the pre-supplementation measurements. It will be found that the subjects' digestive health who received the Power Amino Acid Complex is improved compared to the subjects who did not receive the Power Amino Acid Complex. One would expect to find improvements such as a taste adaptation toward high-value foods, an inhibiting of taste adaptation toward low-value foods, including snacks, processed foods and fast foods, an increase in pleasure and taste to the pallets in the oral and pharyngeal cavities, including tongue and throat, respectively, an increase in appetite satisfaction, a reduction in acid reflux and upset stomach, a reduction in stomach bloating, decrease in symptoms of hiatus hernia including heartburn and indigestion, and an increase in bowel movement regularity. That is, in some embodiments, it is contemplated that digestive health problems as measured by surveys, questionnaires, medical evaluations or clinical or diagnostic techniques that are known in the art can be ameliorated or eliminated completely by consumption of a dietary supplement, as described herein.

In another embodiment, the Power Amino Acid Complex may be formulated with the Factor-4 Protein Complex plus other non-essential amino acids and nutrients referred to as Factor-4™. By formulating the Power Amino Acid Complex with the Factor-4 Protein Complex as well as other nutrients, vitamins, and non-essential amino acids, one can obtain the therapeutic benefits of the Power Amino Acid Complex that the Factor-4 Protein Complex, non-essential amino acids, vitamins, and other nutrients alone do not provide.

In another embodiment, the Power Amino Acid Complex may be formulated with the Factor-4 Protein Complex plus other non-essential amino acids and nutrients referred to as Factor-4. By formulating the Power Amino Acid Complex with the Factor-4 Protein Complex as well as other nutrients, vitamins, and non-essential amino acids, one can obtain the therapeutic benefits of the Power Amino Acid Complex that the Factor-4 Protein Complex, non-essential amino acids, vitamins, and other nutrients alone do not provide.

In one embodiment, a dietary supplement is composed of a powder which comprises the Factor-4 dietary supplement described in Tables 2 and 3. In another embodiment, a dietary supplement, Factor-4 minus the Power Amino Acid Complex ("Factor-4(−)"), is composed of a powder which is comprised of the elements described in Tables 2 and 5. In some embodiments, a serving of the dietary supplements can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In an embodiment, a 16.5 g serving of Factor-4 or Factor-4(−) will provide amounts of each element as described in Tables 2 and 3 and Tables 2 and 5, respectively.

EXAMPLE 25

Oral Formulations Containing the Power Amino Acid Complex Improves Immune Health A subject can be identified as one having a digestive heath problem by surveys, questionnaires, medical evaluations, or clinical or diagnostic techniques that are known in the art. Once a subject is identified as having a digestive heath problem, said subject will be given Factor-4 and Factor-4(−). In some embodiments, Factor-4(−) is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the period in which subjects are receiving Factor-4(−), an analysis of digestive health can be made. Subjects are then switched to Factor-4 (the supplement that contains the Power Amino Acid Complex) for the remainder of the evaluation period. At various points during the period when subjects are receiving Factor-4, subjects are measured again for digestive health. As described above, measurements can be taken through one or more surveys, questionnaires, interviews, or clinical or diagnostic techniques that are known in the art. The results from subjects who received supplementation with Factor-4(−) and Factor-4 can be compared. It will be found that the subjects' digestive health who received the Power Amino Acid Complex-containing formulation (i.e., Factor-4) is improved compared to the subjects who did not receive the Power Amino Acid Complex (i.e., Factor-4(−)). One would expect to find improvements such as a taste adaptation toward high-value foods, an inhibiting of taste adaptation toward low-value foods, including snacks, processed foods and fast foods, an increase in pleasure and taste to the pallets in the oral and pharyngeal cavities, including tongue and throat, respectively, an increase in appetite satisfaction, a reduction in acid reflux and upset stomach, a reduction in stomach bloating, decrease in symptoms of hiatus hernia including heartburn and indigestion, and an increase in bowel movement regularity. That is, in some embodiments, it is contemplated that digestive health problems as measured by surveys, questionnaires, medical evaluations, or clinical or diagnostic techniques that are known in the art can be ameliorated or eliminated completely by consumption of a dietary supplement, as described herein.

One formulation of the Power Amino Acid Complex is oral. In particular, liquid formulations such as water (including variations of water such as Penta® Water) or various juices, with or without vitamins or other added supplements, may be used as the solvent with which the Power Amino Acid Complex is formulated. Other ingredients can comprise guar gum, lecithin, natural and artificial flavors, natural and artificial colors, fructo-oligosaccharide, and natural and artificial sweeteners. By providing the rate limiting amino acids, the Power Amino Acid Complex in water, for example, one can obtain the supplement and therapeutic benefits of the power amino acids while maintaining a low calorie intake.

In some embodiments a serving of the Power Amino Acid Complex can be less than, greater than, at least, or any number in between 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In one embodiment, a 2.2 g serving of the Power Amino Acid Complex contains amounts of each free-form power amino acid listed in Table 4.

A subject can be identified as one having an immunocompetency by survey, questionnaire, interview, or clinical or diagnostic techniques that are known in the art. Once a subject is identified as having an immunodeficiency, said subject will be given the Power Amino Acid Complex. In some embodiments, the Power Amino Acid Complex is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of the immunocompetency can be made. As described above, the analysis can include surveys, questionnaires, medical evaluations, or clinical or diagnostic techniques that are known in the art. The results from the post-supplementation measurements can be compared with the pre-supplementation measurements. It will be found that the subjects' immunocompetency who received the Power Amino Acid Complex is improved compared to the subjects who did not receive the Power Amino Acid Complex. One would expect to find improvements such as a strengthening of the immune system, an increase in natural resistance to viruses (e.g., Rhinovirus, Influenza, and Herpes Simplex Virus), an increase in natural resistance to fungi (e.g., the genera *Epidermophyton, Trichophyton*, and Microsporum that infect skin, hair, and nails), a suppression of yeast infections (e.g., particularly, but not limited to, yeast infections that occur in the ears of dogs and other pets), and an increase in natural resistance to bacteria. That is, in some embodiments, it is contemplated that the immune system as measured by the presence and/or amounts of essential and semi-essential amino acids, in particular Lysine, Arginine, and/or Histidine, can be improved or restored completely by consumption of a dietary supplement, as described herein.

In another embodiment, the Power Amino Acid Complex may be formulated with the Factor-4 Protein Complex plus other non-essential amino acids and nutrients referred to as Factor-4. By formulating the Power Amino Acid Complex with the Factor-4 Protein Complex as well as other nutrients, vitamins, and non-essential amino acids, one can obtain the therapeutic benefits of the Power Amino Acid Complex that the Factor-4 Protein Complex, non-essential amino acids, vitamins, and other nutrients alone do not provide.

In one embodiment, a dietary supplement is composed of a powder which comprises the Factor-4 dietary supplement described in Tables 2 and 3. In another embodiment, a dietary supplement, Factor-4 minus the Power Amino Acid Complex ("Factor-4(−)"), is composed of a powder which is comprised of the elements described in Tables 2 and 5. In some embodiments, a serving of the dietary supplements can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In an embodiment, a 16.5 g serving of Factor-4 or Factor-4(−) will provide amounts of each element as described in Tables 2 and 3 and Tables 2 and 5, respectively.

A subject can be identified as one having an immunocompetency by survey, questionnaire, interview, or clinical or diagnostic techniques that are known in the art. Once a subject is identified as having an immunodeficiency, said subject will be given Factor-4 and Factor-4(−). In some embodiments, Factor-4(−) is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the period in which subjects are receiving Factor-4(−), an analysis of immunocompetency can be made. Subjects are then switched to Factor-4 (the supplement that contains the Power Amino Acid Complex) for the remainder of the evaluation period. At various points during the period when subjects are receiving Factor-4, subjects are measured again for immune health. Measurements for both regimens (Factor-4™ and Factor-4(−)) may include one or more surveys, questionnaires, interviews, or clinical or diagnostic techniques that are known in the art. The results from subjects who received supplementation with Factor-4(−) and Factor-4™ can be compared. It will be found that the subjects' immunocompetency who received the Power Amino Acid Complex-containing formulation (i.e., Factor-4) is improved compared to the subjects who did not receive the Power Amino Acid Complex (i.e., Factor-4(−)). One would expect to find improvements such as a strengthening of the immune system, an increase in natural resistance to viruses (e.g., Rhinovirus, Influenza, and Herpes Simplex Virus), an increase in natural resistance to fungi (e.g., the genera Epidermophyton, Trichophyton, and Microsporum that infect skin, hair, and nails), a suppression of yeast infections (e.g., particularly, but not limited to, yeast infections that occur in the ears of dogs and other pets), and an increase in natural resistance to bacteria. That is, in some embodiments, it is contemplated that the immune system as measured by the presence and/or amounts of essential and semi-essential amino acids, in particular Lysine, Arginine, and/or Histidine, can be improved or restored completely by consumption of a dietary supplement, as described herein.

EXAMPLE 26

Oral Formulations Containing the Power Amino Acid Complex Improves Medical Health The Power Amino Acid Complex comprises L-Lysine and/or L-Arginine and, in addition, at least one (1) amino acid selected from L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan). These amino acids are critical building blocks for enzymatic reactions in the body and are typically not provided at adequate levels in the diet. Supplementation of the Power Amino Acid Complex to the exclusion of others (consisting essentially of L-Lysine, L-Arginine, L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan)) can improve the health and well-being of a subject and provide the therapeutic benefits described herein. That is, it has been discovered that the Power Amino Acid Complex can be manufactured in many different formulations, and other amino acids or proteins are not required to receive a benefit.

One formulation of the Power Amino Acid Complex is oral. In particular, liquid formulations such as water (including variations of water such as Penta® Water) or various juices, with or without vitamins or other added supplements, may be used as the solvent with which the Power Amino Acid Complex is formulated. Other ingredients can comprise guar gum, lecithin, natural and artificial flavors, natural and artificial colors, fructo-oligosaccharide, and natural and artificial sweeteners. By providing the rate limiting amino acids, the Power Amino Acid Complex in water, for example, one can obtain the supplement and therapeutic benefits of the power amino acids while maintaining a low calorie intake.

In some embodiments a serving of the Power Amino Acid Complex can be less than, greater than, at least, or any number in between 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In one embodiment, a 2.2 g serving of the Power Amino Acid Complex contains amounts of each free-form power amino acid listed in Table 4.

A subject can be identified as one having one or more medical health concerns due to, for example, Type II Diabetes, blood sugar levels (e.g., determined by fasting blood sugar and glucose tolerance tests), high blood pressure (systolic and diastolic blood pressure), total cholesterol, LDL cholesterol, HDL cholesterol, triglycerides, body inflammation (e.g., assays for C-reactive proteins and cytokine levels), blood coagulation factors (e.g., factor VIII and IX), or arthritis pain. Such medical health concerns may be identified by survey, questionnaire, interview, or clinical or diagnostic techniques that are known in the art. Once a subject is identified as having a medical health concern, said subject will be given the Power Amino Acid Complex. In some embodiments, the Power Amino Acid Complex is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of the one or more medial health concerns can be made. As described above, the analysis can include survey, questionnaire, interview, or clinical or diagnostic techniques that are known in the art. The results from the post-supplementation measurements can be compared with the pre-supplementation measurements. It will be found that a subject's medical health who received the Power Amino Acid Complex is improved compared to the subjects who did not receive the Power Amino Acid Complex. One would expect to find improvements such as a decrease in Type II Diabetes symptoms, a decrease in systolic and diastolic blood pressure, a decrease in total cholesterol and in LDL cholesterol, a decrease in C-reactive protein, a non-specific indicator of inflammation, triglycerides, and a decrease in arthritic pain including pain due to osteoarthritis and tendonitis. That is, in some embodiments, it is contemplated that medical health as measured by the above mentioned techniques can be improved or restored completely by consumption of a dietary supplement, as described herein.

In another embodiment, the Power Amino Acid Complex may be formulated with the Factor-4 Protein Complex plus other non-essential amino acids and nutrients referred to as Factor-4. By formulating the Power Amino Acid Complex with the Factor-4 Protein Complex as well as other nutrients, vitamins, and non-essential amino acids, one can obtain the therapeutic benefits of the Power Amino Acid Complex that the Factor-4 Protein Complex, non-essential amino acids, vitamins, and other nutrients alone do not provide.

In one embodiment, a dietary supplement is composed of a powder which comprises the Factor-4 dietary supplement described in Tables 2 and 3. In another embodiment, a dietary supplement, Factor-4 minus the Power Amino Acid Complex ("Factor-4(−)"), is composed of a powder which is comprised of the elements described in Tables 2 and 5. In some embodiments, a serving of the dietary supplements can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In an embodiment, a 16.5 g serving of Factor-4 or Factor-4(−) will provide amounts of each element as described in Tables 2 and 3 and Tables 2 and 5, respectively.

A subject can be identified as one having one or more medical health concerns due to, for example, Type II Diabetes, blood sugar levels (e.g., determined by fasting blood sugar and glucose tolerance tests), high blood pressure (systolic and diastolic blood pressures), total cholesterol, LDL cholesterol, HDL cholesterol, triglycerides, body inflammation (e.g., assays for C-reactive proteins and cytokine levels), blood coagulation factors (e.g., factor VIII and IX), or arthritis pain. Such medical health concerns may be identified by survey, questionnaire, interview, or clinical or diagnostic techniques that are known in the art. Once a subject is identified as having a medical health concern, said subject will be given Factor-4 and Factor-4(−). In some embodiments, Factor-4(−) is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the period in which subjects are receiving Factor-4(−), an analysis of the one or more medial health concerns can be made. Subjects are then switched to Factor-4 (the supplement that contains the Power Amino Acid Complex) for the remainder of the evaluation period. At various points during the period when subjects are receiving Factor-4, subjects are measured again for medical health. Measurements for both regimens (Factor-4 and Factor-4(−)) may also include one or more surveys, questionnaires, interviews, or clinical or diagnostic techniques that are known in the art. The results from subjects who received supplementation with Factor-4(−) and Factor-4 can be compared. It will be found that a subject's medical health who received the Power Amino Acid Complex-containing formulation (i.e., Factor-4) is improved compared to the subjects who did not receive the Power Amino Acid Complex (i.e., Factor-4(−)). One would expect to find improvements such as a decrease in Type II Diabetes symptoms, a decrease in systolic and diastolic blood pressure, a decrease in total cholesterol and in LDL cholesterol, a decrease in C-reactive protein, a non-specific indicator of inflammation, triglycerides, and a decrease in arthritic pain including pain due to osteoarthritis and tendonitis. That is, in some embodiments, it is contemplated that medical health as measured by the above mentioned techniques can be improved or restored completely by consumption of a dietary supplement, as described herein.

EXAMPLE 27

Oral Formulations Containing the Power Amino Acid Complex Improves Age-Related Health The Power Amino Acid Complex comprises L-Lysine and/or L-Arginine and, in addition, at least one (1) amino acid selected from L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan). These amino acids are critical building blocks for enzymatic reactions in the body and are typically not provided at adequate levels in the diet. Supplementation of the Power Amino Acid Complex to the exclusion of others (consisting essentially of L-Lysine, L-Arginine, L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan)) can improve the health and well-being of a subject and provide the therapeutic benefits described herein. That is, it has been discovered that the Power Amino Acid Complex can be manufactured in many different formulations, and other amino acids or proteins are not required to receive a benefit.

One formulation of the Power Amino Acid Complex is oral. In particular, liquid formulations such as water (including variations of water such as Penta® Water) or various juices, with or without vitamins or other added supplements, may be used as the solvent with which the Power Amino Acid Complex is formulated. Other ingredients can comprise guar gum, lecithin, natural and artificial flavors, natural and artificial colors, fructo-oligosaccharide, and natural and artificial sweeteners. By providing the rate limiting amino acids, the Power Amino Acid Complex in water, for example, one can obtain the supplement and therapeutic benefits of the power amino acids while maintaining a low calorie intake.

In some embodiments a serving of the Power Amino Acid Complex can be less than, greater than, at least, or any number in between 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In one embodiment, a 2.2 g serving of the Power Amino Acid Complex contains amounts of each free-form power amino acid listed in Table 4.

A subject can be identified as one having poor health due to aging by surveys, questionnaires, interviews, or clinical or diagnostic techniques that are known in the art. In some embodiments, subjects can be identified by, for example, energy levels (e.g., activity, stamina, endurance, and natural desire for exercise), posture, body fitness, cognitive tests that monitor cerebral function, extra-pyramidal tests that monitor body coordination and balance, strength and muscle tone, sensory functions (e.g., sight, hearing, taste, smell, and touch), and factors associated with the Metabolic Syndrome. Once a subject is identified as having age-related health concerns, said subject will be given the Power Amino Acid Complex. In some embodiments, the Power Amino Acid Complex is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of the age-related health concerns can be made. As described above, the analysis can include one or more surveys, questionnaires, interviews, or clinical or diagnostic techniques that are known in the art. The results from the post-supplementation measurements can be compared with the pre-supplementation measurements. It will be found that the subjects' poor health due to age who received the Power Amino Acid Complex is improved compared to the subjects who did not receive the Power Amino Acid Complex. One would expect to find improvements such as an absence of tired, weak and sluggish feelings, a decrease in functional age, an increase in aging performance, improvements in posture, improvements in body fitness, improvements in cerebral function, improvements in coordination and balance, improvements in muscle tone and strength, increases in sensory functions, improvements in risk factors that are associated with the Metabolic Syndrome, and a prevention of age-related diseases (thus indicating an increase in longevity that turns back the hands of time and promotes youth). That is, in some embodiments, it is contemplated that poor health due to age can be improved or restored completely by consumption of a dietary supplement, as described herein.

In another embodiment, the Power Amino Acid Complex may be formulated with the Factor-4 Protein Complex plus other non-essential amino acids and nutrients referred to as Factor-4. By formulating the Power Amino Acid Complex with the Factor-4 Protein Complex as well as other nutrients, vitamins, and non-essential amino acids, one can obtain the therapeutic benefits of the Power Amino Acid Complex that the Factor-4 Protein Complex, non-essential amino acids, vitamins, and other nutrients alone do not provide.

In one embodiment, a dietary supplement is composed of a powder which comprises the Factor-4 dietary supplement described in Tables 2 and 3. In another embodiment, a dietary supplement, Factor-4 minus the Power Amino Acid Complex ("Factor-4(−)"), is composed of a powder which is comprised of the elements described in Tables 2 and 5. In some embodiments, a serving of the dietary supplements can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In an embodiment, a 16.5 g serving of Factor-4 or Factor-4(−) will provide amounts of each element as described in Tables 2 and 3 and Tables 2 and 5, respectively.

A subject can be identified as one having poor health due to aging by surveys, questionnaires, interviews, or clinical or diagnostic techniques that are known in the art. In some embodiments, subjects can be identified by, for example, energy levels (e.g., activity, stamina, endurance, and natural desire for exercise), posture, body fitness, cognitive tests that monitor cerebral function, extra-pyramidal tests that monitor body coordination and balance, strength and muscle tone, sensory functions (e.g., sight, hearing, taste, smell, and touch), and factors associated with the Metabolic Syndrome. Once a subject is identified as having age-related health concerns, said subject will be given Factor-4 and Factor-4(−). In some embodiments, Factor-4(−) is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the period in which subjects are receiving Factor-4(−), measurements for age-related health concerns are taken. Subjects are then switched to Factor-4 (the supplement that contains the Power Amino Acid Complex) for the remainder of the evaluation period. At various points during the period when subjects are receiving Factor-4, subjects are measured again. Measurements for both regimens (Factor-4 and Factor-4(−)) may include one or more surveys, questionnaires, interviews, or clinical or diagnostic techniques that are known in the art. The results from subjects who received supplementation with Factor-4(−) and Factor-4 can be compared. It will be found that the subjects' poor health due to age who received the Power Amino Acid Complex-containing formulation (i.e., Factor-4) is improved compared to the subjects who did not receive the Power Amino Acid Complex (i.e., Factor-4(−)). One would expect to find improvements such as an absence of tired, weak and sluggish feelings, a decrease in functional age, an increase in aging performance, improvements in posture, improvements in body fitness, improvements in cerebral function, improvements in coordination and balance, improvements in muscle tone and strength, increases in sensory functions, improvements in risk factors that are associated with the Metabolic Syndrome, and a prevention of age-related diseases (thus indicating an increase in longevity that turns back the hands of time and promotes youth). That is, in some embodiments, it is contemplated that poor health due to age can be improved or restored completely by consumption of a dietary supplement, as described herein.

EXAMPLE 28

Oral Formulations Containing the Power Amino Acid Complex Improves Addiction Health The Power Amino Acid Complex comprises L-Lysine and/or L-Arginine and, in addition, at least one (1) amino acid selected from L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan). These amino acids are critical building blocks for enzymatic reactions in the body and are typically not provided at adequate levels in the diet. Supplementation of the Power Amino Acid Complex to the exclusion of others (consisting essentially of L-Lysine, L-Arginine, L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan)) can improve the health and well-being of a subject and provide the therapeutic benefits described herein. That is, it has been discovered that the Power Amino Acid Complex can be manufactured in many different formulations, and other amino acids or proteins are not required to receive a benefit.

One formulation of the Power Amino Acid Complex is oral. In particular, liquid formulations such as water (including variations of water such as PENTA® Water (trademark of Bio-Hydration Research Lab, Inc., San Diego, Calif.) or various juices, with or without vitamins or other added supplements, may be used as the solvent with which the Power Amino Acid Complex is formulated. Other ingredients can comprise guar gum, lecithin, natural and artificial flavors, natural and artificial colors, fructo-oligosaccharide, and natural and artificial sweeteners. By providing the rate limiting amino acids, the Power Amino Acid Complex in water, for example, one can obtain the supplement and therapeutic benefits of the power amino acids while maintaining a low calorie intake.

In some embodiments a serving of the Power Amino Acid Complex can be less than, greater than, at least, or any number in between 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In one embodiment, a 2.2 g serving of the Power Amino Acid Complex contains amounts of each free-form power amino acid listed in Table 4.

A subject can be identified as one having one or more dependencies or addictions by surveys, questionnaires, interviews, or clinical or diagnostic techniques that are known in the art. Once a subject is identified as having an addiction, said subject will be given the Power Amino Acid Complex. In some embodiments, the Power Amino Acid Complex is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of the addiction can be made. Measurements may include one or more surveys, questionnaires, interviews, or clinical or diagnostic techniques that are known in the art. The results from the post-supplementation measurements can be compared with the pre-supplementation measurements. It will be found that a subject's addiction who received the Power Amino Acid Complex can be lessened and/or eliminated compared to subjects who did not receive the Power Amino Acid Complex. One would expect to find improvements such as decreases in food addictions, decreases in sugar, fat, and salt addictions, decreases in caffeine addictions, decreases in smoking addictions, and decreases in drug and alcohol addictions. Additionally, subjects reported an acceleration of recovery from alcohol toxicity (hangovers). That is, in some embodiments, it is contemplated that addictions as measured by the methods listed above can be lessened or eliminated completely by consumption of a dietary supplement, as described herein.

In another embodiment, the Power Amino Acid Complex may be formulated with the Factor-4 Protein Complex plus other non-essential amino acids and nutrients referred to as Factor-4. By formulating the Power Amino Acid Complex with the Factor-4 Protein Complex as well as other nutrients, vitamins, and non-essential amino acids, one can obtain the therapeutic benefits of the Power Amino Acid Complex that the Factor-4 Protein Complex, non-essential amino acids, vitamins, and other nutrients alone do not provide.

In one embodiment, a dietary supplement is composed of a powder which comprises the Factor-4 dietary supplement described in Tables 2 and 3. In another embodiment, a dietary supplement, Factor-4 minus the Power Amino Acid Complex ("Factor-4(−)"), is composed of a powder which is comprised of the elements described in Tables 2 and 5. In some embodiments, a serving of the dietary supplements can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In an embodiment, a 16.5 g serving of Factor-4 or Factor-4(−) will provide amounts of each element as described in Tables 2 and 3 and Tables 2 and 5, respectively.

A subject can be identified as one having one or more dependencies or addictions by surveys, questionnaires, interviews, or clinical or diagnostic techniques that are known in the art. Once a subject is identified as having an addiction, said subject will be given Factor-4 and Factor-4(−). In some embodiments, Factor-4(−) is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the period in which subjects are receiving Factor-4(−), an analysis of the addiction can be made. Subjects are then switched to Factor-4 (the supplement that contains the Power Amino Acid Complex) for the remainder of the evaluation period. At various points during the period when subjects are receiving Factor-4, an analysis pertaining to addiction and/or addiction-related health concerns is made again. Measurements for both regimens (Factor-4 and Factor-4(−)) may include one or more surveys, questionnaires, interviews, or clinical or diagnostic techniques that are known in the art. The results from subjects who received supplementation with Factor-4(−) and Factor-4 can be compared. It will be found that a subject's addiction who received the Power Amino Acid Complex-containing formulation (i.e., Factor-4) can be lessened and/or eliminated compared to the subjects who did not receive the Power Amino Acid Complex (i.e., Factor-4(−)). One would expect to find improvements such as decreases in food addictions, decreases in sugar, fat, and salt addictions, decreases in caffeine addictions, decreases in smoking addictions, and decreases in drug and alcohol addictions. Additionally, subjects reported an acceleration of recovery from alcohol toxicity (hangovers). That is, in some embodiments, it is contemplated that addictions as measured by the methods listed above can be lessened or eliminated completely by consumption of a dietary supplement, as described herein.

EXAMPLE 29

Comparative Analysis Among Test Subjects Receiving the Power Amino Acid Complex, Factor-4(−), and Factor-4

The Power Amino Acid Complex comprises L-Lysine and/or L-Arginine and, in addition, at least one (1) amino acid selected from L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan). These amino acids are critical building blocks for enzymatic reactions in the body and are typically not provided at adequate levels in the diet. Supplementation of the Power Amino Acid Complex to the exclusion of others (consisting essentially of L-Lysine, L-Arginine, L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan)) can improve the health and well-being of a subject and provide the therapeutic benefits described herein. That is, it has been discovered that the Power Amino Acid Complex can be manufactured in many different formulations, and other amino acids or proteins are not required to receive a benefit.

One formulation of the Power Amino Acid Complex is oral. In particular, liquid formulations such as water (including variations of water such as Penta® Water) or various juices, with or without vitamins or other added supplements, may be used as the solvent with which the Power Amino Acid Complex is formulated. Other ingredients can comprise guar gum, lecithin, natural and artificial flavors, natural and artificial colors, fructo-oligosaccharide, and natural and artificial sweeteners. By providing the rate limiting amino acids, the Power Amino Acid Complex in water, for example, one can obtain the supplement and therapeutic benefits of the power amino acids while maintaining a low calorie intake.

In some embodiments a serving of the Power Amino Acid Complex can be less than, greater than, at least, or any number in between 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In one embodiment, a 2.2 g serving of the Power Amino Acid Complex contains amounts of each free-form power amino acid listed in Table 4.

In another embodiment, the Power Amino Acid Complex may be formulated with the Factor-4 Protein Complex plus other non-essential amino acids and nutrients referred to as Factor-4. By formulating the Power Amino Acid Complex with the Factor-4 Protein Complex as well as other nutrients, vitamins, and non-essential amino acids, one can obtain the therapeutic benefits of the Power Amino Acid Complex that the Factor-4 Protein Complex, non-essential amino acids, vitamins, and other nutrients alone do not provide.

In one embodiment, a dietary supplement is composed of a powder which comprises the Factor-4 dietary supplement described in Tables 2 and 3. In another embodiment, a dietary supplement, Factor-4 minus the Power Amino Acid Complex ("Factor-4(−)"), is composed of a powder which is comprised of the elements described in Tables 2 and 5. In some embodiments, a serving of the dietary supplements can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In an embodiment, a 16.5 g serving of Factor-4 or Factor-4(−) will provide amounts of each element as described in Tables 2 and 3 and Tables 2 and 5, respectively. Likewise, a 2.2 gram serving of the Power Amino Acid Complex contains amounts of each free-form power amino acid listed in Table 4.

A subject can be identified as one having one or more health or beauty concerns by surveys, questionnaires, interviews, or clinical or diagnostic techniques that are known in the art. Once a subject is identified as having any of the health concerns listed in Examples T-28 herein, said subject will be given the Power Amino Acid Complex, Factor-4(−), and by Factor-4. In some embodiments, the Power Amino Acid Complex is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of the health concern can be made. Measurements may include one or more surveys, questionnaires, interviews, or clinical or diagnostic techniques that are known in the art. The results from the post-supplementation measurements can be compared with the pre-supplementation measurements. Moreover, a cohort of test subjects will be given the Factor-4(−) (i.e., the supplement that does not contain the Power Amino Acid Complex) for a comparative evaluation. Similarly to subjects receiving the Power Amino Acid Complex, subjects are given the Factor-4(−) formulation provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. Subjects receiving the Factor-4(−) formulation are then switched to Factor-4 (i.e., the supplement that contains the Power Amino Acid Complex) for the remainder of the evaluation period. At various points during the period when subjects are receiving Factor-4, an analysis pertaining to the identified health concern is made again. Measurements for each of the regimens (Power Amino Acid Complex, Factor-4(−), and Factor-4) may include one or more surveys, questionnaires, interviews, or clinical or diagnostic techniques that are known in the art. The results from subjects who received supplementation with the Power Amino Acid Complex, Factor-4(−), and Factor-4 can be compared. It will be found that a subject's identified health concern who received the Power Amino Acid Complex alone (e.g. in water) or the Power Amino Acid Complex-containing formulation (i.e., Factor-4) can be lessened and/or eliminated compared to the subjects who did not receive the Power Amino Acid Complex (i.e., Factor-4(−)). In some embodiments, it is contemplated that a myriad of health concerns can be lessened or eliminated completely by consumption of a dietary supplement, as described herein.

EXAMPLE 30

Topical and Cosmetic Formulations Containing The Power Amino Acid Complex

The Power Amino Acid Complex comprises L-Lysine and/or L-Arginine and, in addition, at least one (1) amino acid selected from L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan). These amino acids are critical building blocks for enzymatic reactions in the body and are typically not provided at adequate levels in the diet. Supplementation of the Power Amino Acid Complex to the exclusion of others (consisting essentially of L-Lysine, L-Arginine, L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan)) can improve the health and well-being of a subject and provide the therapeutic benefits described herein. That is, it has been discovered that the Power Amino Acid Complex can be manufactured in many different formulations, and other amino acids or proteins are not required to receive a benefit.

One formulation of the Power Amino Acid Complex is topical. In particular, the Power Amino Acid Complex can be formulated for the skin in cosmetic formulations such as face and body lotions, creams, washes, gels, exfoliates, ointments, and oils. Other ingredients can comprise vitamins, natural extracts, fragrances, tints, and UV protection compounds. By providing the rate limiting amino acids found in the Power Amino Acid Complex, one can maintain a youthful appearance, reduce fine lines and wrinkles, and reduce the damage from the environment.

In some embodiments, an application of a topical formulation comprising the Power Amino Acid Complex can be less than, greater than, at least, or any number in between 50, 60, 70, 80, 90, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1250, 1500, 1750, 2000, 2200, 2250, 2500, 2750, 3000, 4000, 5000, 6000, 7000, 8000, 9000, 10000, 20000, 30000, 40000, 50000, 60000, 70000, 80000, 90000, or 100000 mg. In one embodiment, 1, 2, 3, 4, or 5 ml of the Power Amino Acid Complex-comprising cream contains amounts of each free-form power amino acid listed in Table 6.

A subject can be identified as having poor skin health and/or appearance by surveys, questionnaires, interviews, or clinical or diagnostic techniques that are known in the art. In some embodiments, a subject with poor skin health and/or appearance can be identified by evaluation of wrinkles, fine-line wrinkles, skin smoothness, skin moisturization, cellulite, age spots, acne, and elasticity/toneness. Identification of wrinkles (including fine-line wrinkles) can be accomplished by assessing the topography of the skin through visual and/or photographic means. Photographic devices, such as ClarityPro, use white and UV lights to capture images of the skin. A computer furnished with analytical software may be used with said camera to analyze the condition of the skin and provide a quantitative measurement of skin attributes such as depth and width of wrinkles, skin tone, pore quantity and pore size, and UV damage. Another common technique for Identifying and measuring wrinkles includes profilometry. Profilometry requires first making replicas of the skin (performed commonly with silica) followed by an evaluation of the skin mold. There are several different profilometry techniques known in the art including mechanical, optical, and transparency. Ultrasonography is another technique that may be used for evaluating wrinkles. Use of a high-resolution three-dimensional laser surface scanner to quantify skin surface morphology is yet another identification and measurement tool available. To identify the smoothness of subjects' skin, most of these techniques may also be utilized. Likewise, cellulite can be identified with most of the techniques aforementioned including photography, profilometry, and ultrasonography. Subjects with poor skin elasticity can be identified with a CUTOMETER® and/or Reviscometer. Subjects' skin moisturization may be identified by evaporimetry and corneometry. Age spots can be identified by photographic means with the assistance of a colorimeter such as the Konica Minolta Colorimeters. Acne can be identified by the Leeds technique and serum cyproterone acetate concentrations. The number and size of pores is another parameter to identify acne. The topographic evaluation techniques aforementioned are also used commonly to assess the number and size of pores. Biochemical evaluation of the pores' content may also be performed to identify acne. Many of these techniques overlap and may be used for Identifying most of the problematic skin features listed herein. Once a subject is identified as having skin-health concerns, said subject will be given topical creams with and without the Power Amino Acid Complex. In some embodiments, a topical cream without the Power Amino Acid Complex is first applied to the skin of identified subjects at least once, twice or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. During the period in which subjects are receiving a topical cream that does not comprise the Power Amino Acid Complex, subjects are measured for wrinkles, fine-line wrinkles, skin smoothness, skin moisturization, cellulite, age spots, acne, and elasticity/toneness. Measurements may also include one or more surveys, questionnaires, interviews, or clinical or diagnostic techniques that are known in the art. As described above, measurements aimed to quantify characteristics of the skin can include a variety of topography-based methods. Measurements of wrinkles, fine-lines, skin smoothness, and cellulite can be accomplished with photography using white and UV lights. Computer software attached to said photography device provides means to quantify features of skin aberrations such as the number and severity of wrinkles. Measurements for topographic skin features may include measuring the depth and width of wrinkles. Other measuring techniques include optical, mechanical, and/or transparency profilometry. Ultrasonography and laser surface scanners may also be employed for skin surface morphology measurements. Elasticity of subjects' skin can be measured with a CUTOMETER® and/or Reviscometer. For skin moisturization measurements, evaporimetry and/or comeometry can be used. Age spots can be measured by photographic means with the assistance of a colorimeter such as the Konica Minolta Colorimeters. Acne measurements may be taken by the Leeds technique and serum cyproterone acetate concentrations. Measurements of pore number, size, and/or their content may be taken. Subjects are then given the topical cream comprising the Power Amino Acid Complex for the remainder of the evaluation period. At various points during the period when subjects are receiving the Power Amino Acid Complex-comprising cream, subjects are measured again for wrinkles, fine-line wrinkles, skin smoothness, skin moisturization, cellulite, age spots, acne, and elasticity/toneness. As described above, measurements can include a variety of topography-based methods including profilometry and ultrasonography. Age spots, elasticity, and moisturization measurements can be taken with a calorimeter, CUTOMETER® and/or Reviscometer, and evaporimeter and/or comeometer, respectively. Measurements may also include one or more surveys, questionnaires, interviews, or clinical or diagnostic techniques that are known in the art. The results from subjects who received topical application of a cream with the addition of the Power Amino Acid Complex and a cream without the Power Amino Acid Complex can be compared. It will be found that the subjects' skin health and/or appearance who received the Power Amino Acid Complex are improved compared to the subjects who did not receive the Power Amino Acid Complex. One would expect to find improvements such as reduced depth and width of wrinkles and pores, skin that is smoother and less dry, reduced cellulite, reduced acne, tighter skin, and less color variation. That is, in some embodiments, it is contemplated that skin health and/or appearance can be improved or restored completely by topical application of a dietary supplement, as described herein.

Other topical cosmetic formulations include formulations for hair. In particular, the Power Amino Acid Complex can be formulated for hair in formulations such as shampoos, conditioners, gels, styling products, and oil treatments. Other ingredients can comprise vitamins, natural extracts, fragrances, tints and colors, and UV protection compounds. By providing the rate limiting amino acids found in the Power Amino Acid Complex, one can strengthen, restore, repair, reduce the damage from the environment, and maintain manageability for healthy looking hair.

In some embodiments an application of hair product comprising the Power Amino Acid Complex can be less than, greater than, at least, or any number in between 50, 60, 70, 80, 90, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1250, 1500, 1750, 2000, 2200, 2250, 2500, 2750, 3000, 4000, 5000, 6000, 7000, 8000, 9000, 10000, 20000, 30000, 40000, 50000, 60000, 70000, 80000, 90000, or 100000 mg. In one embodiment, 1, 2, 3, 4, or 5 ml of the Power Amino Acid Complex-comprising hair product contains amounts of each free-form power amino acid listed in Table 6.

A subject can be identified as having unhealthy, thin, unappealing and/or damaged hair by surveys, questionnaires, interviews, or clinical or diagnostic techniques that are known in the art. In some embodiments, a subject with unhealthy and/or damaged hair can be identified by evaluation of combability, strength, thickness, porosity, split ends, hair shine, amino acid composition, lipid content, alkaline solubility, copper uptake, and discoloration. Identification of poor combability can be assessed by the combing force. Tensile and flexabrasion testing can identify weak hair. Identification of thin hair, hair porosity, and split ends can be accomplished with a scanning electron microscope and/or other microscopy imaging. Identifying hair lacking in shine may be achieved with a photogoniometer and/or other imaging analyses. Identifying hair with substandard amino acid and lipid compositions can be carried out by common techniques known in the art such as using spectrophotometric-, calorimetric-, or chromatographic-based assays. Alkaline soluble hair can be identified by assessing the hairs' rate of solubility in the presence of non-acidic (i.e., basic) solvents. The copper uptake of hair is another Identifying hallmark of hair quality. Identifying said subjects can be accomplished by copper absorbent techniques such as colorimetric-based techniques. Colorimetric techniques may also identify discolored hair. Once a subject is identified as having unhealthy, thin, unappealing and/or damaged hair, said subject will be given hair treatments with and without the Power Amino Acid Complex. In some embodiments, hair treatment without the Power Amino Acid Complex is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. During the period in which subjects are using a hair product that does not comprise the Power Amino Acid Complex, subjects are measured for combability, strength, thickness, porosity, split ends, hair shine, amino acid composition, lipid content, alkaline solubility, copper uptake, and discoloration. Measurements may also include one or more surveys, questionnaires, interviews, or clinical or diagnostic techniques that are known in the art. As described above, measurements for combability can be taken by changes in combing force. Hair thickness, porosity, and split ends may be measured with a scanning electron microscope and/or other microscopic imaging. Hair strength can be measured by tensile and flexabrasion testing. Photogoniometric measurements can be taken to assess hair shine. The hairs' amino acid and lipid composition can be measured with a number of common techniques known in the art such as chromatography. Measurements for its alkaline solubility may be determined by its solubility rate in the presence of a base. A subject's hairs' copper uptake may be assessed calorimetrically by measuring the remaining copper in a vial after incubating the subjects' hair in a copper-based solution. Discoloration measurements can be taken with various reflectometer devices using parameters such as the Commission International d'Eclairage (CIE) L*a*b* system Said reflectometer devices may include the Photovolt ColorWalk (a tristimulus calorimeter) and/or the DermaSpectrometer (a narrow-band reflectometer). Other spectrometric and/or colorimetric devices may be employed. Subjects are then switched to hair treatment comprising the Power Amino Acid Complex for the remainder of the evaluation period. At various points during the period when subjects are receiving the Power Amino Acid Complex-comprising hair product, subjects are measured again for combability, strength, thickness, porosity, split ends, hair shine, amino acid composition, lipid content, alkaline solubility, copper uptake, and discoloration. As described above, measurements for hair strength may be taken by tensile and flexabrasion testing. Hair thickness, porosity, and split ends may be measured with a scanning electron microscope and/or other microscopic imaging. The remaining parameters are measured using techniques such as reflectometry and chromatography as they have been described herein. Measurements for both regimens (topical creams with and without the Power Amino Acid Complex) may also include one or more surveys, questionnaires, interviews, or clinical or diagnostic techniques that are known in the art. The results from subjects who received topical application with the Power Amino Acid Complex can be compared. It will be found that the subjects' hair health and/or appearance who received the Power Amino Acid Complex-containing formulation are improved compared to the subjects who did not receive the Power Amino Acid Complex. One would expect to find improvements such as an increase in hair strength, an increase in hair thickness, a decrease in porosity, a reduction of split ends, an increase in shine, an increase of amino acids and lipids, a decrease in thiol content, a decrease in alkaline solubility, a decrease in copper uptake, and a reduction in color loss/fading. That is, in some embodiments, it is contemplated that hair health and/or appearance can be improved or restored completely by topical application of a dietary supplement, as described herein.

The Power Amino Acid Complex comprises L-Lysine and/or L-Arginine and, in addition, at least one (1) amino acid selected from L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan). These amino acids are critical building blocks for enzymatic reactions in the body and are typically not provided at adequate levels in the diet. Supplementation of the Power Amino Acid Complex to the exclusion of others (consisting essentially of L-Lysine, L-Arginine, L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan)) can improve the health and well-being of a subject and provide the therapeutic benefits described herein. That is, it has been discovered that the Power Amino Acid Complex can be manufactured in many different formulations, and other amino acids or proteins are not required to receive a benefit.

TABLE 6

| L-Arginine HCl | 250 mg |
|---|---|
| L-Lysine HCl | 250 mg |
| L-Isoleucine | 50 mg |
| dl-Phenylalanine (or L-Phenylalanine) | 50 mg |
| L-Methionine | 50 mg |
| L-Leucine | 50 mg |
| L-Valine | 50 mg |
| L-Threonine | 50 mg |
| L-Histidine HCl | 250 mg |
| 5-Hydroxy Tryptophan (or L-Hydroxy Tryptophan or L-Tryptophan) | 50 mg |

EXAMPLE 31

Oral Formulations Containing the Power Amino Acid Complex Improves Nutritional Deficiencies Associated With Eating Disorders The Power Amino Acid Complex comprises L-Lysine and/or L-Arginine and, in addition, at least one (1) amino acid selected from L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan). These amino acids are critical building blocks for enzymatic reactions in the body and are typically not provided at adequate levels in the diet. Supplementation of the Power Amino Acid Complex to the exclusion of others (consisting essentially of L-Lysine, L-Arginine, L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan)) can improve the health and well-being of a subject and provide the therapeutic benefits described herein. That is, it has been discovered that the Power Amino Acid Complex can be manufactured in many different formulations, and other amino acids or proteins are not required to receive a benefit.

One formulation of the Power Amino Acid Complex is oral. In particular, liquid formulations such as water (including variations of water such as Penta® Water) or various juices, with or without vitamins or other added supplements, may be used as the solvent with which the Power Amino Acid Complex is formulated. Other ingredients can comprise guar gum, lecithin, natural and artificial flavors, natural and artificial colors, fructo-oligosaccharide, and natural and artificial sweeteners. By providing the rate limiting amino acids, the Power Amino Acid Complex in water, for example, one can obtain the supplement and therapeutic benefits of the power amino acids while maintaining a low calorie intake.

In some embodiments a serving of the Power Amino Acid Complex can be less than, greater than, at least, or any number in between 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In one embodiment, a 2.2 g serving of the Power Amino Acid Complex contains amounts of each free-form power amino acid listed in Table 4.

A subject can be identified as one having one or more eating disorders by surveys, questionnaires, interviews, or clinical or diagnostic techniques that are known in the art. Eating disorders are those conditions which may lead to protein deficiency. Eating disorders may include, but are not limited to, overweight disorders, obesity, "vegetarian" and "vegan" diets, bulimia, anorexia, hormonal disorders, refusing food, skipping meals, chronic hunger or self-imposed starvation. Once a subject is identified as having an eating disorder, said subject will be given the Power Amino Acid Complex. In some embodiments, the Power Amino Acid Complex is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of the eating disorder can be made. Measurements may include one or more surveys, questionnaires, interviews, or clinical or diagnostic techniques that are known in the art. The results from the post-supplementation measurements can be compared with the pre-supplementation measurements. It will be found that a subject's eating disorder who received the Power Amino Acid Complex can be lessened and/or eliminated compared to subjects who did not receive the Power Amino Acid Complex. One would expect to find improvements such as decreases in excess fat storage, decreases in catabolic reactions that breakdown muscle tissue leading to increased body fat as well as poor muscle tone and body definition, increased energy and performance, decreases in sluggish behavior and poor brain function, decreases in episodes of anger, rage, aggression or uncontrolled mood swings, decreases in anxiety reactions, panic attacks and fear states, decreases in attention deficit and obsessive-compulsive disorders, depression, loss of self-esteem and/or suicidal tendencies, and/or decreases in food cravings, hunger attacks, famished states and eating binges. That is, in some embodiments, it is contemplated that eating disorders as measured by the methods listed above can be lessened or eliminated completely by consumption of a dietary supplement, as described herein.

Although the precise mechanism is unknown, it is believed that the Power Amino Acid Complex restores body health in persons suffering from eating disorders, rebuilds the body leading to better health, corrects protein deficiency syndrome, which leads to overweight disorders and obesity, suppresses appetite thereby blocking food cravings, hunger attacks, famished states and binge eating, enhances feelings of comfort, satisfaction and well-being without ingesting "comfort" food rich in carbohydrates, removes the "sweet tooth" that leads to the "food-swing trap" that results in the yo-yo metabolism of increased hunger, stimulates loss of unwanted body fat and achieves sustained weight control without food cravings, hunger attacks or famished states, avoids the catabolic effects of eating disorders while maintaining the anabolic effects of body shape, youth and health, maintains body shape and body tone without increasing body fat, stimulates significant weight loss and sustained weight control, combats the Metabolic Syndrome associated with accelerated aging, establishes the trim, athletic and sexy body that young women desire, stimulates pep, energy, activity, stamina, endurance and performance, and provides a lean and attractive body.

In another embodiment, the Power Amino Acid Complex may be formulated with the Factor-4 Protein Complex plus other non-essential amino acids and nutrients referred to as Factor-4. By formulating the Power Amino Acid Complex with the Factor-4 Protein Complex as well as other nutrients, vitamins, and non-essential amino acids, one can obtain the therapeutic benefits of the Power Amino Acid Complex that the Factor-4 Protein Complex, non-essential amino acids, vitamins, and other nutrients alone do not provide.

In one embodiment, a dietary supplement is composed of a powder which comprises the Factor-4 dietary supplement described in Tables 2 and 3. In another embodiment, a dietary supplement, Factor-4 minus the Power Amino Acid Complex ("Factor-4(−)"), is composed of a powder which is comprised of the elements described in Tables 2 and 5. In some embodiments, a serving of the dietary supplements can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In an embodiment, a 16.5 g serving of Factor-4 or Factor-4(−) will provide amounts of each element as described in Tables 2 and 3 and Tables 2 and 5, respectively.

A subject can be identified as one having an eating disorder by surveys, questionnaires, interviews, or clinical or diagnostic techniques that are known in the art. Eating disorders are those conditions which may lead to protein deficiency. Eating disorders may include, but are not limited to, overweight disorders, obesity, "vegetarian" and "vegan" diets, bulimia, anorexia, hormonal disorders, refusing food, skipping meals, chronic hunger or self-imposed starvation. Once a subject is identified as having an eating disorder, said subject will be given Factor-4 and Factor-4(−). In some embodiments, Factor-4(−) is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the period in which subjects are receiving Factor-4(−), an analysis of the eating disorder can be made. Subjects are then switched to Factor-4 (the supplement that contains the Power Amino Acid Complex) for the remainder of the evaluation period. At various points during the period when subjects are receiving Factor-4, an analysis pertaining to eating disorder and/or eating disorder-related health concerns is made again. Measurements for both regimens (Factor-4 and Factor-4(−)) may include one or more surveys, questionnaires, interviews, or clinical or diagnostic techniques that are known in the art. The results from subjects who received supplementation with Factor-4(−) and Factor-4 can be compared. It will be found that a subject's eating disorder who received the Power Amino Acid Complex-containing formulation (i.e., Factor-4) can be lessened and/or eliminated compared to the subjects who did not receive the Power Amino Acid Complex (i.e., Factor-4(−)). One would expect to find improvements such as decreases in excess fat storage, decreases in catabolic reactions that breakdown muscle tissue leading to increased body fat as well as poor muscle tone and body definition, increased energy and performance, decreases in sluggish behavior and poor brain function, decreases in incidents of anger, rage, aggression and uncontrolled mood swings, decreases in anxiety reactions, panic attacks or fear states, decreases in attention deficit and obsessive-compulsive disorders, depression, loss of self-esteem and/or suicidal tendencies, and/or decreases in food cravings, hunger attacks, famished states and eating binges. That is, in some embodiments, it is contemplated that eating disorders as measured by the methods listed above can be lessened or eliminated completely by consumption of a dietary supplement, as described herein.

Although the precise mechanism is unknown, it is believed that FACTOR-4 WEIGHT CONTROL® restores body health in persons suffering from eating disorders, rebuilds the body with POWER AMINO ACIDS® leading to better health, corrects protein deficiency syndrome, which leads to overweight disorders and obesity, suppresses appetite thereby blocking food cravings, hunger attacks, famished states and binge eating, enhances feelings of comfort, satisfaction and well-being without ingesting "comfort" food rich in carbohydrates, removes the "sweet tooth" that leads to the "food-swing trap" that results in the yo-yo metabolism of increased hunger, stimulates loss of unwanted body fat and achieves sustained weight control without food cravings, hunger attacks or famished states, avoids the catabolic effects of eating disorders while maintaining the anabolic effects of body shape, youth and health, maintains body shape and body tone without increasing body fat, stimulates significant weight loss and sustained weight control, combats the Metabolic Syndrome associated with accelerated aging, establishes the trim, athletic and sexy body that young women desire, stimulates pep, energy, activity, stamina, endurance and performance, and provides a lean and attractive body.

EXAMPLE 32

Oral Formulations Containing the Power Amino Acid Complex Improves Anxiety Reactions The Power Amino Acid Complex comprises L-Lysine and/or L-Arginine and, in addition, at least one (1) amino acid selected from L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan). These amino acids are critical building blocks for enzymatic reactions in the body and are typically not provided at adequate levels in the diet. Supplementation of the Power Amino Acid Complex to the exclusion of others (consisting essentially of L-Lysine, L-Arginine, L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan)) can improve the health and well-being of a subject and provide the therapeutic benefits described herein. That is, it has been discovered that the Power Amino Acid Complex can be manufactured in many different formulations, and other amino acids or proteins are not required to receive a benefit.

One formulation of the Power Amino Acid Complex is oral. In particular, liquid formulations such as water (including variations of water such as PENTA® Water) or various juices, with or without vitamins or other added supplements, may be used as the solvent with which the Power Amino Acid Complex is formulated. Other ingredients can comprise guar gum, lecithin, natural and artificial flavors, natural and artificial colors, fructo-oligosaccharide, and natural and artificial sweeteners. By providing the rate limiting amino acids, the Power Amino Acid Complex in water, for example, one can obtain the supplement and therapeutic benefits of the power amino acids while maintaining a low calorie intake.

A subject can be identified as one having one or more anxiety reactions, which may include, but are not limited to panic attacks, fear, mood swings and/or bouts of depression. A subject can be identified by surveys, questionnaires, interviews, or clinical or diagnostic techniques that are known in the art. Once a subject is identified as having an anxiety reaction said subject will be given the Power Amino Acid Complex. In some embodiments, the Power Amino Acid Complex is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of the anxiety reaction can be made. Measurements may include one or more surveys, questionnaires, interviews, or clinical or diagnostic techniques that are known in the art. The results from the post-supplementation measurements can be compared with the pre-supplementation measurements. It will be found that a subject's anxiety reaction who received the Power Amino Acid Complex can be lessened and/or eliminated compared to subjects who did not receive the Power Amino Acid Complex. One would expect to find improvements such as decreases in frequency and/or severity of anxiety reactions. Such improvements may include calming effects, stabilizing mood swings, increasing quality of life with feelings of comfort, satisfaction and well-being, relaxing the body to provide and enhance restful sleep, reducing anger, stress, rage and/or aggression, relieving depression, relieving drug and alcohol dependency, increasing pep, energy, activity, stamina and/or endurance, and/or increasing clarity of thought leading to sharper memory and focus of cognitive efforts. Additionally, subjects reported an acceleration of recovery from anxiety reactions and/or panic attacks. That is, in some embodiments, it is contemplated that frequency and or severity of anxiety reactions and/or panic attacks as measured by the methods listed above can be lessened or eliminated completely by consumption of a dietary supplement, as described herein. Although a precise mechanism is unknown, it is believed that poor nutritional health associated with Metabolic Syndrome is one of the major causes of mood swings, anxiety reactions and panic attacks. Amino acid deficiencies lead to an imbalance in neurotransmitters in the brain that causes mood swings, anxiety reactions, and panic attacks. POWER AMINO ACIDS® contained in FACTOR-4 WEIGHT CONTROL® correct the amino acid deficiencies and reset (rebalance) the neurotransmitters in the brain, causing the brain to return to normal psychological health.

In another embodiment, the Power Amino Acid Complex may be formulated with the Factor-4 Protein Complex plus other non-essential amino acids and nutrients referred to as Factor-4. By formulating the Power Amino Acid Complex with the Factor-4 Protein Complex as well as other nutrients, vitamins, and non-essential amino acids, one can obtain the therapeutic benefits of the Power Amino Acid Complex that the Factor-4 Protein Complex, non-essential amino acids, vitamins, and other nutrients alone do not provide.

In one embodiment, a dietary supplement is composed of a powder which comprises the Factor-4 dietary supplement described in Tables 2 and 3. In another embodiment, a dietary supplement, Factor-4 minus the Power Amino Acid Complex ("Factor-4(−)"), is composed of a powder which is comprised of the elements described in Tables 2 and 5. In some embodiments, a serving of the dietary supplements can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In an embodiment, a 16.5 g serving of Factor-4 or Factor-4(−) will provide amounts of each element as described in Tables 2 and 3 and Tables 2 and 5, respectively.

A subject can be identified as one having one or more anxiety reactions, which may include, but are not limited to panic attacks, fear, mood swings and/or bouts of depression. A subject can be identified by surveys, questionnaires, interviews, or clinical or diagnostic techniques that are known in the art. Once a subject is identified as having an anxiety reaction, said subject will be given Factor-4 and Factor-4(−). In some embodiments, Factor-4(−) is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the period in which subjects are receiving Factor-4(−), an analysis of the anxiety reactions can be made. Subjects are then switched to Factor-4 (the supplement that contains the Power Amino Acid Complex) for the remainder of the evaluation period. At various points during the period when subjects are receiving Factor-4, an analysis pertaining to anxiety reactions and/or anxiety-related health concerns is made again. Measurements for both regimens (Factor-4 and Factor-4(−)) may include one or more surveys, questionnaires, interviews, or clinical or diagnostic techniques that are known in the art. The results from subjects who received supplementation with Factor-4(−) and Factor-4 can be compared. It will be found that a subject's anxiety reactions who received the Power Amino Acid Complex-containing formulation (i.e., Factor-4) can be lessened and/or eliminated compared to the subjects who did not receive the Power Amino Acid Complex (i.e., Factor-4(−)). One would expect to find improvements such as decreases in frequency and/or severity of anxiety reactions. Such improvements may include calming effects, stabilizing mood swings, increasing quality of life with feelings of comfort, satisfaction and well-being, relaxing the body to provide and enhance restful sleep, reducing anger, stress, rage and/or aggression, relieving depression, relieving drug and alcohol dependency, increasing pep, energy, activity, stamina and/or endurance, and/or increasing clarity of thought leading to sharper memory and focus of cognitive efforts. Additionally, subjects reported an acceleration of recovery from anxiety reactions and/or panic attacks. That is, in some embodiments, it is contemplated that frequency and or severity of anxiety reactions and/or panic attacks as measured by the methods listed above can be lessened or eliminated completely by consumption of a dietary supplement, as described herein. Although a precise mechanism is unknown, it is thought that poor nutritional health associated with Metabolic Syndrome is one of the major causes of mood swings, anxiety reactions and panic attacks. Amino acid deficiencies lead to an imbalance in neurotransmitters in the brain that causes mood swings, anxiety reactions, and panic attacks. POWER AMINO ACIDS® contained in FACTOR-4 WEIGHT CONTROL® correct the amino acid deficiencies and reset (rebalance) the neurotransmitters in the brain, causing the brain to return to normal psychological health. One would expect to find improvements such as decreases in frequency and/or severity of anxiety reactions. Such improvements may include calming effects, stabilizing mood swings, increasing quality of life with feelings of comfort, satisfaction and well-being, relaxing the body to provide and enhance restful sleep, reducing anger, stress, rage and/or aggression, relieving depression, relieving drug and alcohol dependency, increasing pep, energy, activity, stamina and/or endurance, and/or increasing clarity of thought leading to sharper memory and focus of cognitive efforts. Additionally, subjects reported an acceleration of recovery from anxiety reactions and/or panic attacks. That is, in some embodiments, it is contemplated that frequency and or severity of anxiety reactions and/or panic attacks as measured by the methods listed above can be lessened or eliminated completely by consumption of a dietary supplement, as described herein. Although a precise mechanism is unknown, it is thought that poor nutritional health associated with Metabolic Syndrome is one of the major causes of mood swings, anxiety reactions and panic attacks. Amino acid deficiencies lead to an imbalance in neurotransmitters in the brain that causes mood swings, anxiety reactions, and panic attacks. Power Amino Acids™ contained in Factor4 Weight Control™ correct the amino acid deficiencies and reset (rebalance) the neurotransmitters in the brain, causing the brain to return to normal psychological health.

EXAMPLE 33

Oral Formulations Containing the Power Amino Acid Complex Improves Symptoms of Post-Traumatic Stress The Power Amino Acid Complex comprises L-Lysine and/or L-Arginine and, in addition, at least one (1) amino acid selected from L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan). These amino acids are critical building blocks for enzymatic reactions in the body and are typically not provided at adequate levels in the diet. Supplementation of the Power Amino Acid Complex to the exclusion of others (consisting essentially of L-Lysine, L-Arginine, L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan)) can improve the health and well-being of a subject and provide the therapeutic benefits described herein. That is, it has been discovered that the Power Amino Acid Complex can be manufactured in many different formulations, and other amino acids or proteins are not required to receive a benefit.

One formulation of the Power Amino Acid Complex is oral. In particular, liquid formulations such as water (including variations of water such as Penta® Water) or various juices, with or without vitamins or other added supplements, may be used as the solvent with which the Power Amino Acid Complex is formulated. Other ingredients can comprise guar gum, lecithin, natural and artificial flavors, natural and artificial colors, fructo-oligosaccharide, and natural and artificial sweeteners. By providing the rate limiting amino acids, the Power Amino Acid Complex in water, for example, one can obtain the supplement and therapeutic benefits of the power amino acids while maintaining a low calorie intake.

In some embodiments a serving of the Power Amino Acid Complex can be less than, greater than, at least, or any number in between 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In one embodiment, a 2.2 g serving of the Power Amino Acid Complex contains amounts of each free-form power amino acid listed in Table 4.

A subject can be identified as one having symptoms associated with post-traumatic stress by surveys, questionnaires, interviews, or clinical or diagnostic techniques that are known in the art. Symptoms associated with post-traumatic stress may include, but are not limited to wide mood swings, insomnia, nightmares, anxiety attacks, anger reactions and loss of cognitive skills accompanied by "hollow vacant eyes." Once a subject is identified as having symptoms associated with post-traumatic stress, said subject will be given the Power Amino Acid Complex. In some embodiments, the Power Amino Acid Complex is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of the symptoms associated with post-traumatic stress can be made. Measurements may include one or more surveys, questionnaires, interviews, or clinical or diagnostic techniques that are known in the art. The results from the post-supplementation measurements can be compared with the pre-supplementation measurements. It will be found that a subject's symptoms associated with post-traumatic stress who received the Power Amino Acid Complex can be lessened and/or eliminated compared to subjects who did not receive the Power Amino Acid Complex. One would expect to find improvements such as decreases in symptoms associated with post-traumatic stress, increases in amino acid precursors for neurotransmitter health, increases in clarity of thought, increases in memory, increases in calming effect that stabilizes mood, increases in feelings of comfort, satisfaction and well-being, increases in relaxing the body and enhancing restful sleep, decreases in anger, stress, rage and aggression, decreases in incidents of depression, increases in help to relieve drug and alcohol dependency and increases pep, energy, activity, stamina and endurance. Additionally, subjects reported an acceleration of recovery from symptoms associated with post-traumatic stress. That is, in some embodiments, it is contemplated that symptoms associated with post-traumatic stress as measured by the methods listed above can be lessened or eliminated completely by consumption of a dietary supplement, as described herein.

In another embodiment, the Power Amino Acid Complex may be formulated with the Factor-4 Protein Complex plus other non-essential amino acids and nutrients referred to as Factor-4. By formulating the Power Amino Acid Complex with the Factor-4 Protein Complex as well as other nutrients, vitamins, and non-essential amino acids, one can obtain the therapeutic benefits of the Power Amino Acid Complex that the Factor-4 Protein Complex, non-essential amino acids, vitamins, and other nutrients alone do not provide.

In one embodiment, a dietary supplement is composed of a powder which comprises the Factor-4 dietary supplement described in Tables 2 and 3. In another embodiment, a dietary supplement, Factor-4 minus the Power Amino Acid Complex ("Factor-4(−)"), is composed of a powder which is comprised of the elements described in Tables 2 and 5. In some embodiments, a serving of the dietary supplements can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In an embodiment, a 16.5 g serving of Factor-4 or Factor-4(−) will provide amounts of each element as described in Tables 2 and 3 and Tables 2 and 5, respectively.

A subject can be identified as one having symptoms associated with post-traumatic stress by surveys, questionnaires, interviews, or clinical or diagnostic techniques that are known in the art. Symptoms associated with post-traumatic stress disorders may include, but are not limited to wide mood swings, insomnia, nightmares, anxiety attacks, anger reactions and loss of cognitive skills accompanied by "hollow vacant eyes." Once a subject is identified as having symptoms associated with post-traumatic stress, said subject will be given Factor-4 and Factor-4(−). In some embodiments, Factor-4(−) is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the period in which subjects are receiving Factor-4(−), an analysis of the post-traumatic stress can be made. Subjects are then switched to Factor-4 (the supplement that contains the Power Amino Acid Complex) for the remainder of the evaluation period. At various points during the period when subjects are receiving Factor-4, an analysis pertaining to symptoms associated with post-traumatic stress and/or post-traumatic stress-related health concerns is made again. Measurements for both regimens (Factor-4 and Factor-4(−)) may include one or more surveys, questionnaires, interviews, or clinical or diagnostic techniques that are known in the art. The results from subjects who received supplementation with Factor-4(−) and Factor-4 can be compared. It will be found that a subject's symptoms associated with post-traumatic stress who received the Power Amino Acid Complex-containing formulation (i.e., Factor-4) can be lessened and/or eliminated compared to the subjects who did not receive the Power Amino Acid Complex (i.e., Factor-4(−)). One would expect to find improvements such as decreases in symptoms associated with post-traumatic stress, increases in amino acid precursors for neurotransmitter health, increases in clarity of thought, increases in memory, increases in calming effect that stabilizes mood, increases in feelings of comfort, satisfaction and well-being, increases in relaxing the body and enhancing restful sleep, decreases in anger, stress, rage and aggression, decreases in incidents of depression, increases in help to relieve drug and alcohol dependency and increases pep, energy, activity, stamina and endurance. Additionally, subjects reported an acceleration of recovery from symptoms associated with post-traumatic stress. That is, in some embodiments, it is contemplated that symptoms associated with post-traumatic stress as measured by the methods listed above can be lessened or eliminated completely by consumption of a dietary supplement, as described herein.

EXAMPLE 34

Oral Formulations Containing the Power Amino Acid Complex Improves Muscle Bulk

The Power Amino Acid Complex comprises L-Lysine and/or L-Arginine and, in addition, at least one (1) amino acid selected from L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan). These amino acids are critical building blocks for enzymatic reactions in the body and are typically not provided at adequate levels in the diet. Supplementation of the Power Amino Acid Complex to the exclusion of others (consisting essentially of L-Lysine, L-Arginine, L-Isoleucine, L-Leucine, L-Threonine, L-Valine, dl-Phenylalanine (or L-Phenylalanine), L-Methionine, L-Histidine, and 5-Hydroxy Tryptophan (or L-Hydroxy Tryptophan or L-Tryptophan)) can improve the health and well-being of a subject and provide the therapeutic benefits described herein. That is, it has been discovered that the Power Amino Acid Complex can be manufactured in many different formulations, and other amino acids or proteins are not required to receive a benefit.

One formulation of the Power Amino Acid Complex is oral. In particular, liquid formulations such as water (including variations of water such as Penta® Water) or various juices, with or without vitamins or other added supplements, may be used as the solvent with which the Power Amino Acid Complex is formulated. Other ingredients can comprise guar gum, lecithin, natural and artificial flavors, natural and artificial colors, fructo-oligosaccharide, and natural and artificial sweeteners. By providing the rate limiting amino acids, the Power Amino Acid Complex in water, for example, one can obtain the supplement and therapeutic benefits of the power amino acids while maintaining a low calorie intake.

In some embodiments a serving of the Power Amino Acid Complex can be less than, greater than, at least, or any number in between 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In one embodiment, a 2.2 g serving of the Power Amino Acid Complex contains amounts of each free-form power amino acid listed in Table 4. In some embodiments the Power Amino Acid Complex is combined with one or more weight-training and/or muscle building products known in the art.

A subject can be identified as one having the desire to build up muscle bulk by surveys, questionnaires, interviews, or clinical or diagnostic techniques that are known in the art. Increasing muscle bulk may include, but is not limited to, increasing muscle mass and/or improving muscle definition. Once a subject is identified as having the desire to build up muscle bulk, said subject will be given the Power Amino Acid Complex. In some embodiments, the Power Amino Acid Complex is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the supplementation period, an analysis of muscle bulk can be made. Measurements may include one or more surveys, questionnaires, interviews, or clinical or diagnostic techniques that are known in the art. The results from the post-supplementation measurements can be compared with the pre-supplementation measurements. It will be found that a subject's muscle bulk who received the Power Amino Acid Complex can be improved and/or increased compared to subjects who did not receive the Power Amino Acid Complex. One would expect to find improvements such as rebuilding the body with POWER AMINO ACIDS®, increasing protein health throughout the body, increasing strength and improving endurance allowing increased numbers of repetitions and longer workout periods, reducing post-workout recovery times, increasing muscle tone and body definition, increasing muscle bulk and improving muscle definition, stimulating loss of body fat with decreased body mass index (BMI), achieving higher energy levels and sustained energy reserves throughout the day, improving muscle relaxation with diminished muscle cramps decreasing the need for extended periods of muscle stretching, diminishing muscle cramps and soreness associated with extreme workouts and exercise, and converting catabolic reactions to anabolic processes that accelerate the healing of micro tears in muscle tissue. That is, in some embodiments, it is contemplated that muscle bulk as measured by the methods listed above can be improved or increased completely by consumption of a dietary supplement, as described herein.

In another embodiment, the Power Amino Acid Complex may be formulated with the Factor-4 Protein Complex plus other non-essential amino acids and nutrients referred to as Factor-4. By formulating the Power Amino Acid Complex with the Factor-4 Protein Complex as well as other nutrients, vitamins, and non-essential amino acids, one can obtain the therapeutic benefits of the Power Amino Acid Complex that the Factor-4 Protein Complex, non-essential amino acids, vitamins, and other nutrients alone do not provide.

In one embodiment, a dietary supplement is composed of a powder which comprises the Factor-4 dietary supplement described in Tables 2 and 3. In another embodiment, a dietary supplement, Factor-4 minus the Power Amino Acid Complex ("Factor-4(–)"), is composed of a powder which is comprised of the elements described in Tables 2 and 5. In some embodiments, a serving of the dietary supplements can be less than, greater than, at least, or any number in between 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 30, 40, 50, 60, 70, 80, 90 or 100 grams. In an embodiment, a 16.5 g serving of Factor-4 or Factor-4(–) will provide amounts of each element as described in Tables 2 and 3 and Tables 2 and 5, respectively. In some embodiments the Factor-4 or Factor-4(–) supplement is combined with one or more weight-training and/or muscle building products known in the art.

A subject can be identified as one having the desire to increase muscle bulk by surveys, questionnaires, interviews, or clinical or diagnostic techniques that are known in the art. Increasing muscle bulk may include, but is not limited to, increasing muscle mass and/or improving muscle definition. Once a subject is identified as having the desire to increase muscle bulk, said subject will be given Factor-4 and Factor-4(–). In some embodiments, Factor-4(–) is provided at least once, twice, or three times a day for a set period, which can be at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, less than, greater than, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. At various time points during the period in which subjects are receiving Factor-4(–), an analysis of the muscle bulk can be made. Subjects are then switched to Factor-4 (the supplement that contains the Power Amino Acid Complex) for the remainder of the evaluation period. At various points during the period when subjects are receiving Factor-4, an analysis pertaining to muscle bulk and/or muscle bulk-related health concerns is made again. Measurements for both regimens (Factor-4 and Factor-4(–)) may include one or more surveys, questionnaires, interviews, or clinical or diagnostic techniques that are known in the art. The results from subjects who received supplementation with Factor-4(–) and Factor-4 can be compared. It will be found that a subject's muscle bulk who received the Power Amino Acid Complex-containing formulation (i.e., Factor-4) can be improved and/or increased compared to the subjects who did not receive the Power Amino Acid Complex (i.e., Factor-4(–)). One would expect to find improvements such as rebuilding the body with POWER AMINO ACIDS®, increasing protein health throughout the body, increasing strength and improving endurance allowing increased numbers of repetitions and longer workout periods, reducing post-workout recovery times, increasing muscle tone and body definition, increasing muscle bulk and improving muscle definition, stimulating loss of body fat with decreased body mass index (BMI), achieving higher energy levels and sustained energy reserves throughout the day, improving muscle relaxation with diminished muscle cramps decreasing the need for extended periods of muscle stretching, diminishing muscle cramps and soreness associated with extreme workouts and exercise, and converting catabolic reactions to anabolic processes that accelerate the healing of micro tears in muscle tissue. That is, in some embodiments, it is contemplated that muscle bulk as measured by the methods listed above can be improved or increased completely by consumption of a dietary supplement, as described herein.

EXAMPLE 35

Optimal Health

Protein deficient diets fed to laboratory animals, over a 12 day period, resulted in a 90-95% decrease in the synthesis of positive-charged proteins within the pancreas. In contrast, the synthesis of negative-charged proteins in the pancreas was unchanged. The imbalance in protein synthesis observed in the pancreas can be expected to occur in other organs and tissues throughout the body and lead to major compromises in body health.

Although 20 amino acids are required for protein synthesis throughout a mammalian body, humans and other mammals are capable of producing 11 of these amino acids in the body. Thus, with respect to the diet, these amino acids are called "non-essential" because it is not necessary to obtain them from dietary sources. "Essential" amino acids must be obtained through the diet. Traditional diets are normally rich in amino acids from meat, chicken, fish or dairy products. However, when the food chain suffers from poor eating habits or the aging process, humans become deficient in essential amino acids and, like the experimental animals, lose the ability to produce positive-charged proteins. Loss of positive-charged proteins results in an imbalance of proteins separated on 2D gels. Each human needs to field a complete set of proteins to achieve "optimal" or "supercharged" health.

The correction of all these disorders is rendered by the group of 9 essential amino acids and the 3 positive-charged amino acids (two overlap giving a total of 10). When added together they include 10 amino acids, including Lysine and Arginine and the other 8 essentials. The rest of the "non-essential" amino acids are not needed for the therapeutic benefits.

FACTOR-4 WEIGHT CONTROL®, containing POWER AMINO ACIDS®, vitamins, minerals and micronutrients, to repair the body when it is suffering because of a deficiency in "essential" amino acids. FACTOR-4 WEIGHT CONTROL®, containing POWER AMINO ACIDS®, corrects the deficiency in "essential" amino acids, closes the food chain gap, corrects the imbalance in protein synthesis between positive- and negative-charged proteins and restores supercharged health.

A weight loss study conducted in 2006 demonstrates that 96% of subjects lost weight within 3 months and continued to lose weight when the study was extended through 6 months and 12 months. In 2007, further studies showed that Factor-4 was treating the Metabolic Syndrome and improving patient health in numerous ways.

POWER AMINO ACIDS® and supercharged health lead to a number of health benefits because they stimulate weight loss and achieve sustained weight control, combat Metabolic Syndrome that is associated with chronic degenerative diseases that are associated with accelerated aging and early death, revitalize youth with increased pep, energy, activity, stamina, endurance and performance, and increase anti-aging health with improved quality of life through feelings of "comfort, satisfaction and well-being."

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof in the above examples, it will be understood that modifications and variations are encompassed within the spirit and scope of the invention. Accordingly, the invention is limited only by the following claims.

What is claimed is:

1. A dietary supplement comprising:
   a first amino acid blend comprising free-form L-Lysine and free-form L-Arginine;
   a second amino acid blend comprising free-form L-Histidine and at least one free-form amino acid selected from among L-Isoleucine, L-Leucine, L-Threonine, L-Valine, Phenylalanine, L-Methionine, L-Tryptophan, and 5-Hydroxy Tryptophan; and
   a protein;
   wherein the free-form L-Lysine and free-form L-Arginine of the first amino acid blend and the free-form L-Histidine and, if present, the free-form L-Isoleucine, L-Leucine, L-Threonine, L-Valine, Phenylalanine, L-Methionine, and Tryptophan of the second amino acid blend are the only free-form amino acids in the supplement.

2. The dietary supplement of claim 1, wherein said supplement comprises between 10 mg and 3 g of said free-form L-Lysine per serving.

3. The dietary supplement of claim 1, wherein said supplement comprises between 10 mg and 3 g of said free-form L-Arginine per serving.

4. The dietary supplement of claim 1, wherein said supplement comprises between 10 mg and 3 g of said free-from L-Histidine per serving.

5. The dietary supplement of claim 1, wherein said dietary supplement is formulated in a powder or liquid form.

6. The dietary supplement of claim 1, wherein said free-form L-Lysine, L-Arginine, or L-Histidine is formulated for sustained or extended release.

7. The dietary supplement of claim 1 wherein said first amino acid blend comprises at least 10 mg free-form L-Lysine and at least 10 mg free-form L-Arginine per serving of said supplement.

8. The dietary supplement of claim 1 wherein said second amino acid blend comprises at least 10 mg free-form L-Histidine and at least one free-form amino acid selected from among L-Isoleucine, L-Leucine, L-Threonine, L-Valine, Phenylalanine, L-Methionine, and Tryptophan per serving of said supplement.

9. The dietary supplement of claim 8 wherein said second amino acid blend comprises between 10 mg and 3 g each of free-form L-Histidine, L-Isoleucine, L-Leucine, L-Threonine, L-Valine, Phenylalanine, L-Methionine, and Tryptophan per serving of said supplement.

10. The dietary supplement of claim 1 wherein said free-form Phenylalanine comprises free-form L-Phenylalanine and/or free-form dl-Phenylalanine.

11. The dietary supplement of claim 1, wherein the dietary supplement comprises between 1 g and 50 g of protein.

12. The dietary supplement of claim 1, wherein the protein is at least one protein selected from the group consisting of whey protein, egg protein, casein, and soy protein.

* * * * *